United States Patent
Patel et al.

(10) Patent No.: US 11,998,311 B2
(45) Date of Patent: Jun. 4, 2024

(54) GUIDEWIRE POSITIONING CATHETER

(71) Applicant: Avinger, Inc., Redwood City, CA (US)

(72) Inventors: Himanshu N. Patel, San Jose, CA (US); John B. Simpson, Woodside, CA (US)

(73) Assignee: Avinger, Inc., Redwood City, CA (US)

( * ) Notice: Subject to any disclaimer, the term of this patent is extended or adjusted under 35 U.S.C. 154(b) by 0 days.

(21) Appl. No.: 17/443,398

(22) Filed: Jul. 26, 2021

(65) Prior Publication Data
US 2021/0345903 A1    Nov. 11, 2021

Related U.S. Application Data

(63) Continuation of application No. 15/480,238, filed on Apr. 5, 2017, now Pat. No. 11,076,773, which is a
(Continued)

(51) Int. Cl.
*A61B 5/06* (2006.01)
*A61B 17/3207* (2006.01)
(Continued)

(52) U.S. Cl.
CPC ...... *A61B 5/066* (2013.01); *A61B 17/320758* (2013.01); *A61M 25/01* (2013.01);
(Continued)

(58) Field of Classification Search
CPC ...... A61B 17/320758; A61B 2017/003; A61B 2017/00309; A61B 2017/22038; A61M 25/0138; A61M 25/0147
See application file for complete search history.

(56) References Cited

U.S. PATENT DOCUMENTS

| 3,367,727 A | 2/1968 | Ward et al. |
| 3,908,637 A | 9/1975 | Doroshow |

(Continued)

FOREIGN PATENT DOCUMENTS

| CN | 1875242 A | 12/2006 |
| CN | 1947652 A | 4/2007 |

(Continued)

OTHER PUBLICATIONS

Patel et al.; U.S. Appl. No. 17/762,815 entitled "Atherectomy catheter with shapeable distal tip," filed Mar. 23, 2022.
(Continued)

*Primary Examiner* — Thomas McEvoy
(74) *Attorney, Agent, or Firm* — Shay Glenn LLP

(57) ABSTRACT

A catheter for positioning a guidewire across an occluded portion of a vessel includes an elongate catheter body, an integrated rotatable distal tip, a proximal handle region, and a catheter lumen extending through the elongate catheter body. The elongate body has a distal region configured to be bent to a set angle. The integrated rotatable distal tip includes one or more channeled flutes extending around the distal tip that are configured to be rotated in a first direction to dissect tissue and a second direction for bluntly contacting tissue. A proximal handle region includes a control for rotating the distal tip in either the first or second directions. The catheter lumen is configured to pass a guidewire.

22 Claims, 59 Drawing Sheets

Related U.S. Application Data continuation of application No. 13/929,579, filed on Jun. 27, 2013, now Pat. No. 9,642,646, which is a continuation of application No. 12/689,748, filed on Jan. 19, 2010, now Pat. No. 8,696,695.

(60) Provisional application No. 61/233,093, filed on Aug. 11, 2009, provisional application No. 61/173,542, filed on Apr. 28, 2009.

(51) Int. Cl.
*A61M 25/01* (2006.01)
*A61B 17/00* (2006.01)
*A61B 17/22* (2006.01)

(52) U.S. Cl.
CPC ... *A61M 25/0138* (2013.01); *A61B 2017/003* (2013.01); *A61B 2017/00309* (2013.01); *A61B 2017/22038* (2013.01); *A61B 2017/320775* (2013.01); *A61M 25/0147* (2013.01); *A61M 25/0155* (2013.01); *A61M 25/0172* (2013.01)

(56) References Cited

U.S. PATENT DOCUMENTS

| | | |
|---|---|---|
| 4,178,935 A | 12/1979 | Gekhaman et al. |
| 4,487,206 A | 12/1984 | Aagard |
| 4,527,553 A | 7/1985 | Upsher |
| 4,552,554 A | 11/1985 | Gould et al. |
| 4,578,061 A | 3/1986 | Lemelson |
| 4,598,710 A | 7/1986 | Kleinberg et al. |
| 4,611,600 A | 9/1986 | Cohen |
| 4,621,353 A | 11/1986 | Hazel et al. |
| 4,639,091 A | 1/1987 | Huignard et al. |
| 4,651,753 A | 3/1987 | Lifton |
| 4,654,024 A | 3/1987 | Crittenden et al. |
| 4,681,106 A | 7/1987 | Kensey et al. |
| 4,686,982 A | 8/1987 | Nash |
| 4,691,708 A | 9/1987 | Kane |
| 4,729,763 A | 3/1988 | Henrie |
| 4,771,774 A | 9/1988 | Simpson et al. |
| 4,781,186 A | 11/1988 | Simpson et al. |
| 4,841,977 A | 6/1989 | Griffith et al. |
| 4,842,578 A | 6/1989 | Johnson et al. |
| 4,850,354 A | 7/1989 | McGurk-Burleson et al. |
| 4,857,046 A | 8/1989 | Stevens et al. |
| 4,920,961 A | 5/1990 | Grossi et al. |
| 4,926,858 A | 5/1990 | Gifford, III et al. |
| 5,000,185 A | 3/1991 | Yock |
| 5,002,560 A | 3/1991 | Machold et al. |
| 5,018,529 A | 5/1991 | Tenerz et al. |
| 5,041,082 A | 8/1991 | Shiber |
| 5,047,040 A | 9/1991 | Simpson et al. |
| 5,085,662 A | 2/1992 | Willard |
| 5,099,850 A | 3/1992 | Matsui et al. |
| 5,178,153 A | 1/1993 | Einzig |
| 5,182,291 A | 1/1993 | Gubin et al. |
| 5,190,050 A | 3/1993 | Nitzsche |
| 5,192,291 A | 3/1993 | Pannek, Jr. |
| 5,217,479 A | 6/1993 | Shuler |
| 5,312,415 A | 5/1994 | Palermo |
| 5,312,425 A | 5/1994 | Evans et al. |
| 5,321,501 A | 6/1994 | Swanson et al. |
| 5,333,142 A | 7/1994 | Scheps |
| 5,358,472 A | 10/1994 | Vance et al. |
| 5,366,464 A | 11/1994 | Belknap |
| 5,372,601 A | 12/1994 | Lary |
| 5,383,460 A | 1/1995 | Jang et al. |
| 5,383,467 A | 1/1995 | Auer et al. |
| 5,425,273 A | 6/1995 | Chevalier |
| 5,425,371 A | 6/1995 | Mischenko |
| 5,429,136 A | 7/1995 | Milo et al. |
| 5,431,673 A | 7/1995 | Summers et al. |
| 5,437,284 A | 8/1995 | Trimble |
| 5,449,372 A | 9/1995 | Schmaltz et al. |
| 5,459,570 A | 10/1995 | Swanson et al. |
| 5,460,168 A | 10/1995 | Masubuchi et al. |
| 5,465,147 A | 11/1995 | Swanson |
| 5,507,725 A | 4/1996 | Savage et al. |
| 5,507,760 A | 4/1996 | Wynne et al. |
| 5,507,795 A | 4/1996 | Chiang et al. |
| 5,517,998 A | 5/1996 | Madison |
| 5,529,580 A | 6/1996 | Kusunok et al. |
| 5,556,405 A | 9/1996 | Lary |
| 5,607,394 A | 3/1997 | Andersen et al. |
| 5,613,981 A | 3/1997 | Boyle et al. |
| 5,620,426 A | 4/1997 | Braithwaite |
| 5,632,754 A | 5/1997 | Farley et al. |
| 5,632,755 A | 5/1997 | Nordgren et al. |
| 5,667,490 A * | 9/1997 | Keith ............ A61B 17/320758 604/905 |
| 5,674,232 A | 10/1997 | Halliburton |
| 5,676,012 A | 10/1997 | Ceriale |
| 5,681,336 A | 10/1997 | Clement et al. |
| 5,690,634 A | 11/1997 | Muller et al. |
| 5,722,403 A | 3/1998 | McGee et al. |
| 5,728,148 A | 3/1998 | Bostrom et al. |
| 5,749,846 A | 5/1998 | Edwards et al. |
| 5,795,295 A | 8/1998 | Hellmuth et al. |
| 5,807,339 A | 9/1998 | Bostrom et al. |
| 5,830,145 A | 11/1998 | Tenhoff |
| 5,836,957 A | 11/1998 | Schulz et al. |
| 5,843,050 A | 12/1998 | Jones et al. |
| 5,843,103 A | 12/1998 | Wulfman |
| 5,851,212 A | 12/1998 | Zirps et al. |
| 5,868,778 A | 2/1999 | Gershony et al. |
| 5,872,879 A | 2/1999 | Hamm |
| 5,904,651 A | 5/1999 | Swanson et al. |
| 5,907,425 A | 5/1999 | Dickensheets et al. |
| 5,935,075 A | 8/1999 | Casscells et al. |
| 5,935,139 A | 8/1999 | Bates |
| 5,938,602 A | 8/1999 | Lloyd |
| 5,938,671 A | 8/1999 | Katoh et al. |
| 5,951,482 A | 9/1999 | Winston et al. |
| 5,951,581 A | 9/1999 | Saadat et al. |
| 5,951,583 A | 9/1999 | Jensen et al. |
| 5,956,355 A | 9/1999 | Swanson et al. |
| 5,957,952 A | 9/1999 | Gershony et al. |
| 5,987,995 A | 11/1999 | Sawatari et al. |
| 5,997,558 A | 12/1999 | Nash |
| 6,001,112 A | 12/1999 | Taylor |
| 6,007,530 A | 12/1999 | Dornhofer et al. |
| 6,010,449 A | 1/2000 | Selmon et al. |
| 6,013,072 A | 1/2000 | Winston et al. |
| 6,017,359 A | 1/2000 | Gershony et al. |
| 6,027,514 A | 2/2000 | Stine et al. |
| 6,032,673 A | 3/2000 | Savage et al. |
| 6,048,349 A | 4/2000 | Winston et al. |
| 6,080,170 A | 6/2000 | Nash et al. |
| 6,106,515 A | 8/2000 | Winston et al. |
| 6,110,164 A | 8/2000 | Vidlund |
| 6,120,515 A | 9/2000 | Rogers et al. |
| 6,120,516 A | 9/2000 | Selmon et al. |
| 6,134,002 A | 10/2000 | Stimson et al. |
| 6,134,003 A | 10/2000 | Tearney et al. |
| 6,152,938 A | 11/2000 | Curry |
| 6,152,951 A | 11/2000 | Hashimoto et al. |
| 6,160,826 A | 12/2000 | Swanson et al. |
| 6,175,669 B1 | 1/2001 | Colston et al. |
| 6,176,871 B1 | 1/2001 | Pathak et al. |
| 6,183,432 B1 | 2/2001 | Milo |
| 6,193,676 B1 | 2/2001 | Winston et al. |
| 6,206,898 B1 | 3/2001 | Honeycutt et al. |
| 6,228,076 B1 | 5/2001 | Winston et al. |
| 6,241,744 B1 | 6/2001 | Imran et al. |
| 6,283,957 B1 | 9/2001 | Hashimoto et al. |
| 6,285,903 B1 | 9/2001 | Rosenthal et al. |
| 6,290,668 B1 | 9/2001 | Gregory et al. |
| 6,294,775 B1 | 9/2001 | Seibel et al. |
| 6,299,622 B1 | 10/2001 | Snow et al. |
| 6,307,985 B1 | 10/2001 | Murakami et al. |
| 6,375,615 B1 | 4/2002 | Flaherty et al. |
| 6,402,719 B1 | 6/2002 | Ponzi et al. |
| 6,416,527 B1 | 7/2002 | Berg et al. |

(56) References Cited

U.S. PATENT DOCUMENTS

| | | |
|---|---|---|
| 6,445,939 B1 | 9/2002 | Swanson et al. |
| 6,445,944 B1 | 9/2002 | Ostrovsky |
| 6,447,525 B2 | 9/2002 | Follmer et al. |
| 6,451,009 B1 | 9/2002 | Dasilva et al. |
| 6,451,036 B1 | 9/2002 | Heitzmann et al. |
| 6,454,717 B1 | 9/2002 | Pantages et al. |
| 6,454,779 B1 | 9/2002 | Taylor |
| 6,482,216 B1 | 11/2002 | Hiblar et al. |
| 6,482,217 B1 | 11/2002 | Pintor et al. |
| 6,485,413 B1 | 11/2002 | Boppart et al. |
| 6,497,649 B2 | 12/2002 | Parker et al. |
| 6,501,551 B1 | 12/2002 | Tearney et al. |
| 6,503,261 B1 | 1/2003 | Bruneau et al. |
| 6,511,458 B2 | 1/2003 | Milo et al. |
| 6,517,528 B1 | 2/2003 | Pantages et al. |
| 6,542,665 B2 | 4/2003 | Reed et al. |
| 6,544,230 B1 | 4/2003 | Flaherty et al. |
| 6,546,272 B1 | 4/2003 | MacKinnon et al. |
| 6,551,302 B1 | 4/2003 | Rosinko et al. |
| 6,563,105 B2 | 5/2003 | Seibel et al. |
| 6,564,087 B1 | 5/2003 | Pitris et al. |
| 6,565,588 B1 | 5/2003 | Clement et al. |
| 6,572,563 B2 | 6/2003 | Ouchi et al. |
| 6,572,643 B1 | 6/2003 | Gharibadeh |
| 6,575,995 B1 | 6/2003 | Huter et al. |
| 6,579,298 B1 | 6/2003 | Bruneau et al. |
| 6,599,296 B1 | 7/2003 | Gillick et al. |
| 6,615,071 B1 | 9/2003 | Casscells, III et al. |
| 6,629,953 B1 | 10/2003 | Boyd |
| 6,638,233 B2 | 10/2003 | Corvi et al. |
| 6,645,217 B1 | 11/2003 | MacKinnon et al. |
| 6,657,727 B1 | 12/2003 | Izatt et al. |
| 6,666,874 B2 | 12/2003 | Heitzmann et al. |
| 6,673,042 B1 | 1/2004 | Samson et al. |
| 6,687,010 B1 | 2/2004 | Horii |
| 6,728,571 B1 | 4/2004 | Barbato |
| D489,973 S | 5/2004 | Root et al. |
| 6,730,063 B2 | 5/2004 | Delaney et al. |
| 6,758,854 B1 | 7/2004 | Butler et al. |
| 6,760,112 B2 | 7/2004 | Reed et al. |
| 6,800,085 B2 | 10/2004 | Selmon et al. |
| 6,818,001 B2 | 11/2004 | Wulfman et al. |
| 6,824,550 B1 | 11/2004 | Noriega et al. |
| 6,830,577 B2 | 12/2004 | Nash et al. |
| 6,845,190 B1 | 1/2005 | Smithwick et al. |
| 6,852,109 B2 | 2/2005 | Winston et al. |
| 6,853,457 B2 | 2/2005 | Bjarklev et al. |
| 6,856,712 B2 | 2/2005 | Fauver et al. |
| 6,867,753 B2 | 3/2005 | Chinthammit et al. |
| 6,879,851 B2 | 4/2005 | McNamara et al. |
| 6,947,787 B2 | 9/2005 | Webler |
| 6,961,123 B1 | 11/2005 | Wang et al. |
| 6,970,732 B2 | 11/2005 | Winston et al. |
| 6,975,898 B2 | 12/2005 | Seibel |
| 7,068,878 B2 | 6/2006 | Crossman-Bosworth et al. |
| 7,074,231 B2 | 7/2006 | Jang |
| 7,126,693 B2 | 10/2006 | Everett et al. |
| 7,172,610 B2 | 2/2007 | Heitzmann et al. |
| 7,242,480 B2 | 7/2007 | Alphonse |
| 7,261,687 B2 | 8/2007 | Yang |
| 7,288,087 B2 | 10/2007 | Winston et al. |
| 7,291,146 B2 | 11/2007 | Steinke et al. |
| 7,297,131 B2 | 11/2007 | Nita |
| 7,311,723 B2 | 12/2007 | Seibel et al. |
| 7,344,546 B2 | 3/2008 | Wulfman et al. |
| 7,366,376 B2 | 4/2008 | Shishkov et al. |
| 7,382,949 B2 | 6/2008 | Bouma et al. |
| 7,426,036 B2 | 9/2008 | Feldchtein et al. |
| 7,428,001 B2 | 9/2008 | Schowengerdt et al. |
| 7,428,053 B2 | 9/2008 | Feldchtein et al. |
| 7,455,649 B2 | 11/2008 | Root et al. |
| 7,474,407 B2 | 1/2009 | Gutin |
| 7,485,127 B2 | 2/2009 | Nistal |
| 7,488,340 B2 | 2/2009 | Kauphusman et al. |
| 7,530,948 B2 | 5/2009 | Seibel et al. |
| 7,530,976 B2 | 5/2009 | MacMahon et al. |
| 7,538,859 B2 | 5/2009 | Teamney et al. |
| 7,538,886 B2 | 5/2009 | Feldchtein |
| 7,539,362 B2 | 5/2009 | Teramura |
| 7,542,145 B2 | 6/2009 | Toida et al. |
| 7,544,162 B2 | 6/2009 | Ohkubo |
| 7,545,504 B2 | 6/2009 | Buckland et al. |
| 7,555,333 B2 | 6/2009 | Wang et al. |
| 7,577,471 B2 | 8/2009 | Camus et al. |
| 7,583,872 B2 | 9/2009 | Seibel et al. |
| 7,616,986 B2 | 11/2009 | Seibel et al. |
| 7,637,885 B2 | 12/2009 | Maschke |
| 7,674,253 B2 | 3/2010 | Fisher et al. |
| 7,682,319 B2 | 3/2010 | Martin et al. |
| 7,706,863 B2 | 4/2010 | Imanishi et al. |
| 7,728,985 B2 | 6/2010 | Feldchtein et al. |
| 7,729,745 B2 | 6/2010 | Maschke |
| 7,734,332 B2 | 6/2010 | Sher |
| 7,738,945 B2 | 6/2010 | Fauver et al. |
| 7,753,852 B2 | 7/2010 | Maschke |
| 7,771,425 B2 | 8/2010 | Dycus et al. |
| 7,776,062 B2 | 8/2010 | Bessellink et al. |
| 7,785,286 B2 | 8/2010 | Magnin et al. |
| 7,813,609 B2 | 10/2010 | Petersen et al. |
| 7,821,643 B2 | 10/2010 | Amazeen et al. |
| 7,824,089 B2 | 11/2010 | Charles |
| 7,840,283 B1 | 11/2010 | Bush et al. |
| 7,944,568 B2 | 5/2011 | Teramura et al. |
| 7,952,718 B2 | 5/2011 | Li et al. |
| 7,972,299 B2 | 7/2011 | Carter et al. |
| 8,002,763 B2 | 8/2011 | Berthiaume et al. |
| 8,059,274 B2 | 11/2011 | Splinter |
| 8,062,316 B2 | 11/2011 | Patel et al. |
| 8,068,921 B2 | 11/2011 | Prakash et al. |
| 8,313,493 B2 | 11/2012 | Fisher |
| 8,361,097 B2 | 1/2013 | Patel et al. |
| 8,548,571 B2 | 10/2013 | He et al. |
| 8,548,603 B2 | 10/2013 | Swoyer et al. |
| 8,632,557 B2 | 1/2014 | Thatcher et al. |
| 8,644,913 B2 | 2/2014 | Simpson et al. |
| 8,647,335 B2 | 2/2014 | Markus |
| 8,696,695 B2 | 4/2014 | Patel et al. |
| 8,911,459 B2 | 12/2014 | Simpson et al. |
| 9,125,562 B2 | 9/2015 | Spencer et al. |
| 9,333,007 B2 | 5/2016 | Escudero et al. |
| 9,345,398 B2 | 5/2016 | Tachibana et al. |
| 9,345,406 B2 | 5/2016 | Spencer et al. |
| 9,345,510 B2 | 5/2016 | Patel et al. |
| 9,498,247 B2 | 11/2016 | Patel et al. |
| 9,498,600 B2 | 11/2016 | Rosenthal et al. |
| 9,557,156 B2 | 1/2017 | Kankaria |
| 9,572,492 B2 | 2/2017 | Simpson et al. |
| 9,592,075 B2 | 3/2017 | Simpson et al. |
| 9,642,646 B2 | 5/2017 | Patel et al. |
| 9,788,790 B2 | 10/2017 | Black et al. |
| 9,854,979 B2 | 1/2018 | Smith et al. |
| 9,918,734 B2 | 3/2018 | Patel et al. |
| 9,949,754 B2 | 4/2018 | Newhauser et al. |
| 10,052,125 B2 | 8/2018 | Rosenthal et al. |
| 10,130,386 B2 | 11/2018 | Simpson et al. |
| 10,244,934 B2 | 4/2019 | Tachibana et al. |
| 10,342,491 B2 | 7/2019 | Black et al. |
| 10,349,974 B2 | 7/2019 | Patel et al. |
| 10,357,277 B2 | 7/2019 | Patel et al. |
| 10,363,062 B2 | 7/2019 | Spencer et al. |
| 10,470,795 B2 | 11/2019 | Patel et al. |
| 10,548,478 B2 | 2/2020 | Simpson et al. |
| 10,568,520 B2 | 2/2020 | Patel et al. |
| 10,568,655 B2 | 2/2020 | Simpson et al. |
| 10,722,121 B2 | 7/2020 | Smith et al. |
| 10,729,326 B2 | 8/2020 | Spencer et al. |
| 10,860,484 B2 | 12/2020 | Simpson et al. |
| 10,869,685 B2 | 12/2020 | Patel et al. |
| 10,932,670 B2 | 3/2021 | Smith et al. |
| 10,952,615 B2 | 3/2021 | Kankaria |
| 10,952,763 B2 | 3/2021 | Newhauser et al. |
| 11,033,190 B2 | 6/2021 | Patel et al. |
| 11,076,773 B2 | 8/2021 | Patel et al. |
| 11,096,717 B2 | 8/2021 | Gupta et al. |

(56) References Cited

U.S. PATENT DOCUMENTS

| | | |
|---|---|---|
| 11,134,849 B2 | 10/2021 | Simpson et al. |
| 11,135,019 B2 | 10/2021 | Spencer et al. |
| 11,147,583 B2 | 10/2021 | Patel et al. |
| 2001/0005788 A1 | 6/2001 | McGuckin, Jr. |
| 2001/0020126 A1 | 9/2001 | Swanson et al. |
| 2002/0019644 A1 | 2/2002 | Hastings et al. |
| 2002/0072706 A1 | 6/2002 | Hiblar et al. |
| 2002/0082585 A1 | 6/2002 | Carroll et al. |
| 2002/0082626 A1 | 6/2002 | Donohoe et al. |
| 2002/0097400 A1 | 7/2002 | Jung et al. |
| 2002/0111548 A1 | 8/2002 | Swanson et al. |
| 2002/0115931 A1 | 8/2002 | Strauss et al. |
| 2002/0138091 A1 | 9/2002 | Pflueger |
| 2002/0147459 A1 | 10/2002 | Bashiri et al. |
| 2002/0158547 A1 | 10/2002 | Wood |
| 2003/0002038 A1 | 1/2003 | Mawatari |
| 2003/0028100 A1 | 2/2003 | Tearney et al. |
| 2003/0032880 A1 | 2/2003 | Moore |
| 2003/0045835 A1 | 3/2003 | Anderson et al. |
| 2003/0095248 A1 | 5/2003 | Frot |
| 2003/0097044 A1 | 5/2003 | Rovegno |
| 2003/0120150 A1 | 6/2003 | Govari |
| 2003/0120295 A1 | 6/2003 | Simpson et al. |
| 2003/0125756 A1 | 7/2003 | Shturman et al. |
| 2003/0125757 A1 | 7/2003 | Patel et al. |
| 2003/0125758 A1 | 7/2003 | Simpson et al. |
| 2003/0139751 A1 | 7/2003 | Evans et al. |
| 2003/0181855 A1 | 9/2003 | Simpson et al. |
| 2004/0002650 A1 | 1/2004 | Mandrusov et al. |
| 2004/0039371 A1 | 2/2004 | Tockman et al. |
| 2004/0057667 A1 | 3/2004 | Yamada et al. |
| 2004/0059257 A1 | 3/2004 | Gaber |
| 2004/0082850 A1 | 4/2004 | Bonner et al. |
| 2004/0092915 A1 | 5/2004 | Levatter |
| 2004/0093001 A1 | 5/2004 | Hamada |
| 2004/0147934 A1 | 7/2004 | Kiester |
| 2004/0167553 A1 | 8/2004 | Simpson et al. |
| 2004/0167554 A1 | 8/2004 | Simpson et al. |
| 2004/0181249 A1 | 9/2004 | Torrance et al. |
| 2004/0186368 A1 | 9/2004 | Ramzipoor et al. |
| 2004/0193140 A1 | 9/2004 | Griffin et al. |
| 2004/0202418 A1 | 10/2004 | Ghiron et al. |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0236312 A1 | 11/2004 | Nistal et al. |
| 2004/0243162 A1 | 12/2004 | Wulfman et al. |
| 2004/0254599 A1 | 12/2004 | Lipoma et al. |
| 2004/0260236 A1 | 12/2004 | Manning et al. |
| 2005/0020925 A1 | 1/2005 | Kleen et al. |
| 2005/0021075 A1 | 1/2005 | Bonnette et al. |
| 2005/0027199 A1 | 2/2005 | Clarke |
| 2005/0043614 A1 | 2/2005 | Huizenga et al. |
| 2005/0054947 A1 | 3/2005 | Goldenberg |
| 2005/0075660 A1 | 4/2005 | Chu et al. |
| 2005/0085708 A1 | 4/2005 | Fauver et al. |
| 2005/0085721 A1 | 4/2005 | Fauver et al. |
| 2005/0105097 A1 | 5/2005 | Fang-Yen et al. |
| 2005/0141843 A1 | 6/2005 | Warden et al. |
| 2005/0149096 A1 | 7/2005 | Hilal et al. |
| 2005/0154407 A1 | 7/2005 | Simpson |
| 2005/0159712 A1 | 7/2005 | Andersen |
| 2005/0159731 A1 | 7/2005 | Lee |
| 2005/0171478 A1 | 8/2005 | Selmon et al. |
| 2005/0177068 A1 | 8/2005 | Simpson |
| 2005/0182295 A1 | 8/2005 | Soper et al. |
| 2005/0187571 A1 | 8/2005 | Maschke |
| 2005/0192496 A1 | 9/2005 | Maschke |
| 2005/0197623 A1 | 9/2005 | Leeflang et al. |
| 2005/0201662 A1 | 9/2005 | Petersen et al. |
| 2005/0203553 A1 | 9/2005 | Maschke |
| 2005/0222519 A1 | 10/2005 | Simpson |
| 2005/0222663 A1 | 10/2005 | Simpson et al. |
| 2005/0251116 A1 | 11/2005 | Steinke et al. |
| 2006/0011820 A1 | 1/2006 | Chow-Shing et al. |
| 2006/0032508 A1 | 2/2006 | Simpson |
| 2006/0046235 A1 | 3/2006 | Alexander |
| 2006/0049587 A1 | 3/2006 | Cornwell |
| 2006/0064009 A1 | 3/2006 | Webler et al. |
| 2006/0084911 A1 | 4/2006 | Belef et al. |
| 2006/0109478 A1 | 5/2006 | Tearney et al. |
| 2006/0135870 A1 | 6/2006 | Webler |
| 2006/0173475 A1 | 8/2006 | Lafontaine et al. |
| 2006/0229646 A1 | 10/2006 | Sparks |
| 2006/0229659 A1 | 10/2006 | Gifford et al. |
| 2006/0235262 A1 | 10/2006 | Amal et al. |
| 2006/0235366 A1 | 10/2006 | Simpson |
| 2006/0236019 A1 | 10/2006 | Soito et al. |
| 2006/0239982 A1 | 10/2006 | Simpson |
| 2006/0241503 A1 | 10/2006 | Schmitt et al. |
| 2006/0244973 A1 | 11/2006 | Yun et al. |
| 2006/0252993 A1 | 11/2006 | Freed et al. |
| 2006/0264741 A1 | 11/2006 | Prince |
| 2006/0264743 A1 | 11/2006 | Kleen et al. |
| 2006/0264907 A1 | 11/2006 | Eskridge et al. |
| 2007/0010840 A1 | 1/2007 | Rosenthal et al. |
| 2007/0015969 A1 | 1/2007 | Feldman et al. |
| 2007/0015979 A1 | 1/2007 | Redel |
| 2007/0035855 A1 | 2/2007 | Dickensheets |
| 2007/0038061 A1 | 2/2007 | Huennekens et al. |
| 2007/0038125 A1 | 2/2007 | Kleen et al. |
| 2007/0038173 A1 | 2/2007 | Simpson |
| 2007/0050019 A1 | 3/2007 | Hyde |
| 2007/0078469 A1 | 4/2007 | Soito et al. |
| 2007/0078500 A1 | 4/2007 | Ryan et al. |
| 2007/0081166 A1 | 4/2007 | Brown et al. |
| 2007/0088230 A1 | 4/2007 | Terashi et al. |
| 2007/0106155 A1 | 5/2007 | Goodnow et al. |
| 2007/0135712 A1 | 6/2007 | Maschke |
| 2007/0167710 A1 | 7/2007 | Unal et al. |
| 2007/0196926 A1 | 8/2007 | Soito et al. |
| 2007/0213618 A1 | 9/2007 | Li et al. |
| 2007/0219484 A1 | 9/2007 | Straub |
| 2007/0250080 A1 | 10/2007 | Jones et al. |
| 2007/0255252 A1 | 11/2007 | Mehta |
| 2007/0270647 A1 | 11/2007 | Nahen et al. |
| 2007/0276419 A1 | 11/2007 | Rosenthal |
| 2007/0288036 A1 | 12/2007 | Seshadri |
| 2007/0299309 A1 | 12/2007 | Seibel et al. |
| 2008/0004643 A1 | 1/2008 | To et al. |
| 2008/0004644 A1 | 1/2008 | To et al. |
| 2008/0004645 A1 | 1/2008 | To et al. |
| 2008/0004646 A1 | 1/2008 | To et al. |
| 2008/0015491 A1 | 1/2008 | Bei et al. |
| 2008/0015618 A1 | 1/2008 | Sonnenschein et al. |
| 2008/0027334 A1 | 1/2008 | Langston |
| 2008/0033396 A1 | 2/2008 | Danek et al. |
| 2008/0045986 A1 | 2/2008 | To et al. |
| 2008/0049234 A1 | 2/2008 | Seitz |
| 2008/0058629 A1 | 3/2008 | Seibel et al. |
| 2008/0065124 A1 | 3/2008 | Olson |
| 2008/0065125 A1 | 3/2008 | Olson |
| 2008/0065205 A1 | 3/2008 | Nguyen et al. |
| 2008/0095421 A1 | 4/2008 | Sun et al. |
| 2008/0103439 A1 | 5/2008 | Torrance et al. |
| 2008/0103446 A1 | 5/2008 | Torrance et al. |
| 2008/0103516 A1 | 5/2008 | Wulfman et al. |
| 2008/0132929 A1 | 6/2008 | O'Sullivan et al. |
| 2008/0139897 A1 | 6/2008 | Ainsworth et al. |
| 2008/0146942 A1 | 6/2008 | Dala-Krishna |
| 2008/0147000 A1 | 6/2008 | Seibel et al. |
| 2008/0154293 A1 | 6/2008 | Taylor et al. |
| 2008/0154296 A1 | 6/2008 | Taylor et al. |
| 2008/0177138 A1 | 7/2008 | Courtney et al. |
| 2008/0186501 A1 | 8/2008 | Xie |
| 2008/0207996 A1 | 8/2008 | Tsai |
| 2008/0221388 A1 | 9/2008 | Seibel et al. |
| 2008/0228033 A1 | 9/2008 | Tumlinson et al. |
| 2008/0243030 A1 | 10/2008 | Seibel et al. |
| 2008/0243031 A1 | 10/2008 | Seibel et al. |
| 2008/0262312 A1 | 10/2008 | Carroll et al. |
| 2008/0275485 A1 | 11/2008 | Bonnette et al. |
| 2009/0018565 A1 | 1/2009 | To et al. |
| 2009/0018566 A1 | 1/2009 | Escudero et al. |

(56) References Cited

U.S. PATENT DOCUMENTS

| | | |
|---|---|---|
| 2009/0018567 A1 | 1/2009 | Escudero et al. |
| 2009/0024084 A1 | 1/2009 | Khosla et al. |
| 2009/0024085 A1 | 1/2009 | To et al. |
| 2009/0024191 A1 | 1/2009 | Seibel et al. |
| 2009/0028407 A1 | 1/2009 | Seibel et al. |
| 2009/0028507 A1 | 1/2009 | Jones et al. |
| 2009/0043191 A1 | 2/2009 | Castella et al. |
| 2009/0073444 A1 | 3/2009 | Wang |
| 2009/0076447 A1 | 3/2009 | Casas et al. |
| 2009/0093764 A1 | 4/2009 | Pfeffer et al. |
| 2009/0099641 A1 | 4/2009 | Wu et al. |
| 2009/0125019 A1 | 5/2009 | Douglass et al. |
| 2009/0135280 A1 | 5/2009 | Johnston et al. |
| 2009/0137893 A1 | 5/2009 | Seibel et al. |
| 2009/0152664 A1 | 6/2009 | Tian et al. |
| 2009/0185135 A1 | 7/2009 | Volk |
| 2009/0196477 A1 | 8/2009 | Cense |
| 2009/0196554 A1 | 8/2009 | Irisawa |
| 2009/0198125 A1 | 8/2009 | Nakabayashi et al. |
| 2009/0208143 A1 | 8/2009 | Yoon et al. |
| 2009/0216180 A1 | 8/2009 | Lee et al. |
| 2009/0221904 A1 | 9/2009 | Shealy et al. |
| 2009/0221920 A1 | 9/2009 | Boppart et al. |
| 2009/0234220 A1 | 9/2009 | Maschke |
| 2009/0235396 A1 | 9/2009 | Wang et al. |
| 2009/0244485 A1 | 10/2009 | Walsh et al. |
| 2009/0244547 A1 | 10/2009 | Ozawa |
| 2009/0264826 A1 | 10/2009 | Thompson |
| 2009/0268159 A1 | 10/2009 | Xu et al. |
| 2009/0275966 A1 | 11/2009 | Mitusina |
| 2009/0284749 A1 | 11/2009 | Johnson et al. |
| 2009/0292199 A1 | 11/2009 | Bielewicz et al. |
| 2009/0306520 A1 | 12/2009 | Schmitt et al. |
| 2009/0316116 A1 | 12/2009 | Melville et al. |
| 2009/0318862 A1 | 12/2009 | Ali et al. |
| 2010/0004544 A1 | 1/2010 | Toida |
| 2010/0021926 A1 | 1/2010 | Noordin |
| 2010/0049225 A1 | 2/2010 | To et al. |
| 2010/0080016 A1 | 4/2010 | Fukui et al. |
| 2010/0082000 A1 | 4/2010 | Honeck et al. |
| 2010/0125253 A1 | 5/2010 | Olson |
| 2010/0130996 A1 | 5/2010 | Doud et al. |
| 2010/0198081 A1 | 8/2010 | Hanlin et al. |
| 2010/0217245 A1 | 8/2010 | Prescott |
| 2010/0241147 A1 | 9/2010 | Maschke |
| 2010/0253949 A1 | 10/2010 | Adler et al. |
| 2010/0292539 A1 | 11/2010 | Lankenau et al. |
| 2010/0292721 A1 | 11/2010 | Moberg |
| 2010/0312263 A1 | 12/2010 | Moberg et al. |
| 2010/0317973 A1 | 12/2010 | Nita |
| 2010/0324472 A1 | 12/2010 | Wulfman |
| 2011/0023617 A1 | 2/2011 | Yu et al. |
| 2011/0028977 A1 | 2/2011 | Rauscher et al. |
| 2011/0040238 A1 | 2/2011 | Wulfman et al. |
| 2011/0058250 A1 | 3/2011 | Liu et al. |
| 2011/0060186 A1 | 3/2011 | Tilson et al. |
| 2011/0071401 A1 | 3/2011 | Hastings et al. |
| 2011/0092955 A1 | 4/2011 | Purdy et al. |
| 2011/0106004 A1 | 5/2011 | Eubanks et al. |
| 2011/0118660 A1 | 5/2011 | Torrance et al. |
| 2011/0130777 A1 | 6/2011 | Zhang et al. |
| 2011/0144673 A1 | 6/2011 | Zhang et al. |
| 2011/0201924 A1 | 8/2011 | Tearney et al. |
| 2011/0295148 A1 | 12/2011 | Destoumieux et al. |
| 2011/0301625 A1 | 12/2011 | Mauch et al. |
| 2012/0002928 A1 | 1/2012 | Irisawa |
| 2012/0238869 A1 | 9/2012 | Schmitt et al. |
| 2012/0277730 A1 | 11/2012 | Salahieh et al. |
| 2013/0184549 A1 | 7/2013 | Avitall et al. |
| 2013/0331819 A1 | 12/2013 | Rosenman et al. |
| 2014/0005534 A1 | 1/2014 | He et al. |
| 2015/0141816 A1 | 5/2015 | Gupta et al. |
| 2015/0320975 A1 | 11/2015 | Simpson et al. |
| 2016/0144155 A1 | 5/2016 | Simpson et al. |
| 2018/0207417 A1 | 7/2018 | Zung et al. |
| 2019/0021679 A1 | 1/2019 | Christensen |
| 2019/0029714 A1 | 1/2019 | Patel et al. |
| 2019/0110809 A1 | 4/2019 | Rosenthal et al. |
| 2019/0209206 A1 | 7/2019 | Patel et al. |
| 2019/0313941 A1 | 10/2019 | Radjabi |
| 2020/0029801 A1 | 1/2020 | Tachibana et al. |
| 2020/0060718 A1 | 2/2020 | Patel et al. |
| 2020/0069253 A1 | 3/2020 | Black et al. |
| 2020/0315654 A1 | 10/2020 | Patel et al. |
| 2020/0323553 A1 | 10/2020 | Fernandez et al. |
| 2021/0059713 A1 | 3/2021 | Patel et al. |
| 2021/0076949 A1 | 3/2021 | Smith et al. |
| 2021/0177262 A1 | 6/2021 | Spencer et al. |
| 2021/0267621 A1 | 9/2021 | Simpson et al. |
| 2022/0071656 A1 | 3/2022 | Patel et al. |
| 2022/0168011 A1 | 6/2022 | Patel et al. |
| 2022/0240860 A1 | 8/2022 | Black et al. |

FOREIGN PATENT DOCUMENTS

| | | |
|---|---|---|
| CN | 101601581 A | 12/2009 |
| DE | 202006018883.5 U | 2/2007 |
| EP | 0347098 A2 | 12/1989 |
| EP | 0808638 A1 | 11/1997 |
| EP | 0845692 B1 | 11/2005 |
| EP | 1859732 A1 | 11/2007 |
| EP | 2090245 A1 | 8/2009 |
| EP | 2353526 B1 | 9/2013 |
| JP | S62-275425 A | 11/1987 |
| JP | 03502060 A | 2/1990 |
| JP | H05501065 A | 3/1993 |
| JP | 05103763 A | 4/1993 |
| JP | 06027343 A | 2/1994 |
| JP | H07184888 A | 7/1995 |
| JP | 07308393 A | 11/1995 |
| JP | 2002214127 A | 7/2002 |
| JP | 2004509695 A | 4/2004 |
| JP | 2004516073 A | 6/2004 |
| JP | 2005114473 A | 4/2005 |
| JP | 2005230550 A | 9/2005 |
| JP | 2005249704 A | 9/2005 |
| JP | 2005533533 A | 11/2005 |
| JP | 2008175698 A | 7/2006 |
| JP | 2006288775 A | 10/2006 |
| JP | 2006313158 A | 11/2006 |
| JP | 2006526790 A | 11/2006 |
| JP | 2006326157 A | 12/2006 |
| JP | 200783053 A | 4/2007 |
| JP | 200783057 A | 4/2007 |
| JP | 2007225349 A | 9/2007 |
| JP | 2007533361 A | 11/2007 |
| JP | 2008023627 | 2/2008 |
| JP | 2008128708 A | 6/2008 |
| JP | 2008145376 A | 6/2008 |
| JP | 2008183208 A | 8/2008 |
| JP | 2008253492 A | 10/2008 |
| JP | 200914751 A | 1/2009 |
| JP | 2009509690 A | 3/2009 |
| JP | 200978150 A | 4/2009 |
| JP | 2009066252 A | 4/2009 |
| JP | 2009201969 A | 9/2009 |
| JP | 2010042182 A | 2/2010 |
| JP | 2010518900 A | 6/2010 |
| JP | 2011521747 A | 7/2011 |
| JP | 2012533353 A | 12/2012 |
| JP | 2013512736 A | 4/2013 |
| KR | 2007/0047221 A | 5/2007 |
| RU | 2185859 C2 | 7/2002 |
| RU | 2218191 C2 | 12/2003 |
| WO | WO91/17698 A1 | 11/1991 |
| WO | WO99/23958 A1 | 5/1999 |
| WO | WO00/54659 A1 | 9/2000 |
| WO | WO01/15609 A1 | 3/2001 |
| WO | WO01/76680 A1 | 10/2001 |
| WO | WO2006/133030 A2 | 12/2006 |
| WO | WO2008/005888 A2 | 1/2008 |
| WO | WO2008/029506 A1 | 3/2008 |
| WO | WO2008/042987 A2 | 4/2008 |
| WO | WO2008/051951 A1 | 5/2008 |

(56) References Cited

FOREIGN PATENT DOCUMENTS

| | | |
|---|---|---|
| WO | WO2008/065600 A2 | 6/2008 |
| WO | WO2008/086613 A1 | 7/2008 |
| WO | WO2008/087613 A2 | 7/2008 |
| WO | WO2008/151155 A2 | 12/2008 |
| WO | WO2009/005779 A1 | 1/2009 |
| WO | WO2009/006335 A1 | 1/2009 |
| WO | WO2009/009799 A1 | 1/2009 |
| WO | WO2009/009802 A1 | 1/2009 |
| WO | WO2009/023635 A1 | 2/2009 |
| WO | WO2009/024344 A1 | 2/2009 |
| WO | WO2009/094341 A2 | 7/2009 |
| WO | WO2009/140617 A2 | 11/2009 |
| WO | WO2009/148317 A1 | 12/2009 |
| WO | WO2010/039464 A1 | 4/2010 |
| WO | WO2010/056771 A1 | 5/2010 |
| WO | WO2011/044387 A2 | 4/2011 |
| WO | WO2011/062087 A1 | 5/2011 |

OTHER PUBLICATIONS

Patel.; U.S. Appl. No. 17/763,810 entitled "Occlusion-crossing devices," filed Mar. 25, 2022.
Fernandez et al.; U.S. Appl. No. 17/747,715 entitled "Catheter device with detachable distal end," filed May 18, 2022.
Patel et al.; U.S. Appl. No. 17/749,882 entitled "Atherectomy Catheter," filed May 20, 2022.
Aziz et al.; Chronic total occlusions—a stiff challege requiring a major breakthrough: is there light at the end of the tunnel?; Heart; vol. 91; suppl. III; pp. 42-48; Jun. 2005.
Bayer Material Science: ; Snap-Fit Joints for Plastics; 26 pages; retrieved from the Internet: ( https://web.archive.org/web/20121119232733if_/http://fab.cba.mit.edu:80/classes/S62.12/people/vemnelle.noel/Plastic_Snap_fit_design.pdf) on Sep. 26, 2018.
Choma et al.; Sensitivity advantage of swept source and fourier domain optical coherence tomography; Optics Express; 11(18); pp. 2183-2189; Sep. 8, 2003.
De Boer et al.; Improved signal-to-noise ratio in spectral-domain compared with time-domain optical coherence tomography; Optics Letters; 28(21); pp. 2067-2069; Nov. 2003.
Emkey et al.; Analysis and evaluation of graded-index fiber-lenses; Journal of Lightwave Technology; vol. LT-5; No. 9; pp. 1156-1164; Sep. 1987.
Gonzalo et al.; Optical coherence tomography patterns of stent restenosis; Am. Heart J.; 158(2); pp. 284-293; Aug. 2009.
Han et al.; In situ Frog Retina Imaging Using Common-Path OCT with a Gold-Coated Bare Fiber Probe; CFM6; San Jose, California; CLEO, May 4, 2008; 2 pages.
Leitgeb et al.; Performance of fourier domain vs time domain optical coherence tomography; Optics Express; 11(8); pp. 889-894; Apr. 21, 2003.
Linares et al.; Arbitrary single-mode coupling by tapered and nontapered grin fiber lenses; Applied Optics; vol. 29; No. 28; pp. 4003-4007; Oct. 1, 1990.
Merriam Webster; Proximal (Definition); 10 pages; retrieved from the internet (https://www.merriam-webster.com/dictionary/proximal) on Jun. 9, 2021.

Muller et al.; Time-gated infrared fourier-domain optical coherence tomography; CFM5; San Jose, California; CLEO May 4, 2008; 2 pages.
Rollins et al.; Optimal interferometer designs for optical coherence tomography; Optics Letters; 24(21); pp. 1484-1486; Nov. 1999.
Schmitt et al.; A new rotational thrombectomy catheter: System design and first clinical experiences; Cardiovascular and Interventional Radiology; Springer-Verlag; 22(6); pp. 504-509; Nov. 1, 1999.
Sharma et al.; Common-path optical coherence tomography with side-viewing bare fiber probe for endoscopic optical coherence tomography; Rev. Sci. Instrum.; vol. 78; 113102; 5 pages: Nov. 6, 2007.
Sharma et al.; Optical coherence tomography based on an all-fiber autocorrelator using probe-end reflection as reference; CWJ13; San Francisco, California; CLEO May 16, 2004; 4 pages.
Stamper et al.; Plaque characterization with optical coherence tomography. Journal of the American College of Cardiology. 47(8); pp. 69-79; Apr. 18, 2006.
Suparno et al.; Light scattering with single-mode fiber collimators; Applied Optics; vol. 33; No. 30; pp. 7200-7205; Oct. 20, 1994.
Tanaka et al.; Challenges on the frontier of intracoronary imaging: atherosclerotic plaque macrophage measurement by optical coherence tomography; Journal of Biomedical Optics; 15(1); pp. (011104-1)-(011104-8); Jan.-Feb. 2010.
Wang et al.; Common-path endoscopic Fourier domain OCT with a reference Michelson interferometer; Proceedings of the SPIE; vol. 7566; p. 75660L-75660L-7; Jan. 2010.
Wikipedia; Hinge; 4 pages; retrieved from the internet (https://en.wikipedia.org/w/index.php?title=Hinge&oldid=479569345) on Jun. 9, 2021.
Smith et al.; U.S. Appl. No. 17/189,123 entitled "Optical pressure sensor assembly," filed Mar. 1, 2021.
Kankaria; U.S. Appl. No. 17/209,162 entitled "Optical coherence tomography with graded index fiber for biological imaging," filed Mar. 22, 2021.
Newhauser et al.; U.S. Appl. No. 17/209,168 entitled "Occlusion-crossing devices," filed Mar. 22, 2021.
Patel et al.; U.S. Appl. No. 17/347,419 entitled "Micro-molded anamorphic reflector lens for image guided therapeutic/diagnostic catheters," filed Jun. 14, 2021.
Tachibana et al.; U.S. Appl. No. 17/645,722 entitled "Atherectomy catheter drive assemblies," filed Dec. 22, 2021.
Gupta et al.; U.S. Appl. No. 17/445,648 entitled "Tissue collection device for catheter," filed Aug. 23, 2021.
Simpson et al.; U.S. Appl. No. 17/449,867 entitled "Occlusion-crossing devices, imaging, and atherectomy devices," filed Oct. 4, 2021.
Spencer et al.; U.S. Appl. No. 17/449,895 entitled "Occlusion-crossing devices, atherectomy devices, and imaging," filed Oct. 4, 2021.
Patel et al.; U.S. Appl. No. 17/450,658 entitled "High speed chronic total occlusion crossing devices," filed Oct. 12, 2021.
Patel et al.; U.S. Appl. No. 17/816,673 entitled "Atherectomy catheter with serrated cutter," filed Aug. 1, 2022.
Patel et al.; U.S. Appl. No. 18/183,432 entitled "Micro-molded anamorphic reflector lens for image guided therapeutic/diagnostic catheters," filed Mar. 14, 2023.

* cited by examiner

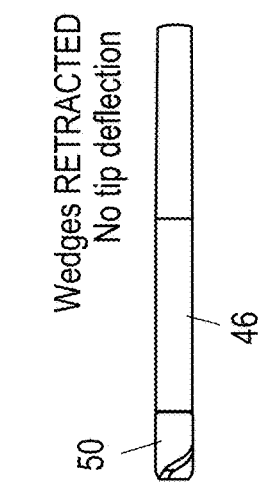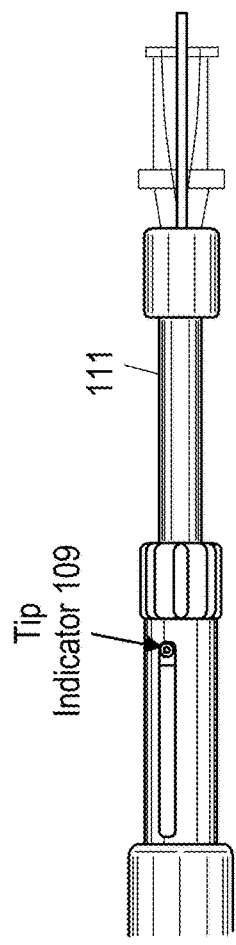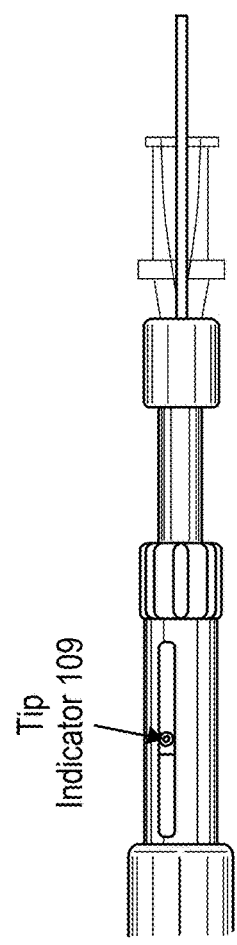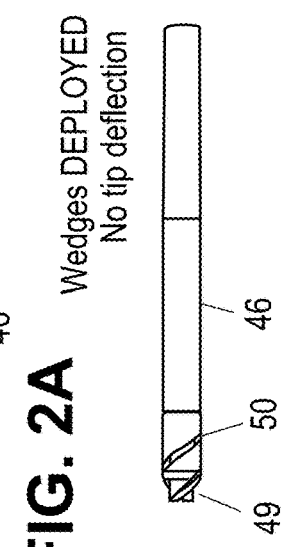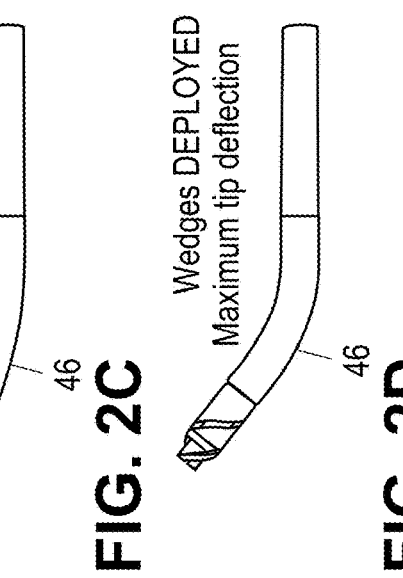

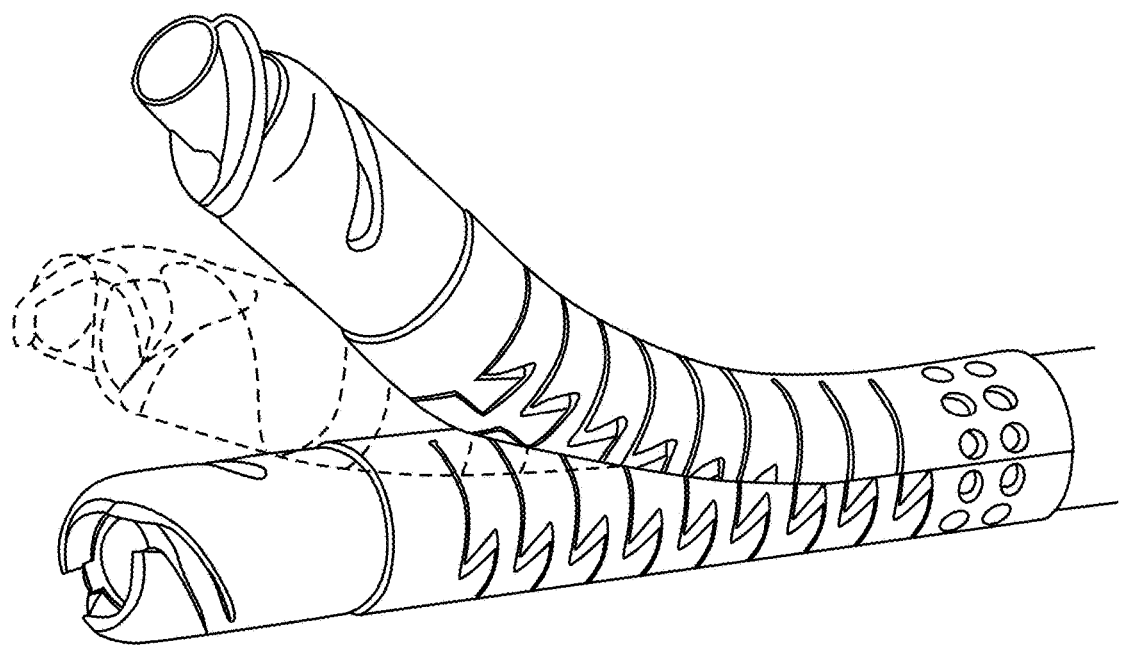
FIG. 3
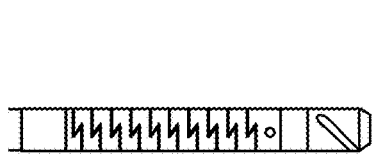  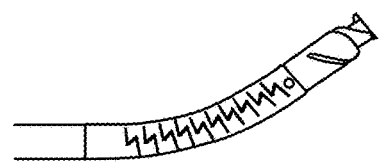
FIG. 4A  FIG. 4B  FIG. 4C

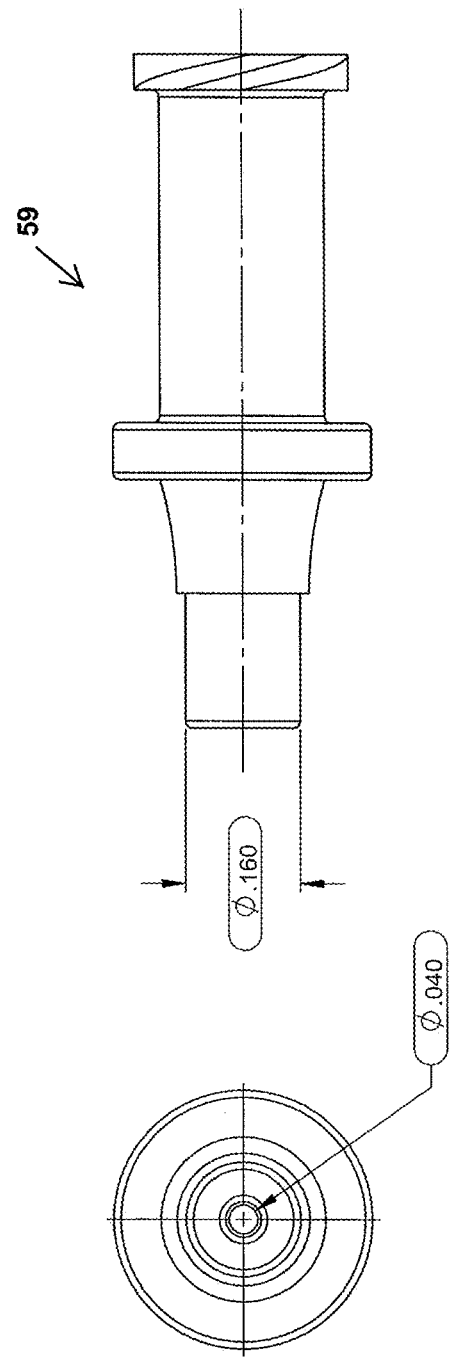
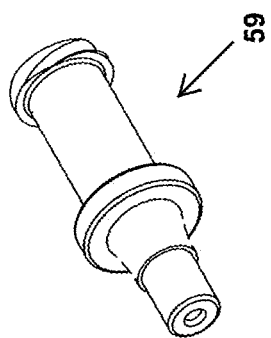
FIG. 10A
FIG. 10B
FIG. 10C

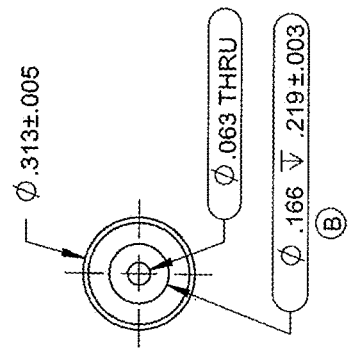
FIG. 11C
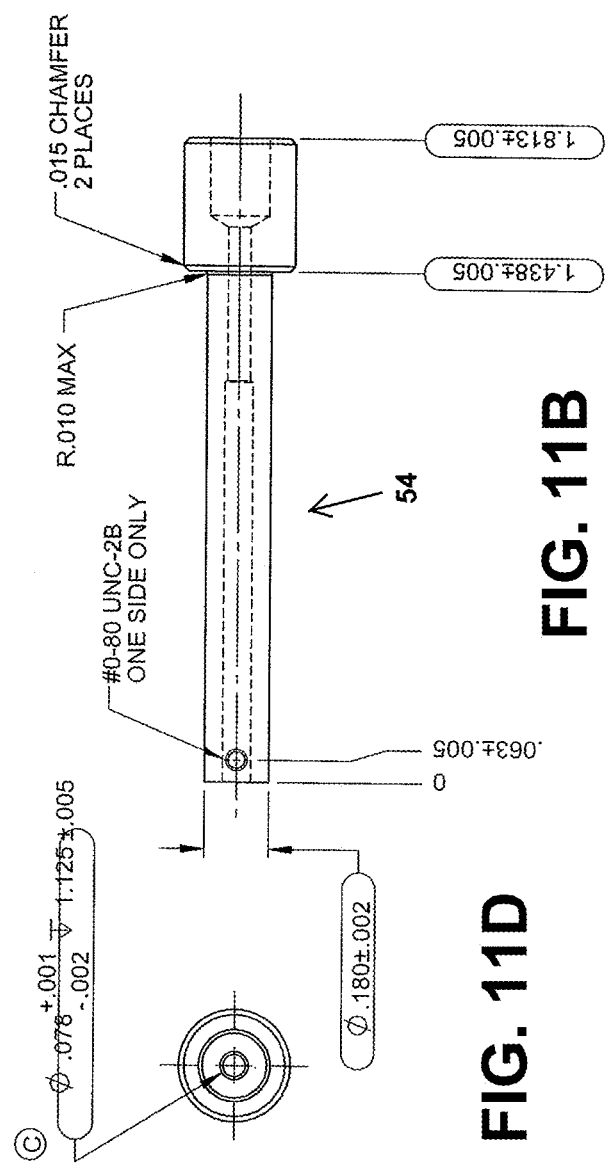
FIG. 11B
FIG. 11D

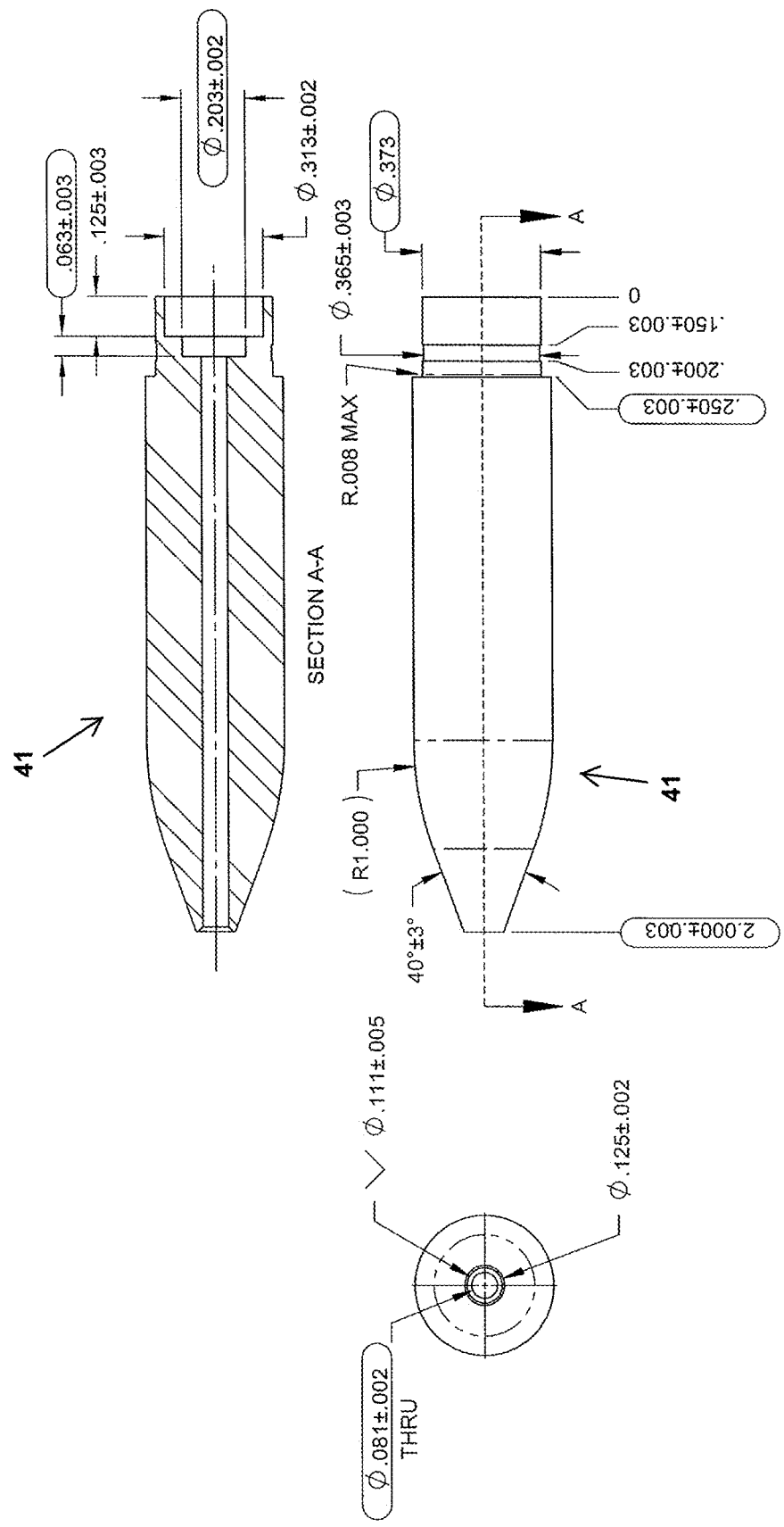

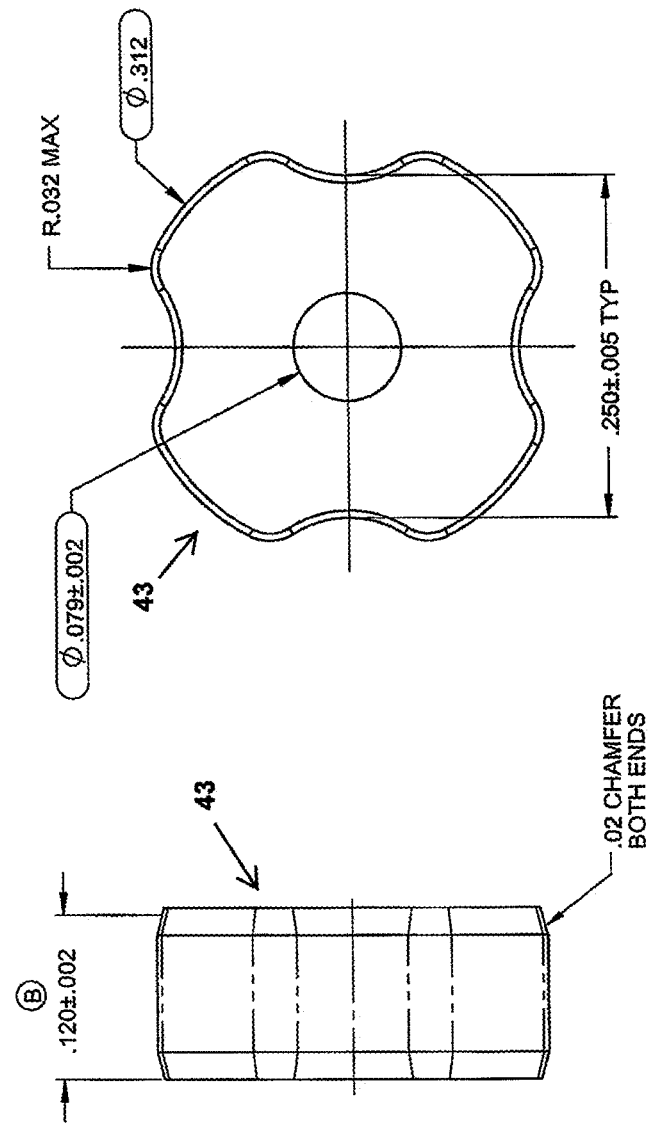
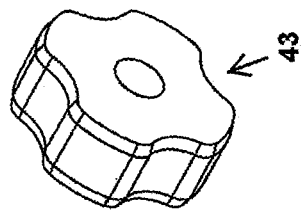
FIG. 20A
FIG. 20B
FIG. 20C

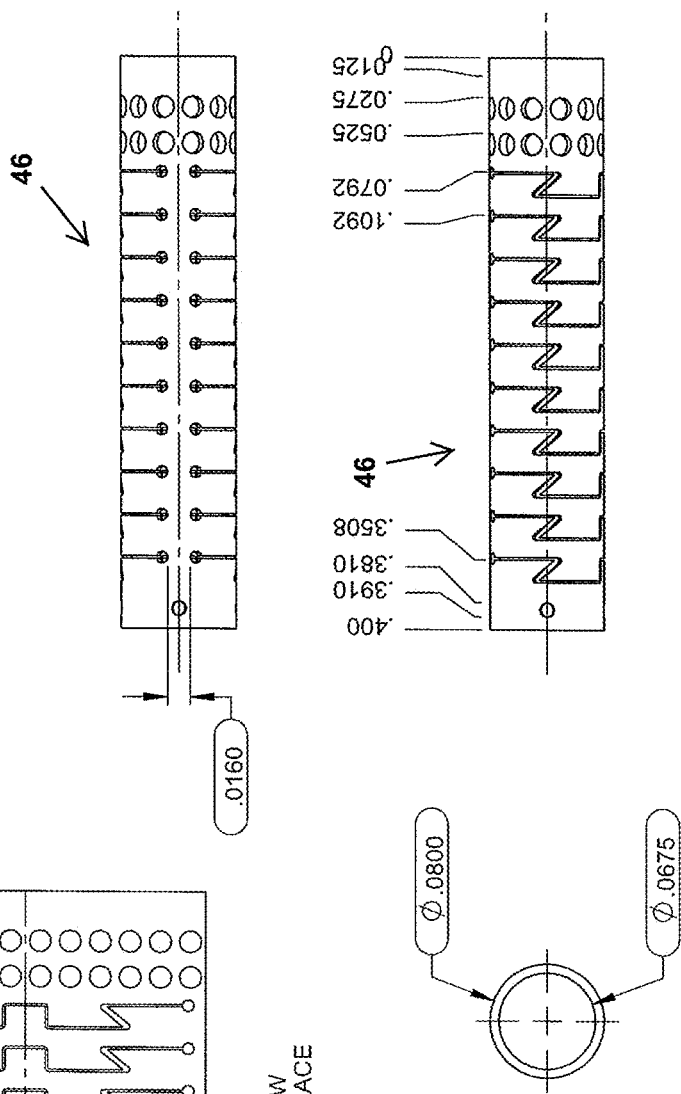
FIG. 23A
FIG. 23B
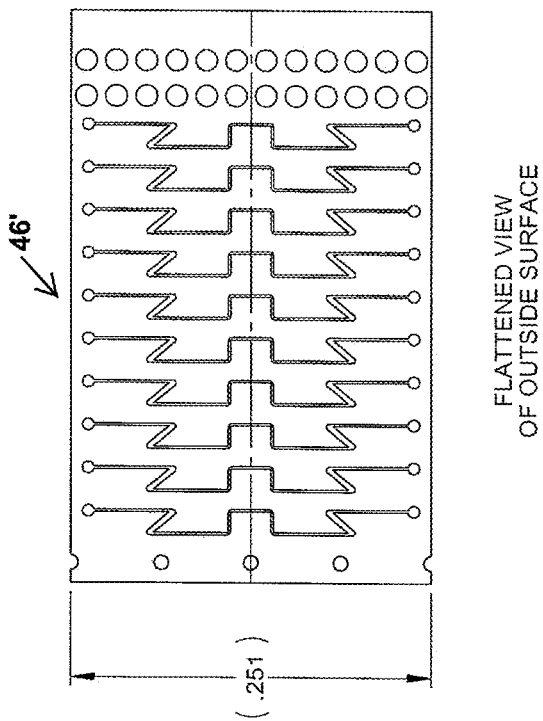
FIG. 23C
FIG. 23D

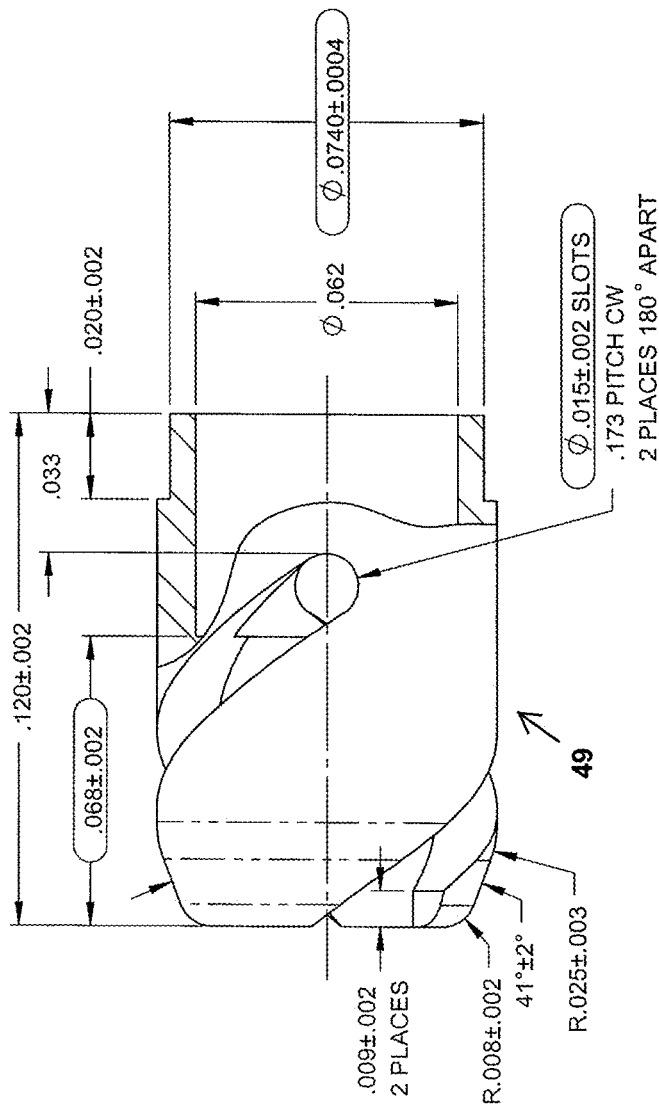
FIG. 27B
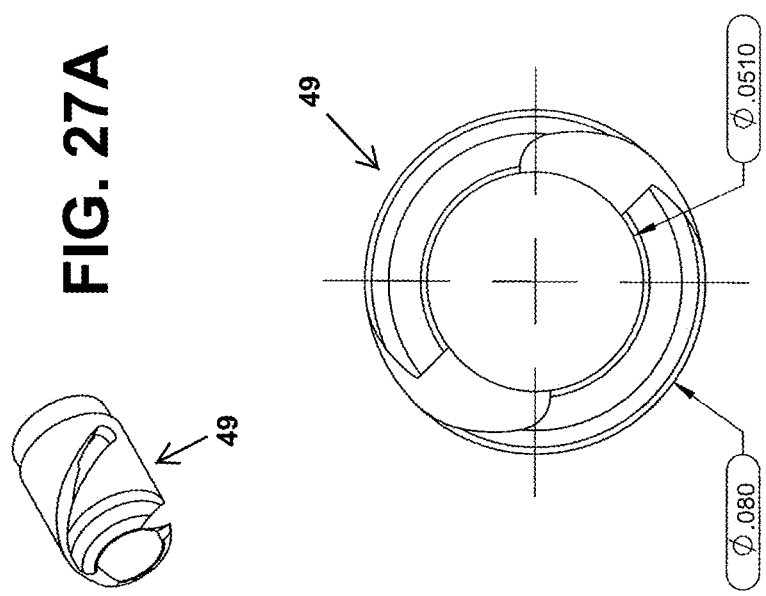
FIG. 27A
FIG. 27C

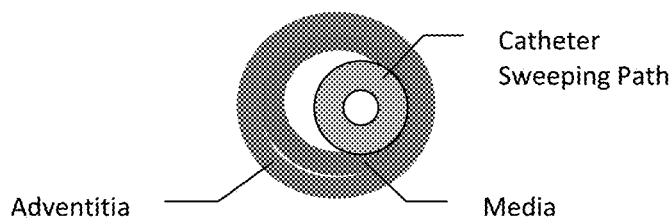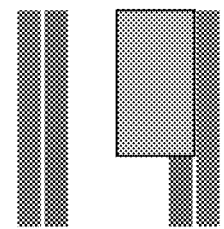
FIG. 31A     FIG. 31B
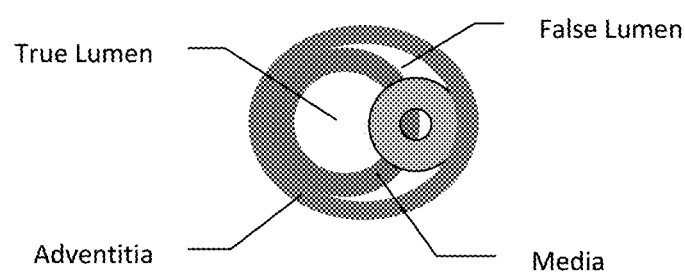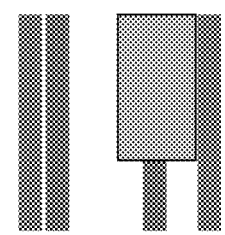
FIG. 32A     FIG. 32B

GUIDEWIRE POSITIONING CATHETER

CROSS REFERENCE TO RELATED APPLICATIONS

This patent application is a continuation of U.S. patent application Ser. No. 15/480,238, filed on Apr. 5, 2017, titled "GUIDEWIRE POSITIONING CATHETER," now U.S. Pat. No. 11,076,773, which is a continuation of U.S. patent application Ser. No. 13/929,579, filed on Jun. 27, 2013, titled "GUIDEWIRE POSITIONING CATHETER," now U.S. Pat. No. 9,642,646, which is a continuation of U.S. patent application Ser. No. 12/689,748, filed on Jan. 19, 2010, titled "GUIDEWIRE POSITIONING CATHETER," now U.S. Pat. No. 8,696,695, which claims priority to U.S. Provisional Patent Applications: 61/173,542, filed on Apr. 28, 2009, titled "GUIDEWIRE SUPPORT CATHETER," and 61/233,093, filed on Aug. 11, 2009, also titled "GUIDEWIRE SUPPORT CATHETER," each of which is herein incorporated by reference in its entirety for all purposes.

This application may be related to U.S. patent application Ser. No. 12/108,433, titled "Catheter System and Method for Boring through Blocked Vascular Passages," filed Apr. 23, 2008, now U.S. Pat. No. 8,062,316 and U.S. patent application Ser. No. 12/272,697, titled "Dual-tip Catheter System for Boring through Blocked Vascular Passages," filed Nov. 17, 2008, Publication No. US-2010-0125253-A1, now abandoned. Both of these applications are herein incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD OF THE INVENTION

Described herein are guidewire placement and support catheters that may be used to place a guidewire within an occluded lumen. In particular, described herein are guidewire placement and support catheters having a rotating, cutting and/or bending distal end region that may be used to position a guidewire through an occluded lumen of a vessel, including for treatment of chronic total occlusions.

BACKGROUND OF THE INVENTION

Guidewire placement is a critical step in many medical procedures, particularly in minimally invasive procedures and treatment of vascular diseases. For example, a number of vascular diseases, such as coronary artery disease and peripheral vascular disease, are caused by the build-up of fatty atherosclerotic deposits (plaque) in the arteries, which limit blood flow to the tissues that are supplied by that particular artery. Disorders caused by occluded body vessels, including coronary artery disease (CAD) and peripheral artery disease (PAD) may be debilitating and life-threatening. Chronic Total Occlusion (CTO) can result in limb gangrene, requiring amputation, and may lead to other complications and eventually death. Increasingly, treatment of such blockages may include angioplasty or atherectomy procedures in which a guidewire, often via a catheter, is inserted into the diseased artery and threaded to the blocked region. There the blockage may be either squeezed into a more open position, for example, by pressure from an inflated catheter balloon (e.g., balloon angioplasty), and/or the blocked region may be held open by a stent. Alternatively a physician may use a catheter to surgically remove the plaque from the inside of the artery (e.g., an atherectomy).

Thus, placement of a guidewire completely or partially across the occlusion is often a critical, though difficult step. Devices and method for guidewire placement are expensive, complex, and all too often ineffective. A guidewire must typically be forced across or through the occlusion so that the treatment catheter may be positioned to treat the occluding plaque. The guidewire must be positioned across the plaque because the active (e.g., plaque removing or displacing) portions of most currently available catheters are usually located on the sides of the catheters. For example, stents, balloons, atherectomy cutting tools, and other active portions are usually mounted on the sides of the catheter.

However, when the artery is totally blocked by plaque, it is extremely difficult, and potentially dangerous to force the guidewire through the occlusion. An obstruction or plaque may be composed of relatively tough fibrous material, often including hard calcium deposits. Forcing a guidewire or catheter past such obstructions may cause the guidewire to exit the lumen of the vessel (e.g., artery), including causing it to enter the layers forming the artery, further damaging the tissue.

Currently available devices and methods for crossing occlusions are inadequate. For example, patents such as U.S. Pat. No. 5,556,405 to Lary, U.S. Pat. No. 6,152,938 to Curry, and U.S. Pat. No. 6,730,063 to Delaney et al. describe devices and methods for passing an occlusion that do not adequately allow placement of a guidewire across a plaque. U.S. Pat. No. 5,556,405 teaches an incisor catheter having blades that can protrude from the catheter to push outward and form linear cuts in the plaque. Control of this device is mostly limited to extending/retracting the blades, and the cutting edges may damage the tissue, particularly if the blades contact the edges of the vessel; potentially exiting the lumen of the vessel. U.S. Pat. No. 6,152,938 describes a catheter drilling device for opening a wide variety of different blocked (occluded) tubes. The device anchors the tip of the drill head against a face of the occlusion, and partially rotates the drill head using a rein attached to the drill head so that the drill head faces at an angle. The blades of the drill are only controlled in rotation and may cut even non-target tissue, also leading the tip to exit and/or damage the vessel. As one alternative, U.S. Pat. No. 6,730,063 teaches a catheter device that can chemically treat calcified vascular occlusions by delivering acidic solutions and other fluids to calcified plaque to chemically dissolving the calcified material. As in the other known methods, this chemical treatment may be difficult to control, and in particular may be difficult to prevent damage to the vessel. Commercially available devices for treating occluded vessels include those marketed by Cordis Corporation, FlowCardia Technology, Kensey Nash Corporation, and other companies. These devices suffer from the same inadequacies as described above, and have also proven to have only limited success. The best reported success rates of overcoming CTOs with prior art devices range from 56% to 75%.

In addition, many of the devices and methods for crossing an occlusion described above may still require manually forcing the guidewire through the occlusion with only minimal (or no) assistance from the devices. Finally, many of these devices may inadvertently exit the vessel, but few, if any of them, are readily re-positionable to reenter the vessel.

A large family of patents and pending application including U.S. Pat. Nos. 6,001,112, 6,454,779, 6,206,898, 7,479,147, 6,451,036, 6,482,217, 7,172,610, 7,235,088 and 6,666,874 ("Taylor patents") describe a rotatable cutter that is configured for atherectomy cutting. These devices typically include an inner rotating member (that may extend from a fixed housing at the distal end of the device). The device may be guided by a guidewire, and may include a vacuum source to remove cut material. However, these devices are not adapted to self-center. In addition, these blades are typically side-cutting, meaning that the cutting typically occurs at the sides, where the rotating blade may interact with a (typically fixed) complementary surface, cutting the tissue between the surfaces. Further, the distal rotating cutting head is smaller than the diameter of the rest of the elongate distal portion of the device.

Thus, there remains a need for guidewire positioning devices that can effectively traverse occluded vessels, and particularly chronically occluded vessels. Such devices would enable positioning of a guidewire and therefore enable positioning of stents and other devices to be more successfully used in high occlusion situations, leading to improved patient outcomes and a reduction in patient morbidity and mortality.

SUMMARY OF THE INVENTION

Described herein are guidewire positioning and support devices, method for using them, method of treating a subject using them, and systems including such guidewire positioning and support devices.

These devices typically include an active distal tip region that is rotatable and may include one or more wedges that may be extended from the rotatable distal tip. In some variations the distal end of the device may be steerable, and may be steered while still rotating the distal end of the device. The wedges may be fully or partially retracted into distal housing. Both the distal housing and the wedges may rotate. The wedges (which may be sharp blades or may be blunt) can be continuously extended from the distal housing and locked in any position (extended, partially extended or retracted) and rotated clockwise and/or counterclockwise while locked in a retracted, extended or partially extended position. The distal region of the device may also be controllable steered from the proximal end of the device. For example, the distal region of the device may be deflected. The bending distal region may be located immediately proximal to the rotatable distal tip. The device is typically elongate, and includes at least one lumen extending along the length (e.g., a central lumen) through which a guidewire may be passed. The lumen (or a separate lumen) may also be used to pass a material such as a contrast dye, saline, an imaging device, etc. The proximal end of the device typically includes a handle region that may be used to control the distal end. For example, the device may include a rotation control, a wedge extension control and/or a steering control. In some variations these controls may be combined into one or more controls or these functions may be distributed or divided between different controls. Any appropriate control may be used, including slides, knobs, dials, buttons, levers, switches, etc. In some variations the controls may be automated or computer-controlled. In some variations a driver (e.g., motor, mechanical driver, etc.) may be used to drive the controls. For example, rotation of the distal tip region may be driven by a motor, and may be geared or otherwise controlled. The rotation may be manually or automatically controlled.

In some variations, described in greater detail below, rather than an extendable wedge (or wedges) and a housing, the rotatable distal tip may a single integrated wedge having a protective surface that prevents cutting of tissue when rotated in a reverse direction, while allowing cutting of tissue when rotating in the reverse direction.

The wedges at the distal end may be referred to as a blade or blades, even though they may be substantially blunt. In some variations the wedges are configured so that they are forward-cutting, but not side-cutting. This means that they may include a forward-facing cutting edge, and the more lateral edges may be blunted or less sharp. In some variations the rotating distal tip includes only a single wedge, rather than multiple wedges. The wedge (blade) may be helically arranged at the distal tip. In many variations (including those illustrated below), the rotating distal tip including the wedge(s) had a diameter that is equal to (or greater than) the diameter of the rest of the elongate body (including the regions more proximal to the distal end of the device.

In some variations, the rotating distal end comprises three or more wedges that are radially separated around the tip region (e.g., spaced equally apart radially). It may be advantageous to have three or more wedges spaced around the tip, which may improve centering of the device, as described herein.

In operation, many of the devices described herein are self-centering within the lumen of the vessel. The self-centering property of the device arises from the configuration of the distal tip as well as the rotational properties of the device. In particular, as mentioned, the wedges may be blunt, or laterally blunt (having only a forward-cutting face). Further, both the wedges at the rotating distal portion and the housing into which the wedges may be extended or retracted may rotate. Finally, the diameter of the rotating distal end (including the wedges) may be at least equal to the diameter of the more proximal regions of the elongate body of the device which may also allow self-centering within the lumen of a vessel.

In general, the guidewire positioning and support catheter devices described herein may be referred to as "guidewire support catheters," "guidewire positioning catheters," "guidewire steering catheters," "steerable rotating wedge" catheters, or the like. For simplicity, these guidewire positioning and support catheters may be referred to as merely "the devices" or "the catheter devices".

The guidewire positioning and support devices described herein may be configured as single-use, over-the-wire device, devices. For example, the device may be compatible other guidewires of standard sizes used in minimally invasive procedures. The outer diameter of the elongate device (including the distal end region) may fit within a 7 F sheath. The devices may be used with any appropriate guidewire, including steerable guidewires. For example, the guidewire may be a 0.035" guidewire. These devices may generally be described as "steering" a guidewire, although they may be used with a guidewire within the catheter, or the guidewire may be positioned within the device after the catheter has been positioned.

In general, these devices provide support and guidance for positioning a guidewire across an occlusion. As described herein, the devices may support probing and exchange of an assortment of guidewires, by traversing an occluding in a vessel. In addition, the devices described herein may be used to deliver contrast. The internal lumen which may be used by the guidewire may also be used for local dye injections without removing the device from the vessel.

As described in greater detail below, in operation the steerable (deflecting) distal end and the rotating distal tip allow the device to be passed through an occlusion such as a plaque occluding a blood vessel (or artery) without requiring removal of the plaque. Thus, the device may be used to bluntly form a pathway through a plaque using the retractable/extendable rotating wedges at the distal tip, or simply using the rotating distal tip alone. The exposable wedge(s) at the distal tip may also allow for helical AND blunt microdissection. In some variations, the wedges at the distal tip are sharp (e.g., cutting or knife-edged), while in other variations the wedges are substantially blunt. The wedges are typically curved around or along the longitudinal axis of the distal tip. For example, a wedge may extend helically around the distal tip end of the device (when extended).

In variations in which the rotatable distal tip includes one or more separate wedge and housing, the extension of the wedge from the distal housing may be limited. For example, the wedges may be prevented from extending fully out of the distal housing, thereby preventing material (such as a plaque or tissue) from getting caught between the wedges and the housing.

The steerable distal end region may be steerable in any appropriate manner. In particular, the distal end region may be steerable by defecting in one direction (e.g., 'down') or in more than one direction (e.g., down/up, right/left, etc.). The degree of deflection may also be controlled. In some variations, the tip may be deflected a maximum of 10 degrees, 15 degrees, 20 degrees, 25 degrees, 30 degrees, 45 degrees, 60 degrees, 90 degrees, or any angle there between. In some variations the distal end region of the device is pre-biased to be straight. Therefore the straight configuration of the distal tip may be restored once the deflection (controlled at the proximal end) is restored. In addition to be deflectable, in some variations the distal end of the device is flexible. The end region may include the tip (e.g., the rotating tip) or it may include the region immediately proximal to the tip. In general the "tip region" refers to the rotatable tip region at the distal end.

Deflection or steering of the distal end may help with re-entry of the device. For example, the deflectable/steerable distal end region (which may be referred to as the "steerable tip") may allow the catheter to re-enter the true lumen of the vessel if it becomes subintimal (e.g., if it extends into the fascia or region around the vessel).

In some variations, the device may include a distal end that has exposable bilateral wedges within a bullet-shaped housing, a catheter shaft, and a proximal handle that allows manipulation of the distal end of the device (e.g., rotation, steering, etc.) and may also provide a channel for flushing of the catheter lumen. In this variation (and other variations) both the distal tip and bilateral wedges are visible through fluoroscopy, and the catheter can be delivered over-the-wire through a 7 F introducer sheath. The device also facilitates the delivery and exchange of guidewires and other therapeutic devices, such as stents, angioplasty balloons, or atherectomy catheters. It may also be used to deliver saline or contrast.

The proximal handle may act as an interface with the operator, and allows a physician to expose or retract the wedges as needed. This part of the device may include four main components: a rotator, a pin, a slider, and a luer. The operator can use the slider and rotator to manipulate the pin, which in turn controls whether the wedges are exposed or retracted. The pin acts as a locking mechanism to control the deployment of the wedges. At the end of the handle, the luer allows for flushing of the catheter with saline prior to use and serves as a portal to deliver contrast or saline to a desired area. The catheter shaft provides pushability and torque to the bilateral wedges, and serves to center the device towards the middle of a CTO. The distal tip contains the bilateral wedges within a bullet-shaped housing (FIG. 4). The housing with the wedges either retracted or exposed and rotating in a counter-clockwise direction can deliver blunt microdissection with more force than a guidewire. With the wedges deployed, and rotating in a clockwise motion, the spinning action creates helical microdissection planes to pull the catheter through the CTO lesion.

Any of the devices describe herein may include one or more of the following features, including: a steerable distal end region, a relatively short length, an elongate torque (drive) shaft) for rotating the distal tip, and reversible and retractable wedges having limited extension. The steerable distal end region is designed for and allows luminal re-entry. For example, the may be adjustable up to a 45° angle and can help orient the device.

The devices described herein may be any appropriate length, but relatively short length catheters may be particularly useful. For example, the device may be approximately 100 cm, allowing the device to reach any occlusion down to the popliteal and ease physician handling outside the body. In other variations, the device is between about 50 and 150 cm, between about 70 and 120 cm, etc.

The distal tip may be driven by an elongate drive short (or "torque shaft") that extends the length of the device. This drive shaft is typically robust, allowing increased torque precision and manipulation during the operation. Examples of this torque shaft are provided herein. F or example, the torque shaft may be made of a braided stainless steel material having a hollow lumen (forming the central lumen of the device). Rotation of the drive shaft typically drives the distal tip rotation. The drive shaft is typically flexible and connects to the rotational control at the proximal end (e.g., handle).

The extendable/retractable wedges (including the wedge element as well as the housing into which the wedges may be retracted) may include one or more features which act as safety features. For example, the (typically helical) wedges may be configured to disengage more readily if needed during operation of the device. The distal tip, including the wedges and housing, may rotate both clockwise and counterclockwise. In addition the wedges may be extended or retracted independently of the rotation. Thus, the distal end may be rotated with the wedges locked in any desired extended or retracted position. In addition the extension of the wedges may be limited to maximum extension that prevents the formation of a gap or space between the housing and the wedges between which material may be trapped. For example, the wedges may be prevented from further extension by a lock or pin that prevents the wedges from fully extending out of the housing.

The handle region at the proximal end of the device may also be adapted for handheld use. In particular, the controls at the handle region may be adapted so that the device may be manipulated by a single hand. In some variations the handle region may also include one or more indicators or displays for displaying the status of the distal end of the device. For example, the handle may include an indicator indicating the extent to which the wedges are extended from the distal tip. The indicator may be a dial, slider, or the like. The indicator may be marked or unmarked.

As mentioned, in some variations the wedge(s) may be extended to any degree (or to a maximum extension), or retracted completely. The handle, or the controller for the extension/retraction on the handle, may include a lock locking the wedges at a desired extension. The same, or a different, lock may also be included on the handle for locking the configuration/position of the distal end region that is steerable or deflectable. For example, a lock may be used to lock the distal end at a 45 degree angle.

The proximal handle may be otherwise configured to be handheld. For example, the controls may be clustered or located at one end of the handle with a gripper region at the other end. For example, the controls may be clustered at the proximal portion of the handle (allowing the distal portion of the handle to be gripped in the palm of the hand, and manipulate d by the thumb and forefinger of the right.

In general, the elongate outer sheath of the catheter is flexible, and may be coated so that it can be readily inserted into a lumen of a sheath, catheter, or directly into a body lumen. For example, the elongate outer sheath of the catheter may be formed of a braided stainless steel, a polymer, or the like. The elongate outer sheath is typically tubular, and may be coated (either or both inner and outer diameter) with a protective cover. The elongate outer sheath may be referred to as a shaft (e.g., catheter shaft), and may be coated with a lubricious material or may be formed of a smooth and/or lubricious material.

Described herein are devices, including at least one specific example of a device, including some examples in which dimensions are provided. It is to be understood that these dimensions may be varied while staying within the scope of the invention as generally described. Unless otherwise indicated, these dimensions are intended as merely illustrative, and not limiting.

As mentioned briefly above, various aspects of the devices described herein provide substantially benefits compared to other device which may be used in occluded vessels, including rotating devices. For example, the forward cutting blades may prevent cutting on the sides/walls of the lumen. This configuration may also help with self-centering, as mentioned. In addition, the device may be configured so that the diameter of the blade (e.g., wedge) region is the same as the diameter of the rest of the catheter. Thus, the diameter of the distal end having the rotatable wedge is maxed out, so that the blades are as big across as the rest of the catheter, which may allow for maximum traction in the lumen of the vessel. The diameter of the blades (the distal region including the blade or blades) may therefore be equal to the diameter of the catheter. This in turn may allow the blades to engage better with the tissue of the vessel because there is more region of the vessel (e.g., width) available for the blade to engage with.

As mentioned, the distal end region may be rotated manually. For example, the tip may be spun or rotated by rotating a control or portion of the proximal handle. Thus, the device may be used as a screwdriver or drill element that is manually turning at a slow, more controlled (e.g., continuously and manually variable) rate. This may also provide tactile feedback to the operator, who can gauge how much force is applied by the feel of the device. For example, a clinician may determine how much force to apply both to advance and to spin the blades. Compared to true "drilling" elements and augering devices, the devices described herein may be worked into the media of the vessel more readily. Rotation of the tip may be clockwise or counterclockwise. In some variations the direction of rotation determines whether the wedge(s) at the distal tip are cutting or non-cutting. The user may alter the direction of cutting at any time during the procedure, and may manually or automatically control the rate and/or direction.

In variations having blades (wedges) that are substantially blunt on the longitudinal side (e.g. the side facing the wall of the vessel), the devices may advantageously be advanced into the vessel, and may self-centered. These variations may also prevent damaging the lumen of the vessel.

In variations of the devices having a steerable distal end, the same control that allows extension (and/or rotation) of the distal end to extended/retract the wedges from the catheter/protective housing may be used to steer (e.g., bend) the distal end. By combining the steering with blade extension, the controls are simplified, allowing the device to be controlled more easily with a single activation scheme.

In addition, these devices realize previously unexpected advantages because the entire distal end, including (in some variations) the housing into which the wedges/blades may retract, rotates. The rotation of the distal protective housing may permit blunt tip movement/dissection and allows powered blunt dissection. Compared to simply advancing a blunt (non-rotating tip) through the vessel, rotating the blunt or blunted distal end (e.g., when the blades are retracted into the housing), the device may exhibit a substantial mechanical advantage, apparently allowing the device to overcome the static friction at the tip and advance across an occlusion. As mentioned above, the rotating housing also helps with self-centering and steering of the device. The ability to rotate the device in both the clockwise and counterclockwise (e.g., forward and backward) directions manually is also particularly helpful for blunt dissection. Turning the catheter tip (with blades retracted) in one direction (i.e., clockwise) allows the helical slots to engage the tissue more as the edges are rotated in the direction of the helix, rather than the opposite direction (i.e., counterclockwise) that moves it along the direction of the helix, thereby preventing or allowing less motion forward.

Finally, the devices described herein can be locked in the open/closed position while still being rotatable. For example, the devices can be locked with the wedges/blades partially extended, completely extended, and/or completely retracted. In many variations the handle includes a lock or locking control for securing the blades/wedges in a particular extension, while still allowing the entire distal end (including the blades/wedges and housing) to rotate.

Also described herein are elongate guidewire support catheter devices for positioning a guidewire across an occluded portion of a vessel including: an elongate catheter body having an outer diameter; a rotatable distal tip configured to be rotated in a forward direction to cut tissue and a reverse direction for bluntly contacting tissue without cutting; a proximal handle region including a control for rotating the distal tip in either the forward or reverse directions; and a central lumen extending through the elongate guidewire support catheter configured to pass a guidewire.

The outer diameter of the distal tip may be approximately the same as the outer diameter of the elongate catheter body.

In some variations, the device also includes a steerable distal end region configured to controllably deflect the rotatable distal tip. The rotatable tip may comprise a helical blade edge. The rotatable distal tip in some variations has a substantially smooth, curved outer surface that presents an atraumatic tissue-contacting surface when rotated in the reverse direction and that presents a sharp, tissue-cutting surface when rotated in the forward direction.

Also described herein are methods of placing a guidewire across an occlusion of the lumen of a blood vessel including the steps of: advancing a catheter having an elongate catheter body and a rotatable distal tip towards the occlusion in the lumen of the blood vessel (wherein the distal tip comprises a forward-cutting wedge having atraumatic lateral edges and a protective housing); rotating and extending the wedge of the distal tip out of the protective housing while rotating both the wedge and the protective housing (wherein the wedge and protective housing have an outer diameter at least as large as the outer diameter of the elongate catheter body); advancing the distal tip across the occlusion; and passing a guidewire through a lumen of the catheter once it has crossed at least partially through the occlusion.

The step of rotating the distal tip of the catheter may include rotating the distal tip both clockwise and counterclockwise.

The method may also include steering the distal tip. The step of steering may include manipulating a control on the handle of the catheter to bend the distal end of the device.

Also described herein are methods of placing a guidewire across an occlusion of the lumen of a blood vessel including: advancing a catheter having an elongate catheter body and a rotatable distal tip towards the occlusion in the lumen of the blood vessel; rotating the distal tip relative to the elongate body in a forward direction to cut tissue rotating the distal tip relative to the elongate body in a reverse direction to bluntly contacting tissue without cutting; advancing the distal tip across the occlusion; and passing a guidewire through a lumen of the catheter once it has crossed at least partially through the occlusion.

The step of rotating the distal tip may comprise manually rotating the distal tip. The method may also include steering the distal tip. As mentioned, the step of steering may include manipulating a control on the handle of the catheter to bend the distal end of the device.

BRIEF DESCRIPTION OF THE DRAWINGS

FIGS. 2A-2D illustrate operation of one variation of a guidewire positioning and support catheter device.

FIG. 3 illustrates steering of the distal end region of a guidewire positioning and support catheter device.

FIGS. 4A-4C illustrate sequential extension of the wedge portion(s) of a guidewire positioning and support catheter device and deflection of the distal end of the device.

FIGS. 10A-10C show side perspective, side and end views, respectively, of the luer fitting at the proximal end region of one variation of a guidewire positioning and support catheter device.

FIGS. 11A-11D show side perspective, side, end and front views, respectively, of one variation of a slider component of a handle of a guidewire positioning and support catheter device.

FIGS. 17A-17D show side perspective, side, cross-sectional, and end views, respectively, of a handle body portion of a handle for a guidewire positioning and support catheter device.

FIGS. 20A-20D show side perspective, front and side views, respectively, of an o-ring cap portion of a handle for a guidewire positioning and support catheter device.

FIGS. 23A-23C show first and second side perspective views, and an end view, respectively, of a steerable distal end portion of a guidewire positioning and support catheter device as described in one variation herein. FIG. 23D shows the steerable (or flexible) distal end of FIGS. 23A-23C projected flat (e.g., "unrolled") so that the cut pattern is apparent.

FIGS. 27A-27C show side perspective, side and end views, respectively, of a distal housing for a rotatable distal tip portion of a guidewire positioning and support catheter device as described in one variation herein.

FIG. 31A shows a cross-section through a region of a vessel including a guidewire positioning device as described herein.

FIG. 31B is a partial longitudinal view of the same region of FIG. 31A.

FIG. 32A shows an alternative view of a cross-section through a region of a vessel including a guidewire positioning device.

FIG. 32B is a partial longitudinal view of the same region of FIG. 32A.

FIGS. 41A and 41D show side perspective views. FIG. 41B shows an end view. FIG. 41C shows a side view.

DETAILED DESCRIPTION OF THE INVENTION

Figure 1:
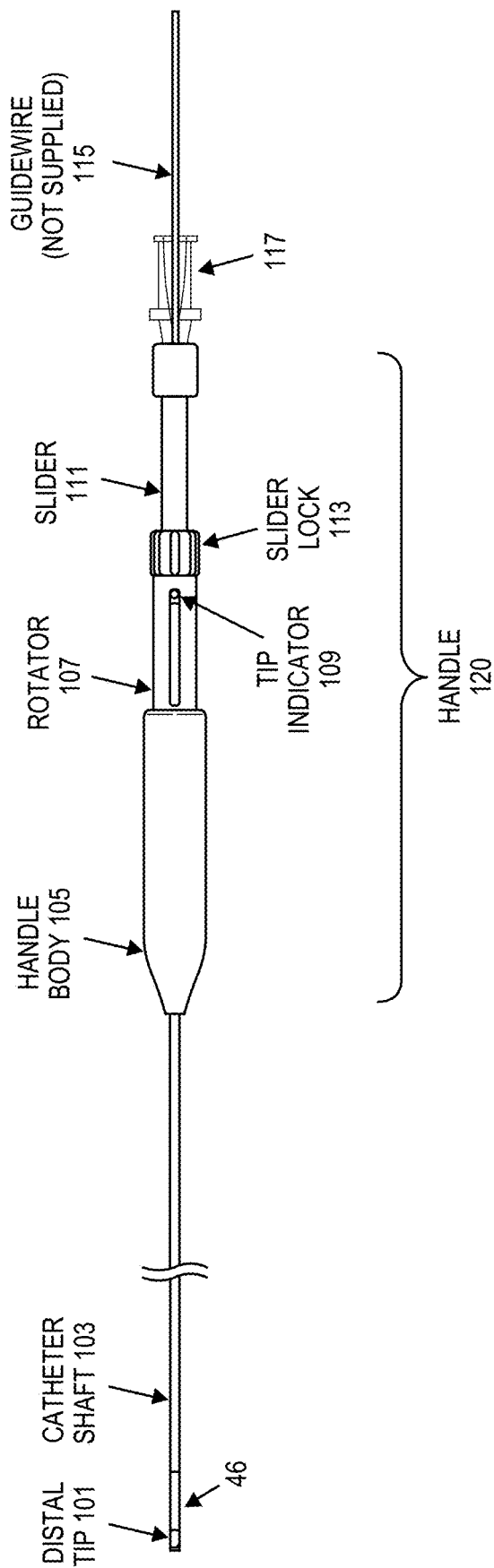
FIG. 1 is a perspective view of one variation of a guidewire positioning and support catheter devices as described herein.

FIG. 1 illustrates one variation of a guidewire positioning and support catheter having a rotatable distal end with extendable/retractable wedges. This device may be used to position (e.g., providing a channel for) a guidewire or for traversing an occlusion in a vessel, particularly for traversing complete occlusions. This device may be used to support steerable guidewires (and may be used to guide them) in accessing discrete regions of the peripheral vasculature. It may be used to facilitate placement and exchange of guidewires and other interventional devices. It may also be used to deliver saline or contrast.

One example of such a guidewire support catheter is provided below, although other variations are contemplated. In general, these devices include a rotatable distal tip. The distal tip may be rotated manually (by operation of a control on the proximal handle). In some variations both counter-clockwise and clockwise rotation is possible. The devices may include one or more extendable wedges that may be extended from or retracted into a distal housing that is atraumatic (e.g., smooth, non-sharp). The wedges may be blades, or they may include one or more sharp regions, or they may be dull. The wedges may be extended continuously, so that the user can operate a control on the proximal handle to extend and/or retract the wedges. The wedge or wedges may extend laterally from the region along the length of the tip. For example, the wedges may extend helically at least partially around the distal tip. In some variations a single wedge (which may be a single helical wedge) extends from the tip of the distal end. Multiple wedges may extend from the distal tip. In some variations two bilateral wedges may extend from the distal tip. The rotation of the wedges may be independent of the extension of the distal tip. For example, the distal tip may be rotated even with the wedges retracted or with the wedges all or completely extended.

The devices described herein may also include a steerable distal end region. The steerable distal end region may be steerable in one or more directions. For example, the steerable distal tip maybe displaced in one direction (e.g., bent in one direction). In some variations, the steerable distal end region is coordinated with the extension of the wedge or wedges from the distal tip. For example the steerable distal end region may be configured to bend in one or more direction using the same actuator that extends the wedge from the rotatable distal tip. This configuration may reduce or eliminate the need for an additional bending/steering mechanism (e.g., tendon wires or the like) to traverse the elongate body of the catheter. In other variations, including those allow for steering in multiple directions the steering of the distal end region may be independent of the extension of the wedge from the distal tip. For example, one or more control wires (e.g., tendons), hydraulic or pressure lines may be use to control steering (bending) of the distal end region.

FIG. 1 shows one variation of a guidewire support catheter. This example includes a 6 F catheter (outer) sheath 103 and is a 0.035" guidewire compatible over-the-wire device. An exemplary guidewire 115 is shown inserted in the proximal end of the device handle 120. Thus, a system may include a guidewire, although a guidewire does not have to be included as part of the device. The guidewire support catheters described herein may include a catheter shaft 103 with handle assembly 120 at the proximal end and an atraumatic distal tip 101. A locking luer connecter 117 at the proximal end provides entry to a lumen that supports and facilitates movement of a guidewire 115. The catheter may be sterilized.

The blunt distal tip 101 houses one or more deployable spiral wedges (not visible in FIG. 1) and allows atraumatic advancement of the catheter through the vasculature. At the proximal end of the catheter, manipulation of a control (e.g., slider 111) controls the deployment and retraction of the wedges and deflection of the flexible distal tip 101. Advancing the slider 111 in the distal direction deploys the wedges from the distal tip, and pulling the slider to its furthest proximal position retracts the wedges inside the distal tip 101. A tip indicator 109 moves in conjunction with longitudinal movement of the slider and provides information about wedge deployment and the amount of deflection at the distal tip (described in more detail below for FIGS. 2A-2D). In the variation illustrated in FIGS. 1-2D, at the tip indicator's 109 most proximal location, the wedges are in the retracted position. If the tip indicator 109 resides in its mid-point location, the wedges are fully deployed. As the slider 111 is advanced distally from this mid-point and the tip indicator 109 moves towards its furthest proximal location, the distal tip 101 deflects at an increasing angle (see FIGS. 2C and 2D). The flexing of the distal tip 101 is visible under fluoroscopic guidance.

The handle assembly 120 typically consists of a handle body 105, a rotator 107, a tip indicator 109, a slider 111, a slider lock 113, and a luer 117. The handle body 120 controls rotational orientation of the catheter, including the flexible distal tip. The rotator 107 controls the rotational movement to the distal tip independent of the catheter orientation. Rotational movement of the distal tip 101 can be achieved either with wedges deployed or retracted. As referenced above, the slider 111 can move through the rotator in a longitudinal direction to control wedge deployment/retraction and the amount of tip deflection. The slider lock 113 restricts the slider movement. The slider lock 113 can be engaged by turning it in the clockwise direction until tight, and can be disengaged by counterclockwise rotation. The Luer is provided to facilitate fluid flush and the entry/exit of the guidewire. This port also acts as an entry port for the guidewire.

FIGS. 2A-2D illustrate extension/retraction of the wedge (e.g., "blade") elements from the distal tip of the device. As shown in FIGS. 2A and 2B, moving the slider 111 portion of the handle distally (as indicated by the movement of the tip indicator 109), extends the wedges 49 from the retracted position shown in FIG. 2A, to a deployed condition, shown in FIG. 2B. When the slider is about halfway along the indicator, the wedges are fully deployed. In this example, the wedges do not extend out of the protective housing at the distal tip 50. Moving the slider further distally (as shown in FIGS. 2C and 2D) acts to deflect (steer or bend) the distal end region of the device.

In the variation shown in FIGS. 1-2D, the distal end region includes a laser-cut tubular region (scaffold 46) that is pre-biased in a straight configuration, but may be bent or flexed to deflect at an angle from the straight configuration, as shown in FIGS. 2C and 2D. The inner shaft (a torque shaft or drive shaft) in this example is connected to the slider on the handle, and is slideable within the catheter relative to the distal housing 50. Thus, the drive shaft (not visible in this figure) is connected to the wedges 49 at the distal tip, and sliding the slider causes the drive shaft to advance the distal tip until it is fully deployed, as shown in FIG. 2B. Further advancing of the slider, as illustrated in FIGS. 2C and 2D, applies a force at the distal end of the device that result in bending of the tubular region 46. In this example, the cuts in the tubular region allow the region 46 to flex or bend in a predictable region. One side of the tubular region 46 is not cut, and acts as a living hinge region that may bend as the spacing between the cuts of the cut region expands. As illustrate below, these cuts may be spaced and angled to limit the ability of the tubular region 46 to bend beyond a certain point (e.g., to form an angle of less than some predetermined amount, such as 30 degrees, 40 degrees, 45 degrees, 50 degrees, 60 degrees, etc.). Thus, in FIG. 2C the distal end region is shown with the wedges deployed at a minimal tip deflection (also indicated by the slider tip indicator 109 slightly proximal from the distal end of the indicator window). In FIG. 2D the slider is fully deployed distally and the distal end of the device is bent to the maximum tip deflection, with the wedges extended.

Although the control of the extension/retraction of the wedges and the deflection or steering of the distal tip are conjoined in this example, which may simplify the one-handed control of the catheter and allow the control of extension/retraction and deflection using a single drive shaft, in other variations these controls may be separated, and separate drive shafts may be used. In addition, the deflecting/bending tubular region 46, which may be referred to as the deflecting, bending or hinged region, is configured to bend by the application of a longitudinal pushing force that is applied from the drive shaft in this example. Because this deflecting region is 'hinged' on one side in this example, a symmetric (or even asymmetric) force applied across the region causes the region to bend against the hinge. The tubular region 46 in this example may be made of any appropriate material, for example, metal (stainless steel, shape memory alloys such as Nitinol, or the like), polymers (plastics, elastomers, etc.) or the like. It may be helpful if the region is configured to include a restoring force and restores itself to the original (straight) shape when the distal force is removed.

FIGS. 3 and 4A-4C illustrate steering of the distal end of a catheter as just discussed. For example, in FIG. 3 the 'hinge' portion of the tubular region extends laterally along the top of the device shown. The hinge in this example is simply a narrow band that is solid, while the rest of the circumference of the region includes a plurality of approximately transverse (i.e., transverse to the longitudinal length of the catheter) cuts. The cuts in this case include regions that double back on themselves to form a zig-zag pattern. This pattern (shown in detail in FIGS. 23A-23D) effectively limits the bending of the region since, for any given spacing between the cuts, the opposite walls of the cuts in the doubled-back region will contact each other, preventing further bending. The hinged region shown in FIGS. 3-4C is formed by laser-cut stainless steel, however other materials, and method of cutting them, may be used, as mentioned.

Figure 5:
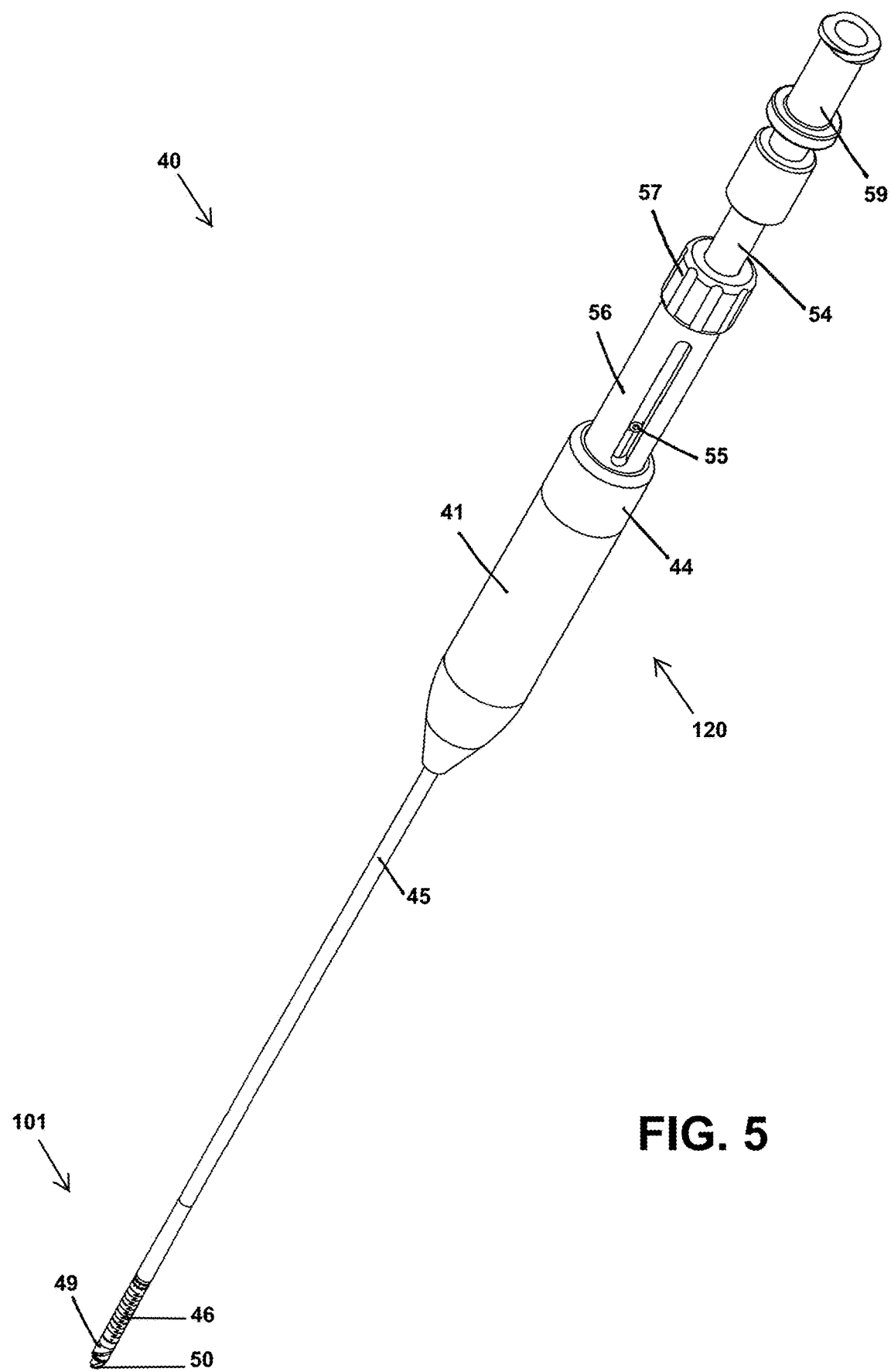
FIG. 5 is a side perspective view of another variation of a guidewire positioning and support catheter device.

FIG. 5 shows a side-perspective view of one example of a catheter 40 as described herein. In this variation, the catheter includes a distal end region 101 having a flexible or deflection region 46 and a rotatable tip region consisting of a protective housing 49 and an extendable/retractable wedged region 50. The distal end region 101 is connected to the proximal handle region 120 by an elongate catheter 45. This catheter includes an outer flexible catheter body 45, and one or more inner members, such as an inner drive member (not visible in FIG. 5) that can drive rotation of the distal tip. This catheter also includes a central passageway (not visible) that opens at the proximal and distal ends.

The handle region 210 includes a handle body 41 that is connected to a handle body cap 44 which interfaces with a rotator portion 56. The rotator 56 partially covers a slider 54. The rotator portion 56 may be rotated; this rotation is translated (e.g., via a drive shaft) into rotation of the distal tip. The slider may move distally or proximally within the handle 120. A window in the slider shows a position indicator (set screw 55) that indicates the longitudinal position of the slider, and therefore indicates the extension/retraction state of the wedges at the distal tip. Sliding the slider distally extends the wedges from the housing and may also deflect or steer the device, as just described. The proximal end of the device includes a luer fitting region which may be used to connect to the central lumen of the device (e.g., for applying contrast, saline, etc.). The luer region may include a threaded or lockable region. The luer region may also include a flanged or funnel-shaped opening to help assist in threading a guidewire into the catheter.

Figure 6:
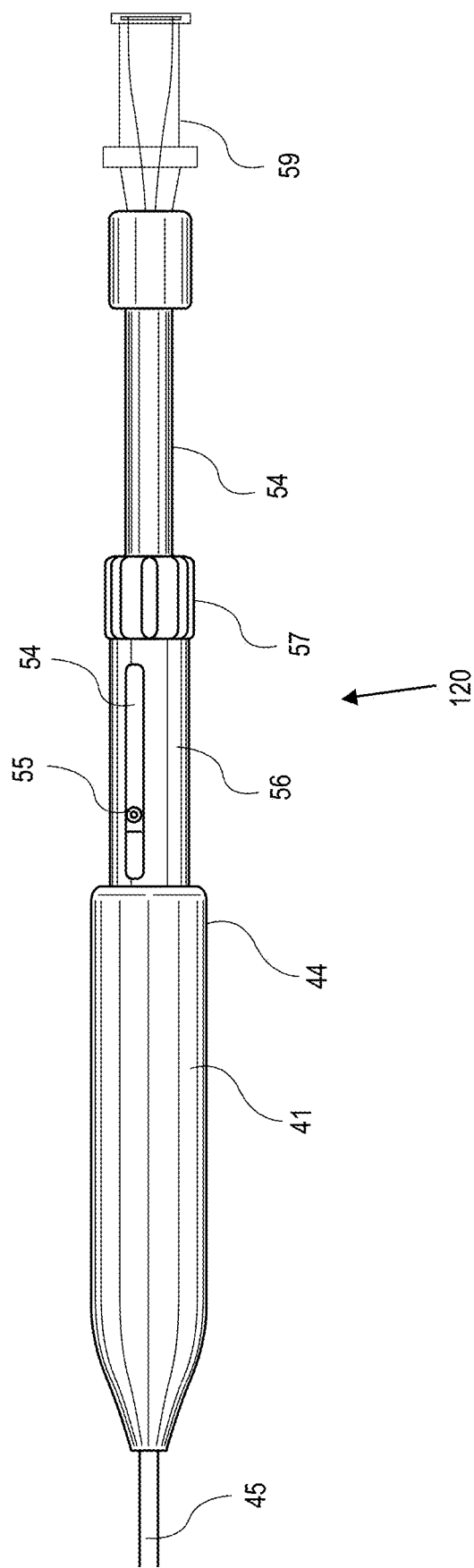
FIG. 6 is a side perspective view of the proximal handle region of the guidewire positioning and support catheter device shown in FIG. 5.

FIG. 6 shows a close-up perspective view of just the proximal handle region 120 of the device shown in FIG. 5.

Figure 7:
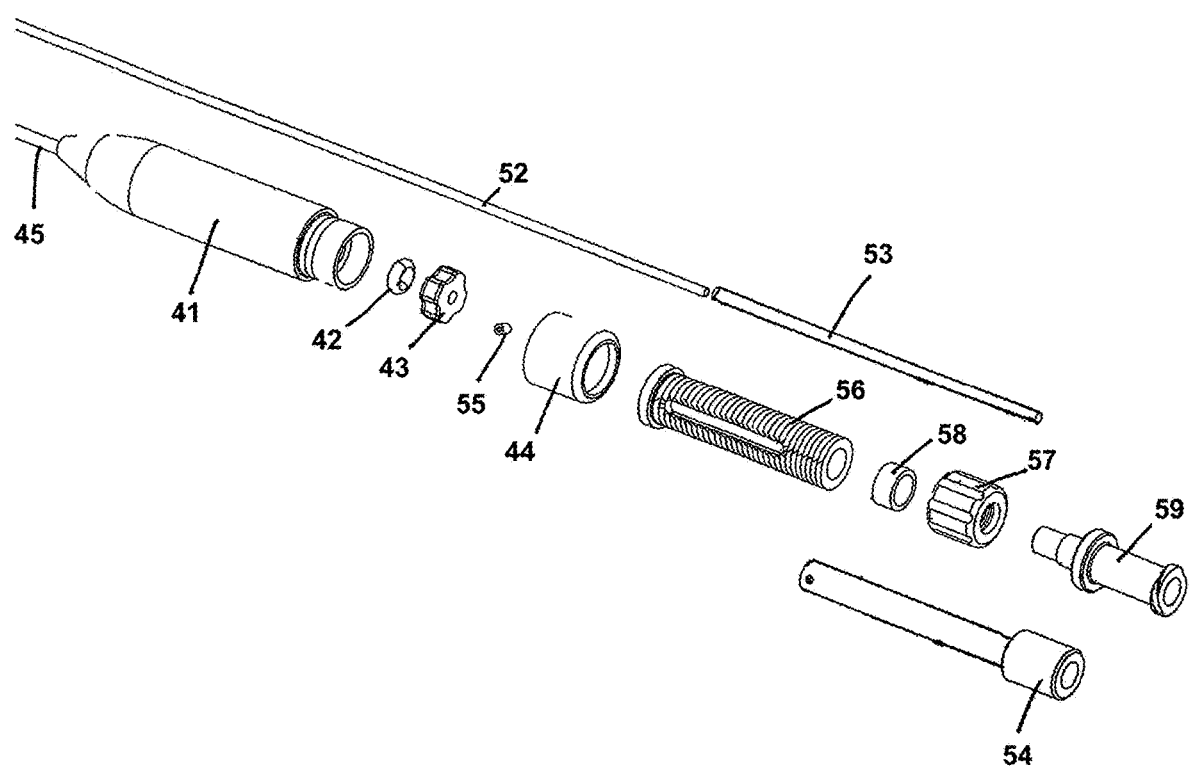
FIG. 7 is an exploded view of the proximal handle region shown in FIG. 6.

FIG. 7 is an exploded view of the handle region 120 of FIGS. 5 and 6, indicating all of the component parts, including internal elements that may be included. For example, the device may include an inner drive catheter 52 connected to both the rotator 56 and the slider 54. In this example, the inner drive catheter is a braided stainless steel catheter that is connected to a more rigid (e.g., stainless steel) tube 53 at the proximal end. The rigid tube 53 may help provide a fluid seal against one or more sealing elements, such as O-rings 42 and slider seals 58. These seals may help isolate the components of the device. Without seals between the drive shaft 52 and the outer catheter 45, fluid (e.g., blood, etc.) may leak from the body vessel through the device; in operation, the inner lumen may be continuous with the body lumen, but can be regulated by attachment of saline, plasma, or other material to the proximal end of the device, to help regulate the pressure differential between the lumen and the environment outside of the patient. Multiple seals may be used between the inner and outer catheters, including redundant seals.

In addition to the seals, a locking member 57 configured as a screw-lock, may be included on at least the slider portion of the device. This lock may be used (e.g., locking by screwing distally/unscrewing proximally to unlock) to secure the slider in a desired position. Thus, the position of the wedges (extended/retracted position) and/or the deflection of the distal end may be locked in a desired position. Other locks (e.g., preventing or allowing rotation) may also be included.

Figure 8:
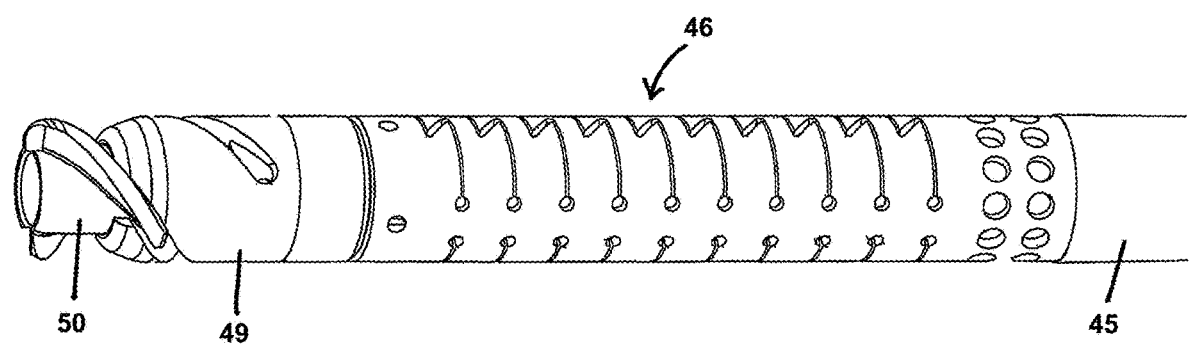
FIG. 8 is a side perspective view of the distal end region of one variation of a guidewire positioning and support catheter device.

FIG. 8 is an enlarged view of the distal end of the device shown in FIG. 5. In this example, the distal end includes a rotatable tip region including a protective housing 49 and extendable/retractable wedge portion 50. A steering or steerable bending region 46 is also shown, as previously described. The flexible bending region 46 connects to the outer catheter 45.

Figure 9A:
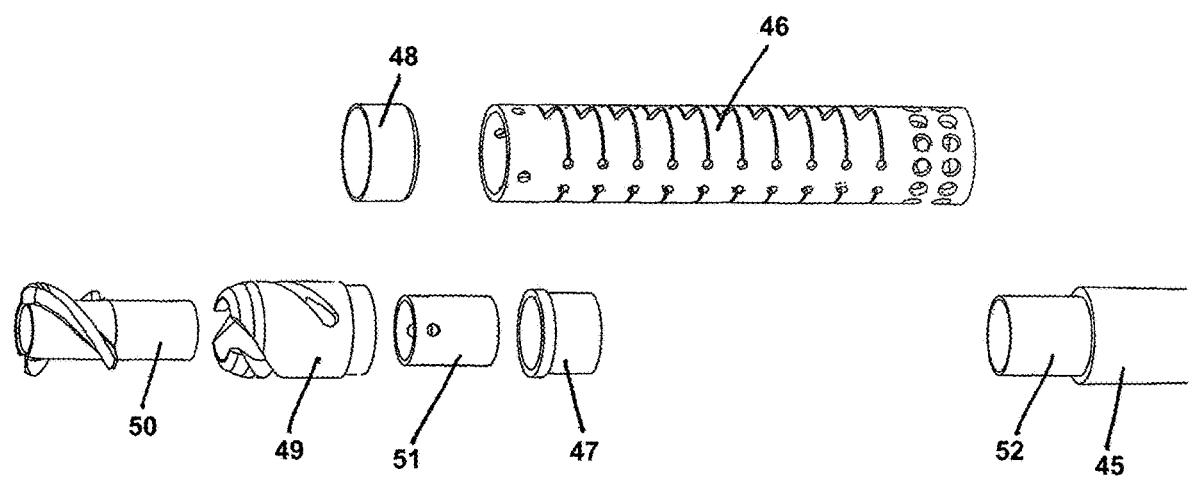
FIGS. 9A and 9B are exploded views of the distal end region shown in FIG. 8.
Figure 9B:
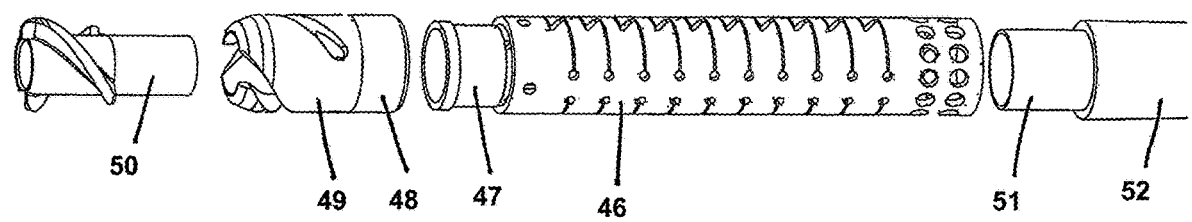
Figure 10D:
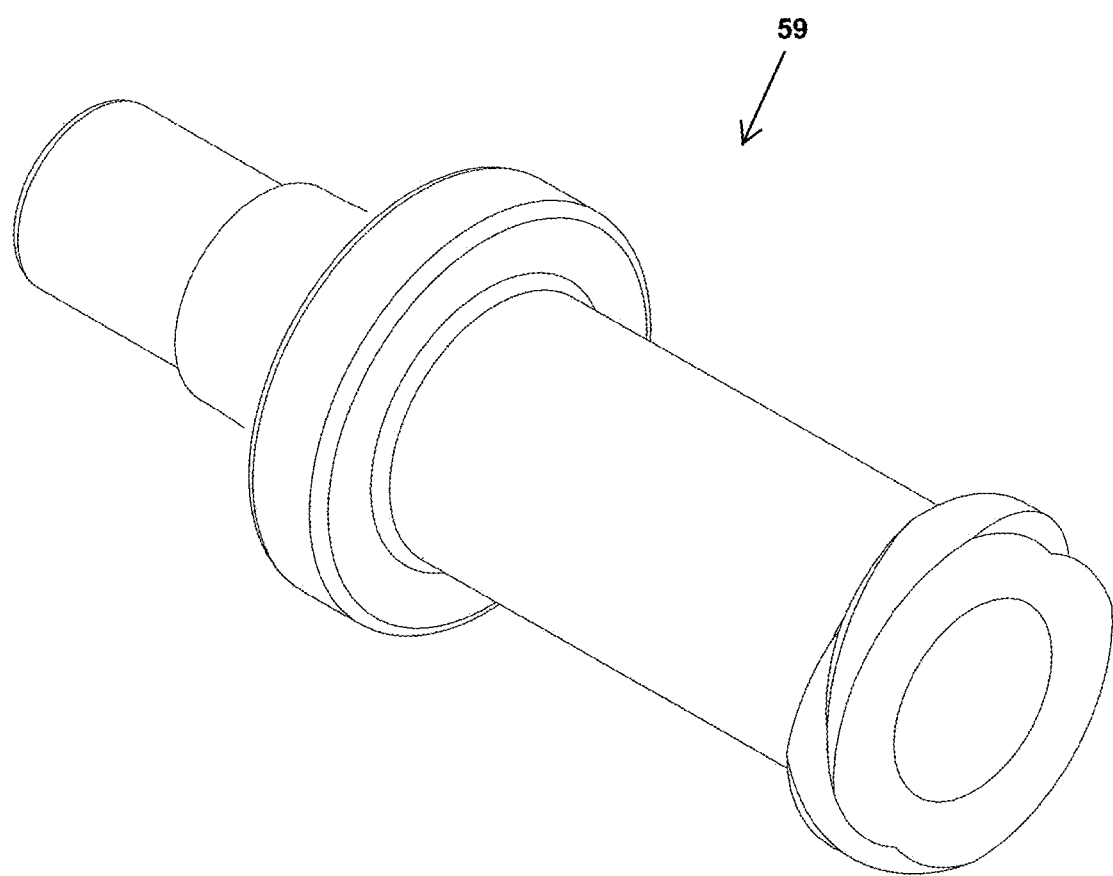
FIGS. 10D and 10E show alternative side perspective views of the luer fitting shown in FIG. 10A.
Figure 10E:
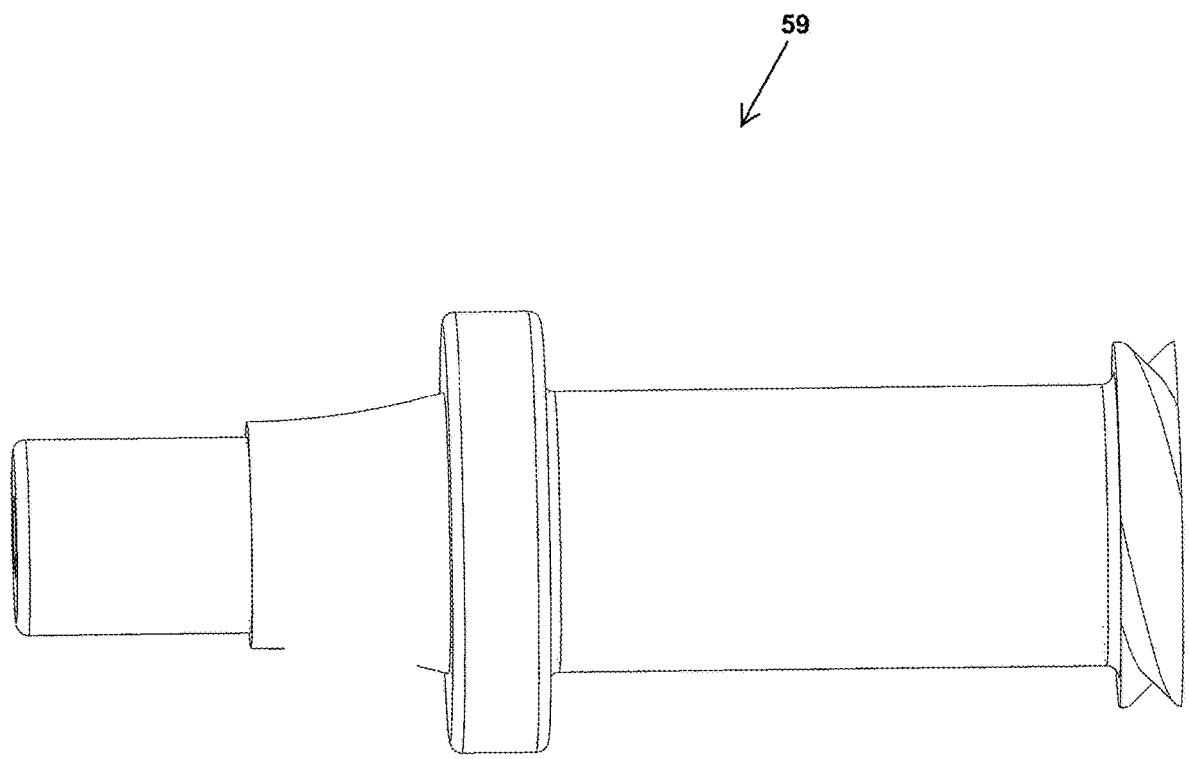
Figure 11A:
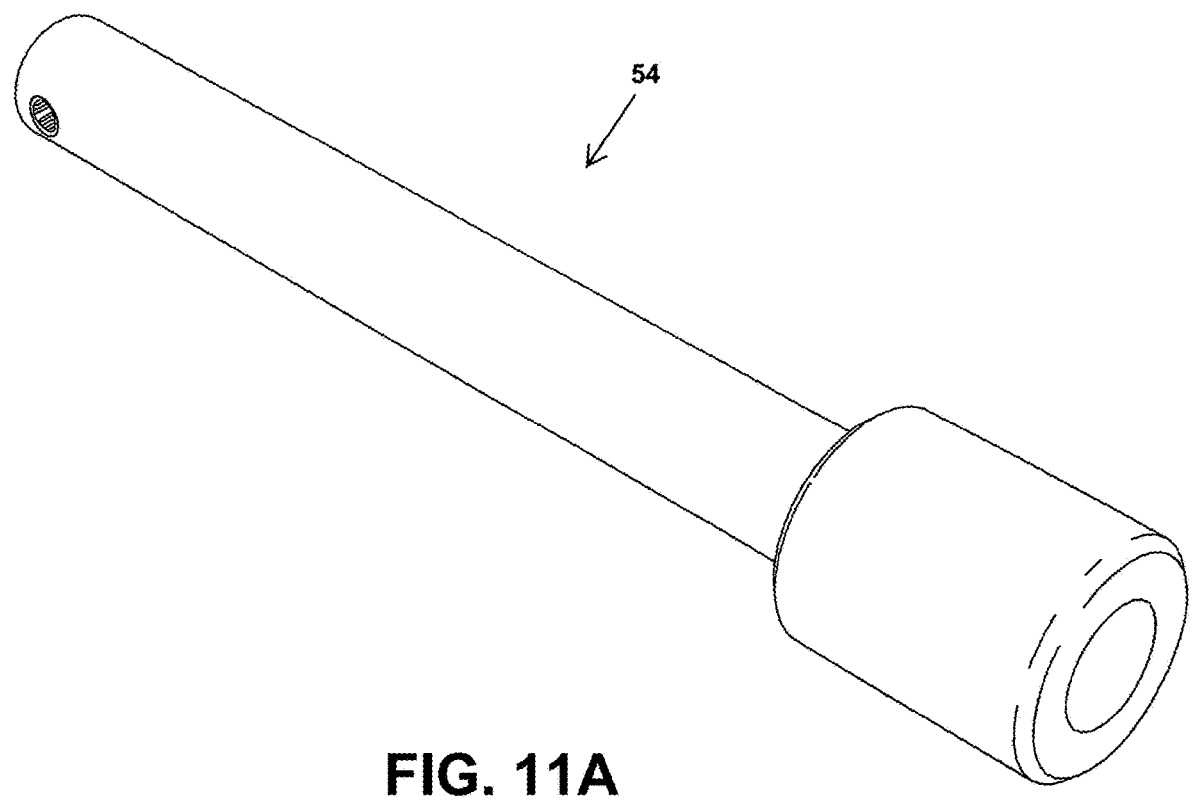
Figure 11E:
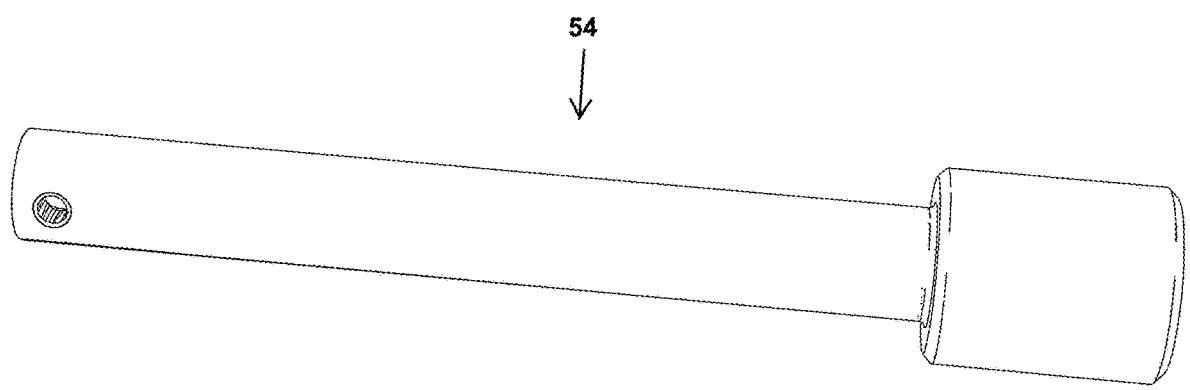
FIG. 11E shows another side perspective view.
Figure 12A:
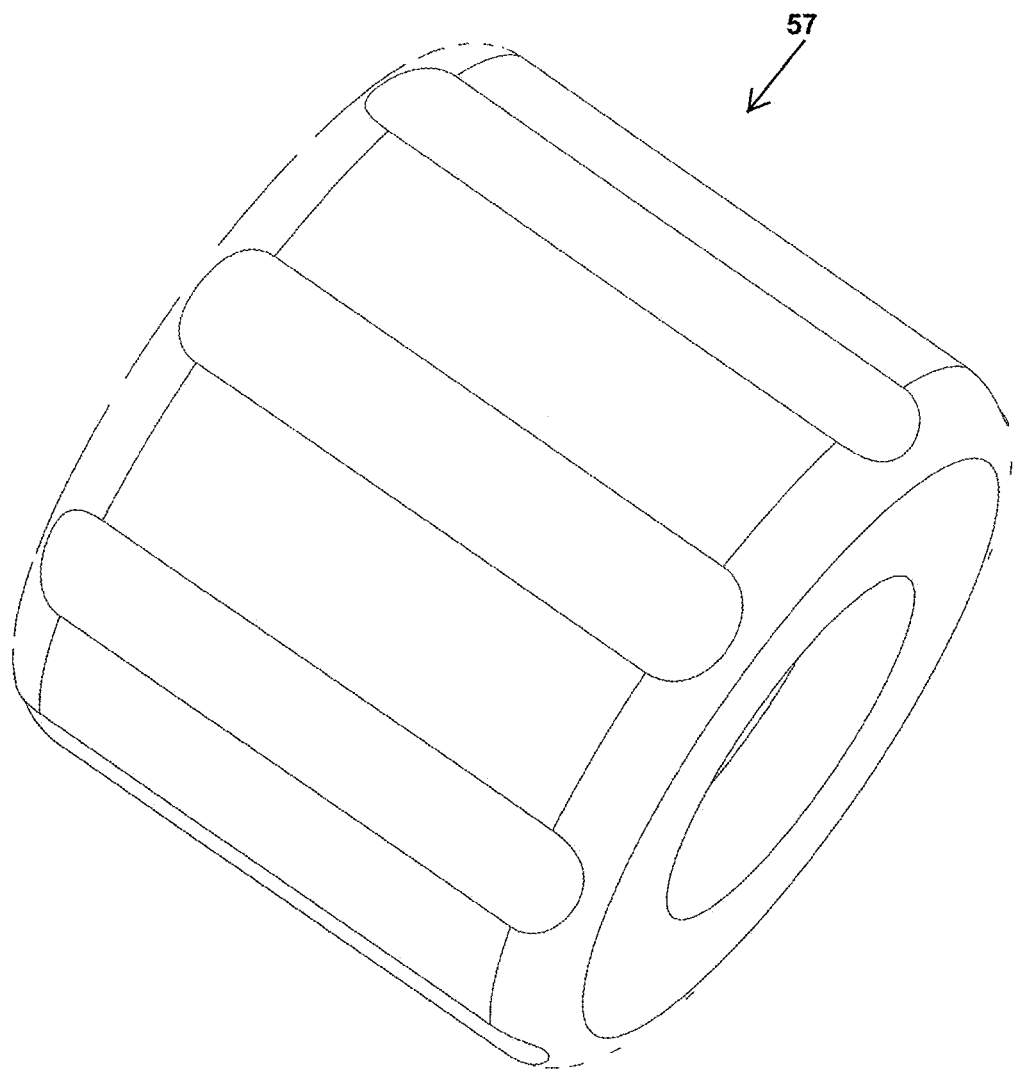
FIGS. 12A-12C show side perspective, end and side views, respectively, of a lock (shown as a rotator cap in this example) which may be used to lock the slider of FIG. 11A.
Figure 12C:
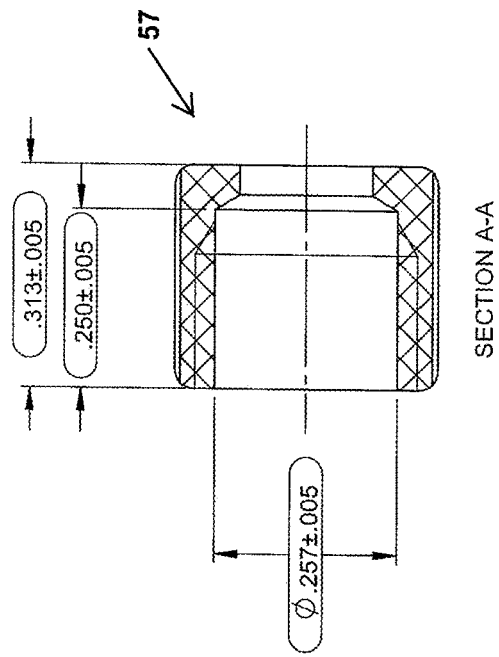
Figure 12B:
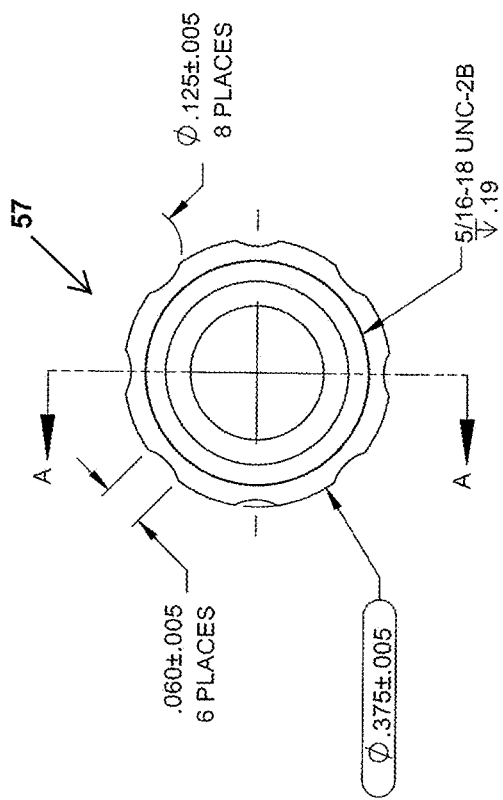
Figure 13A:
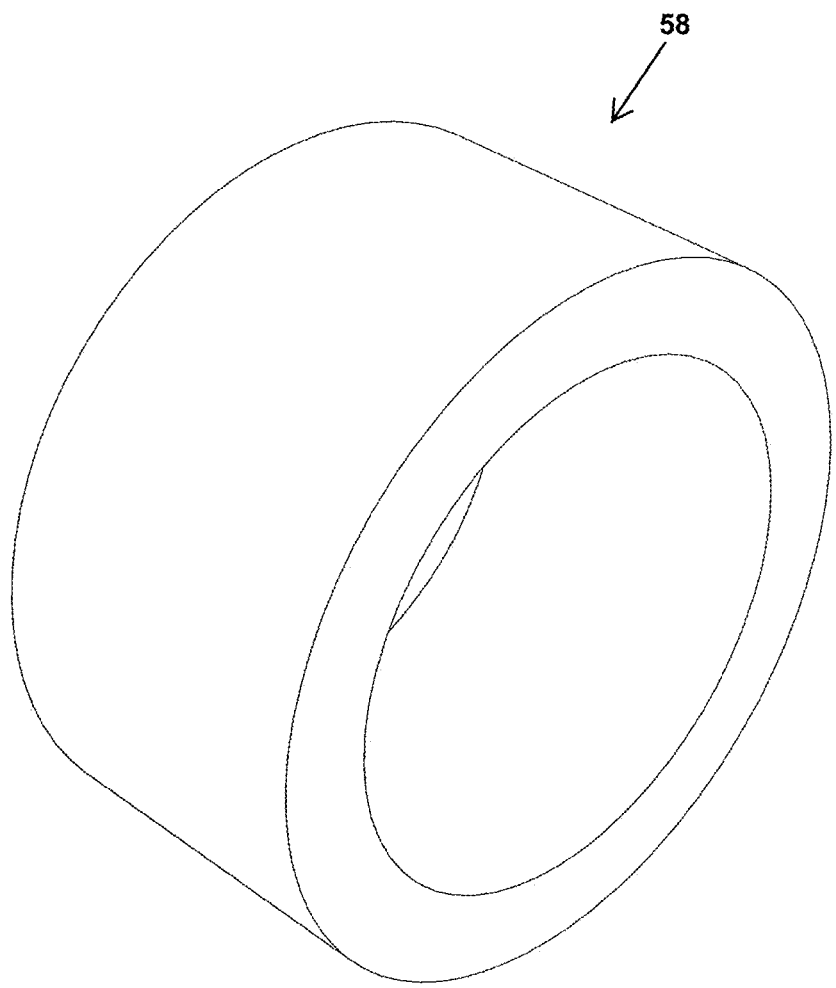
FIGS. 13A-13C show side perspective, end and side views, respectively, of a slider seal which may be used as part of a guidewire positioning and support catheter device.
Figure 13C:
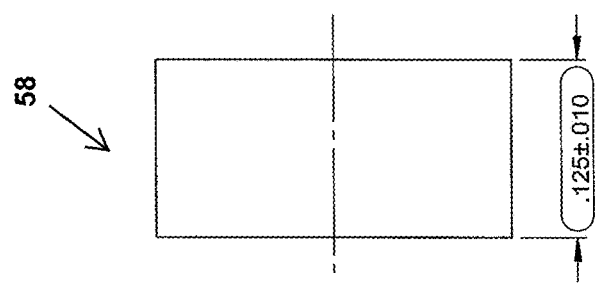
Figure 13B:
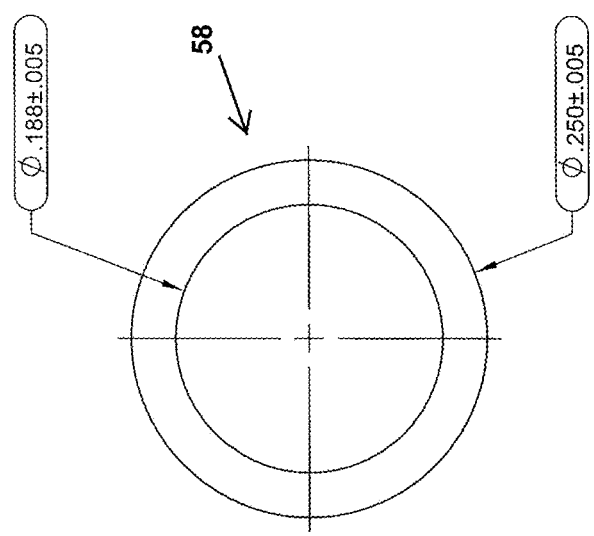
Figure 14A:
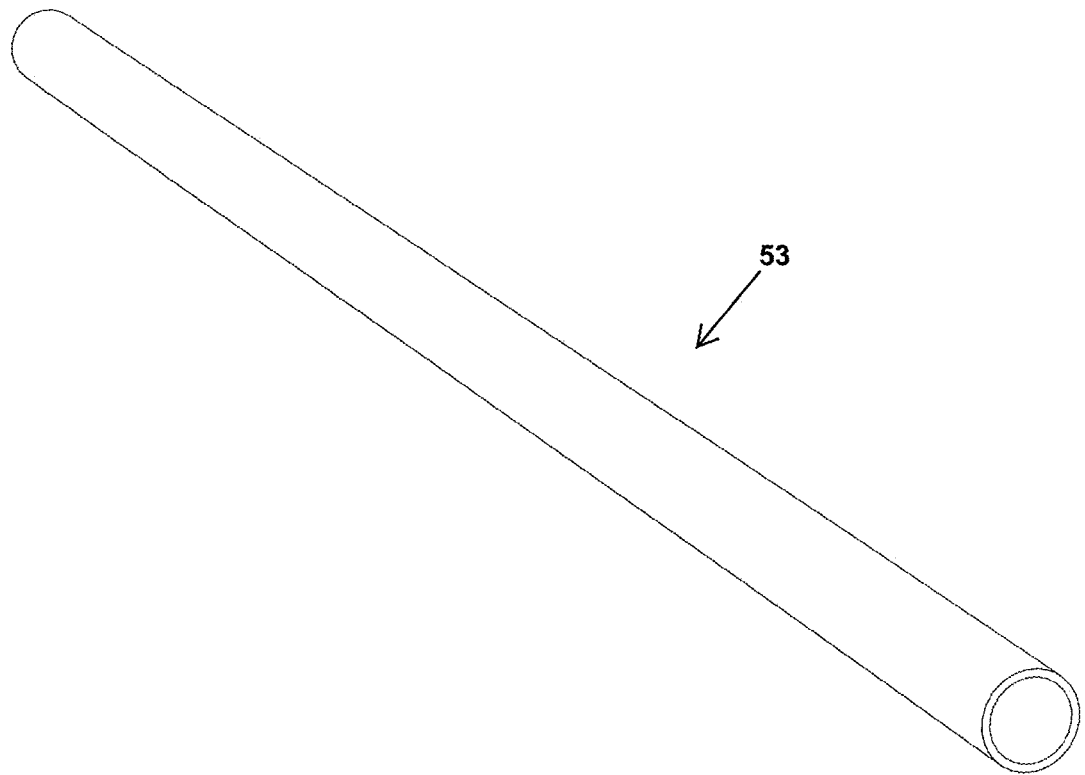
FIGS. 14A-14C show side perspective, end and side views, respectively, of a fluid sealing tube portion of a handle for a guidewire positioning and support catheter device.
Figures 14B, 14C:
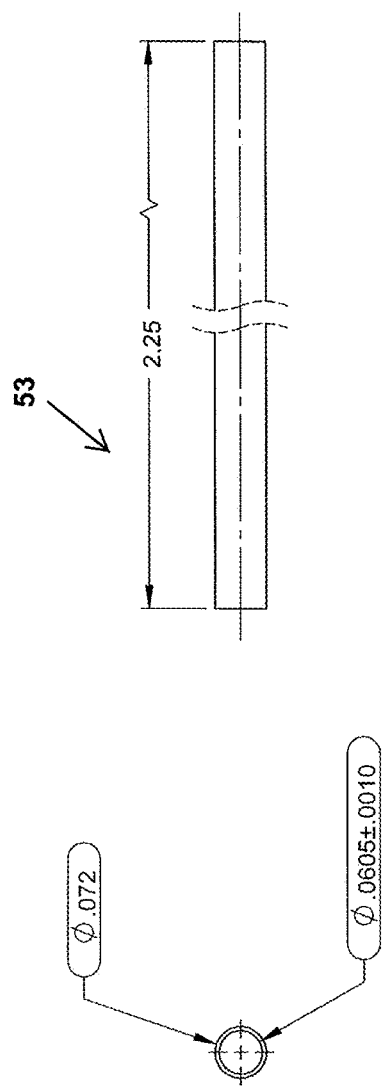
Figure 15B:
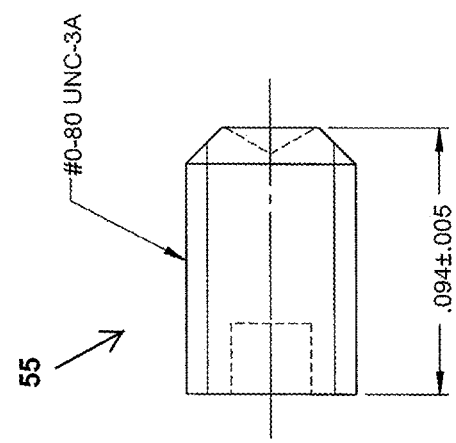
FIGS. 15A-15C show side perspective, side and end views, respectively, of a set screw portion of a handle for a guidewire positioning and support catheter device.
Figure 15A:
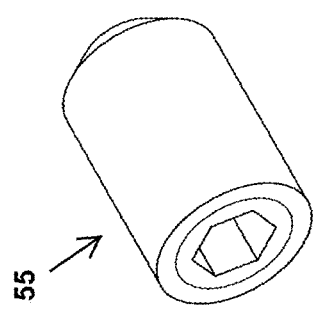
Figure 15C:
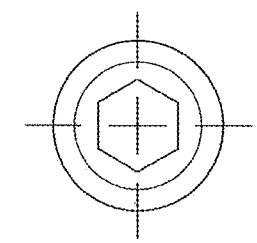
Figure 16A:
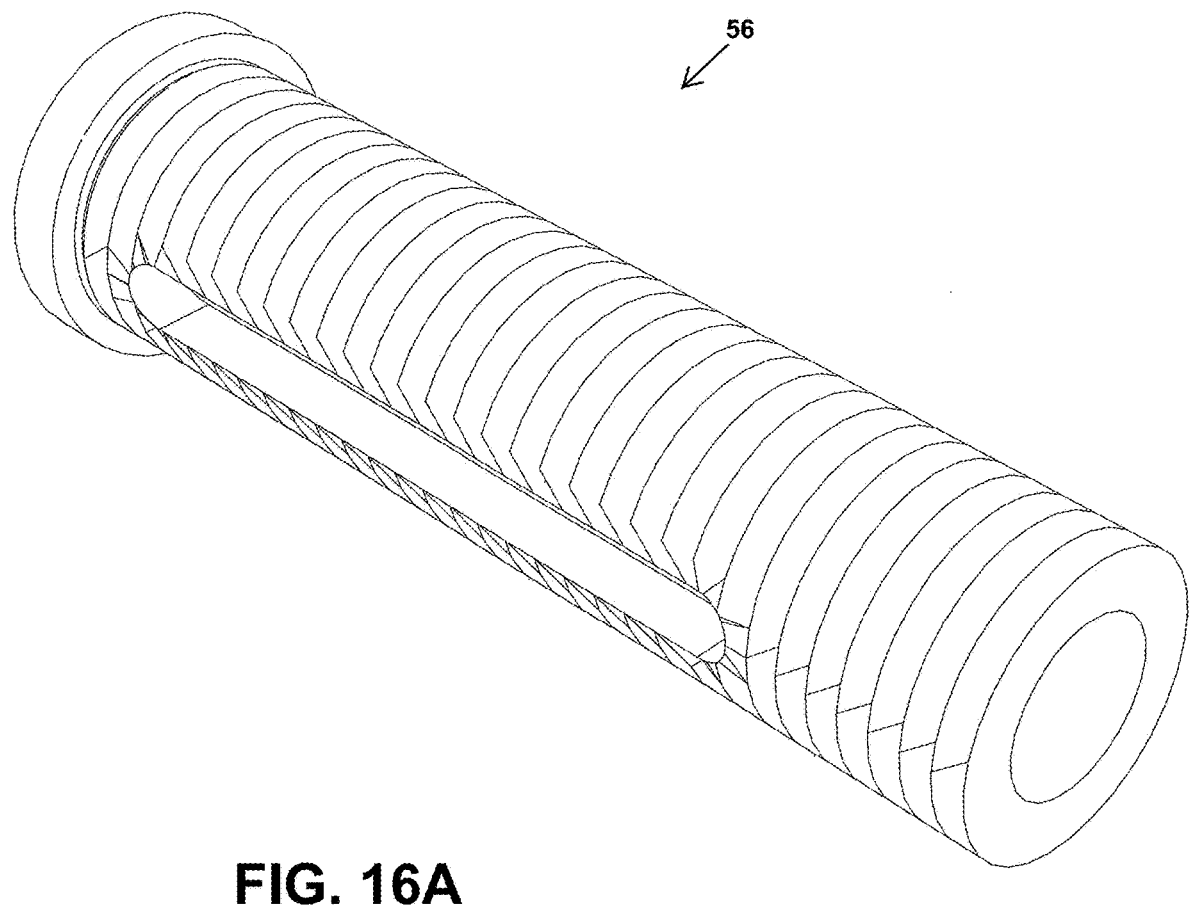
FIGS. 16A-16C show side perspective, side and end views, respectively, of a rotator portion of a handle for a guidewire positioning and support catheter device.
Figure 16B:
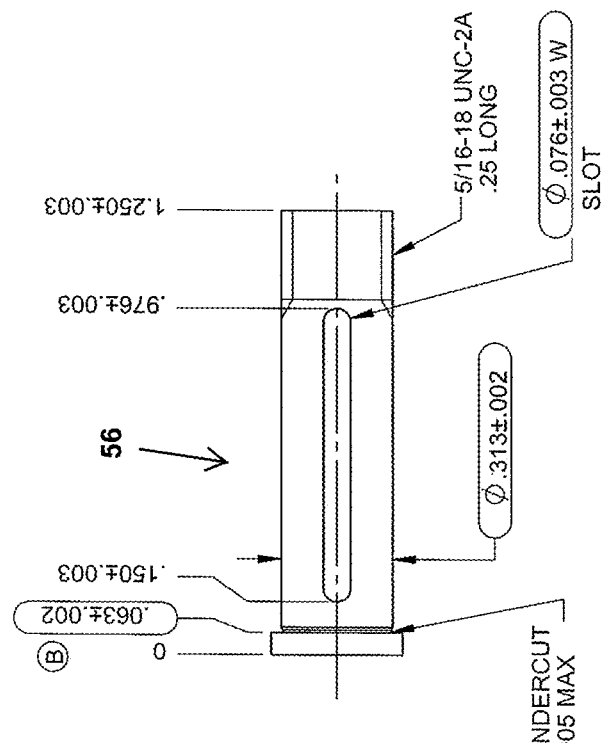
Figure 16C:
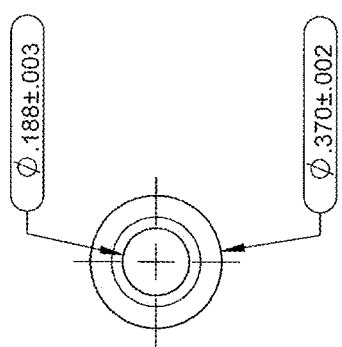
Figure 16D:
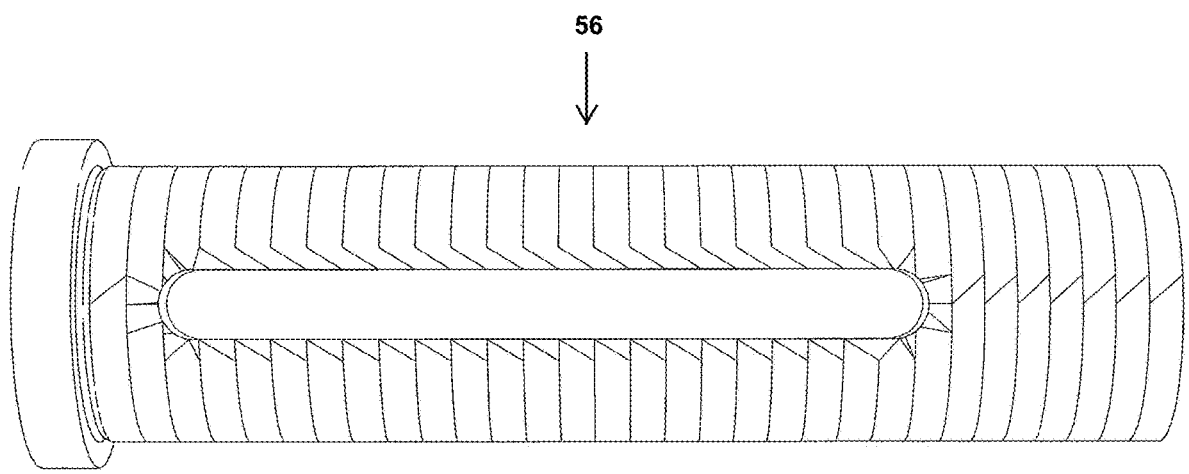
FIG. 16D is another side perspective view of the rotator portion shown in FIG. 16A.
Figure 17A:
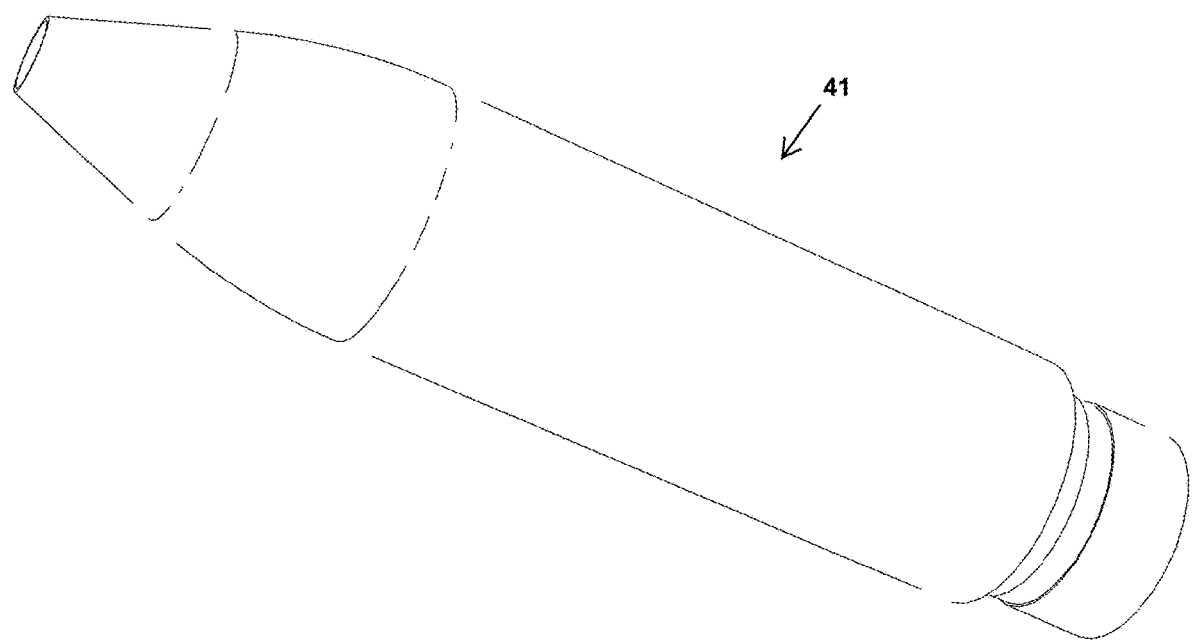
Figure 18A:
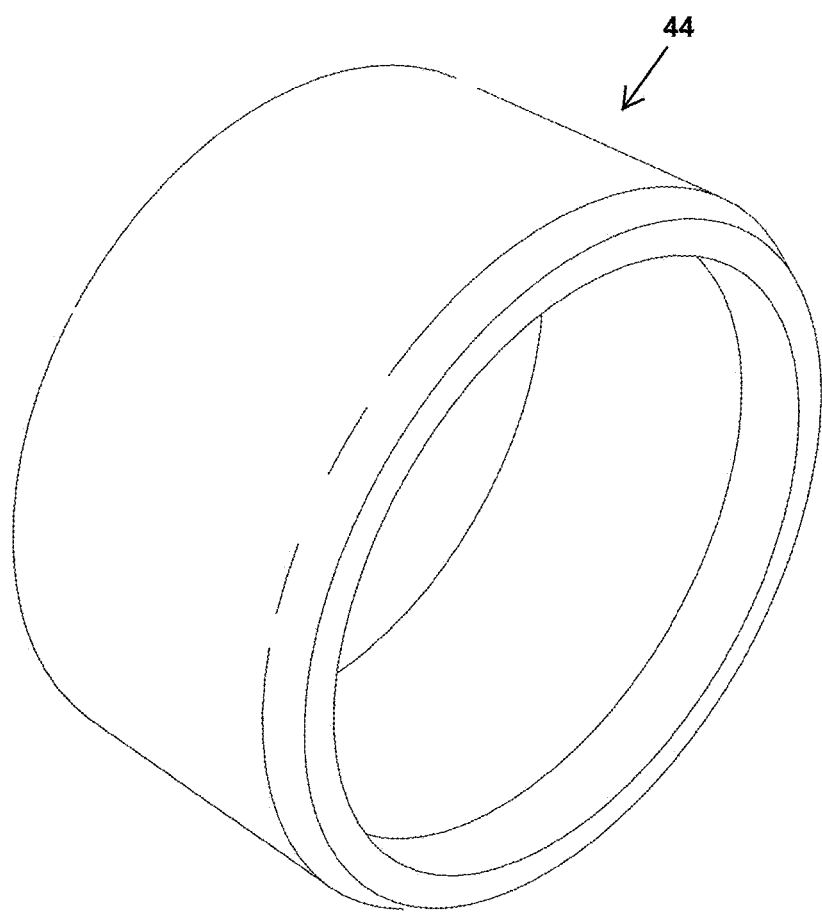
FIGS. 18A-18C show side perspective, side and end views, respectively, of a cap portion of a handle body for a handle of a guidewire positioning and support catheter device.
Figures 18B, 18C:
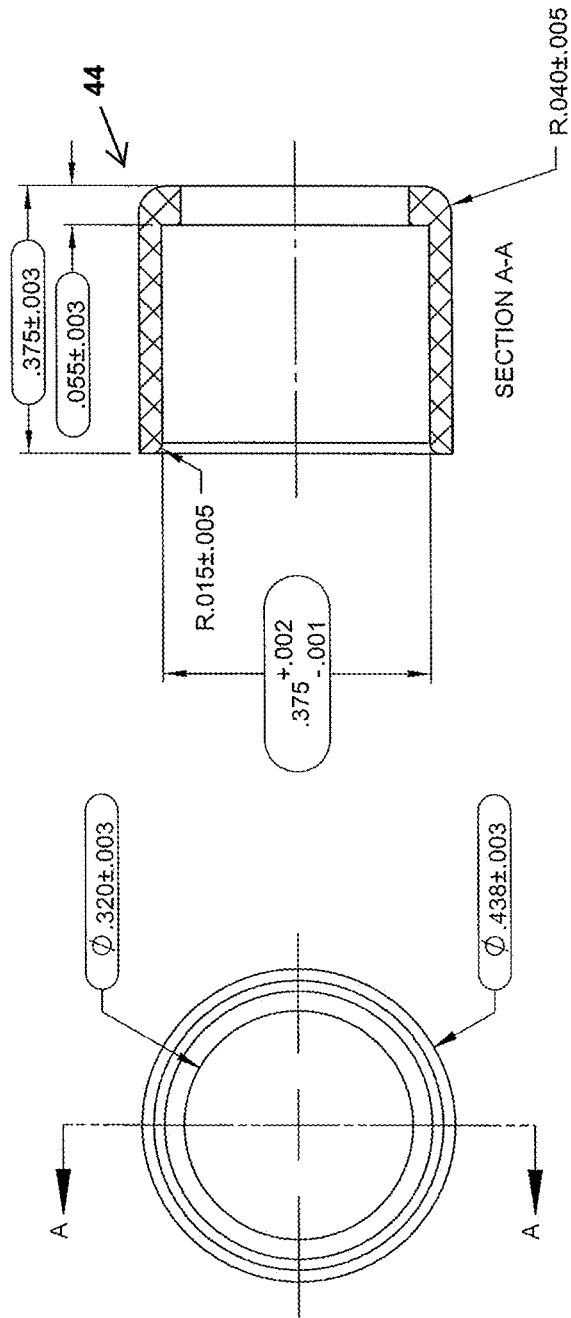
Figure 19A:
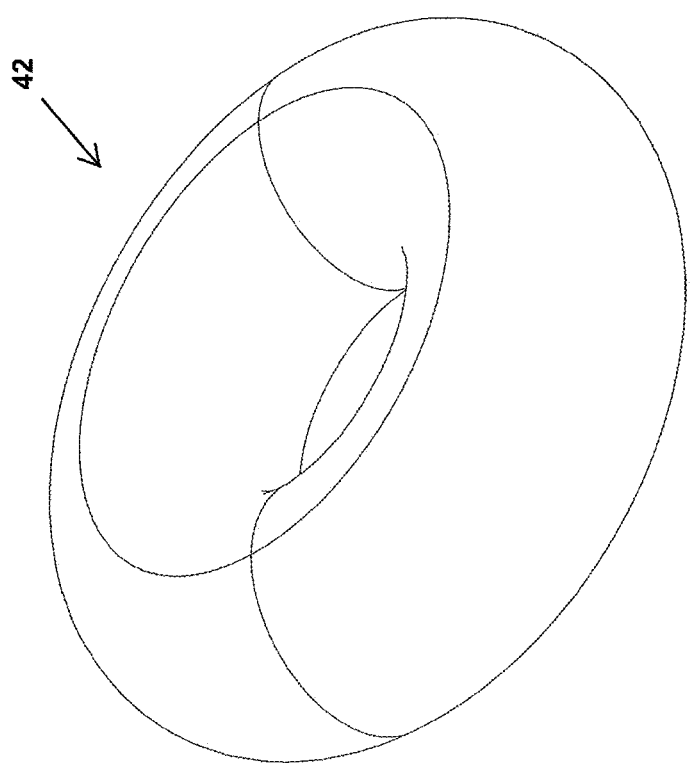
FIGS. 19A-19C show side perspective, front and side views, respectively, of a sealing O-ring portion of one variations of a handle for a guidewire positioning and support catheter device.
Figures 19B, 19C:
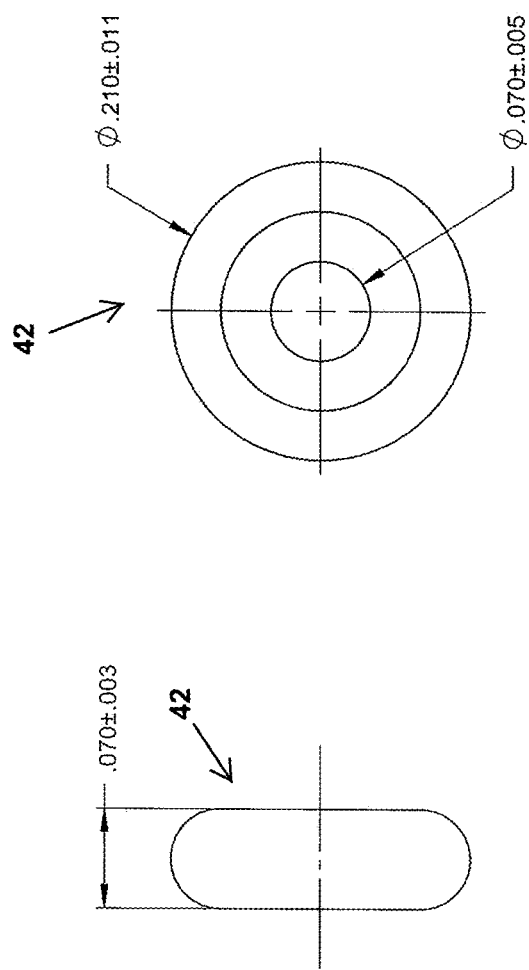
Figure 20D:
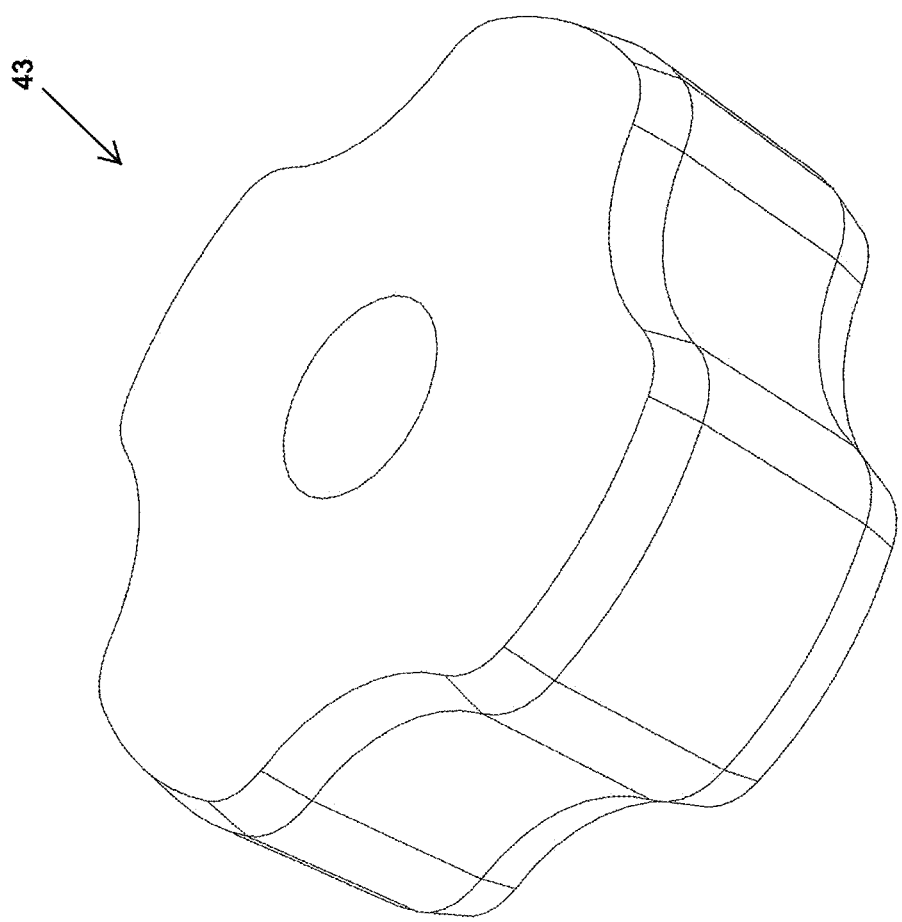
Figure 21:
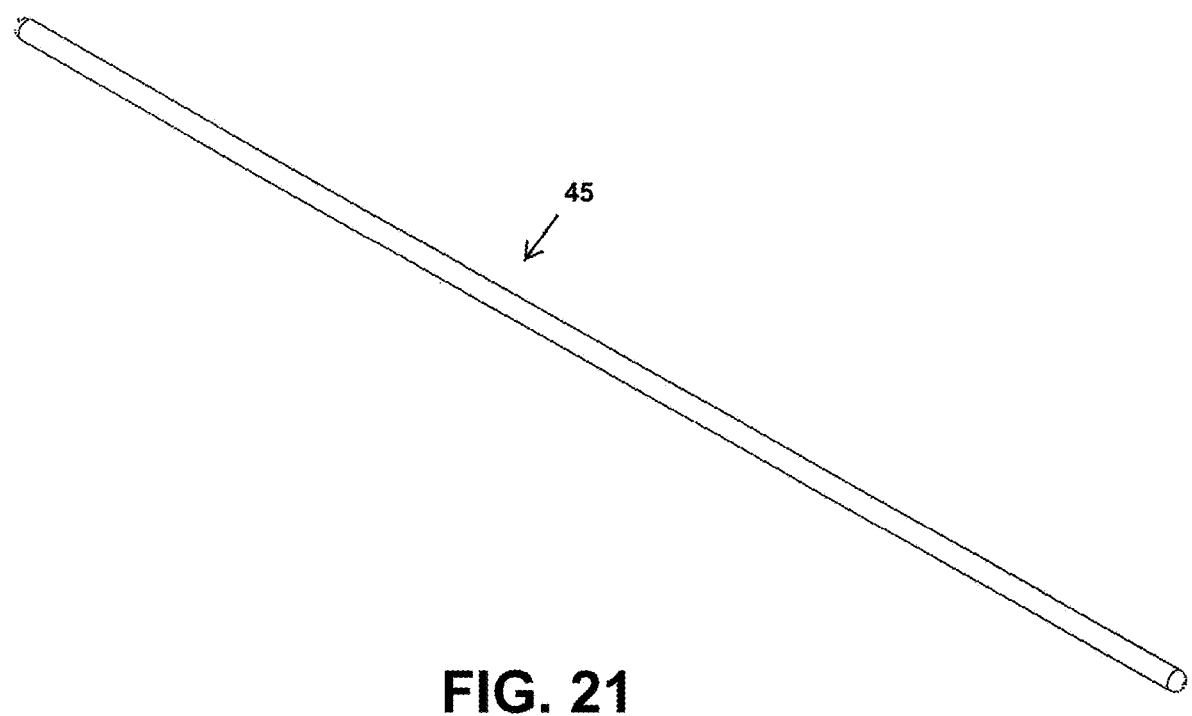
FIG. 21 is a side perspective view of an outer elongate shaft for a guidewire positioning and support catheter device.
Figure 22:
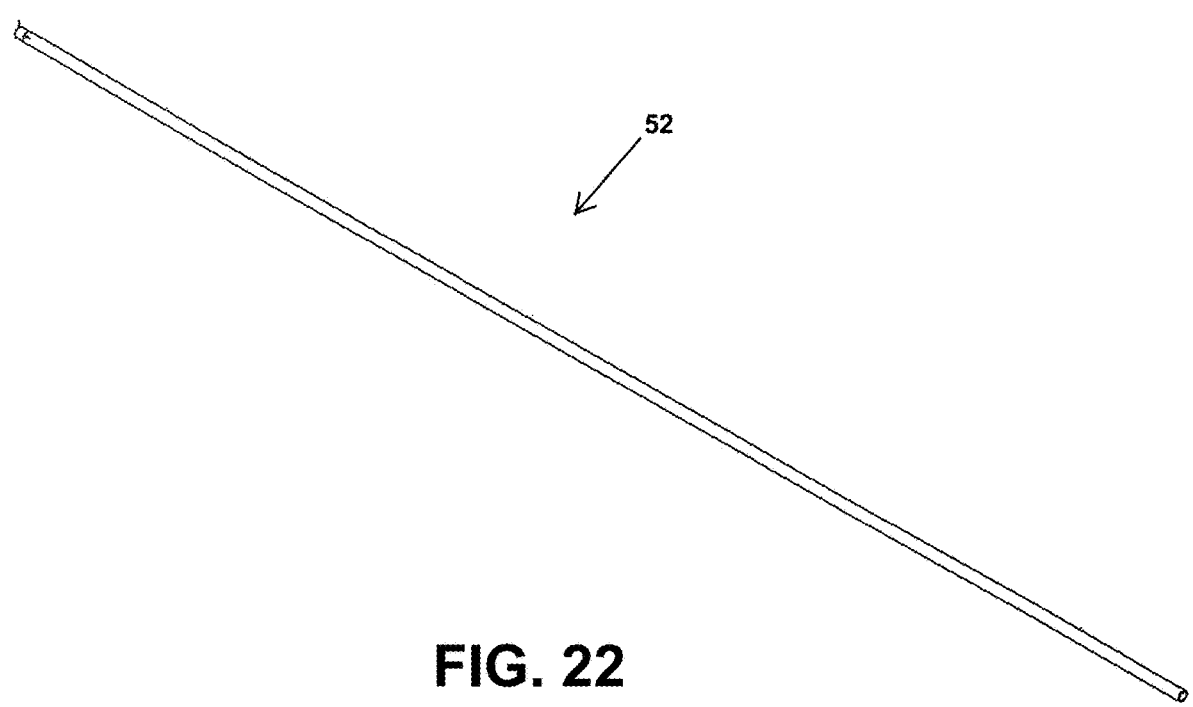
FIG. 22 is a side perspective view of a drive shaft (e.g., torque shaft) for a guidewire positioning and support catheter device.
Figure 24A:
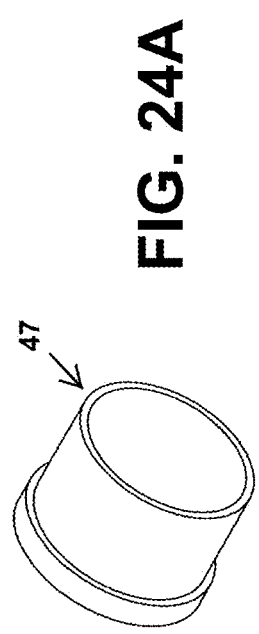
FIGS. 24A-24C show side perspective, side and end views, respectively, of an attachment ring for a steerable distal end portion of a guidewire positioning and support catheter device as described in one variation herein.
Figure 24C:
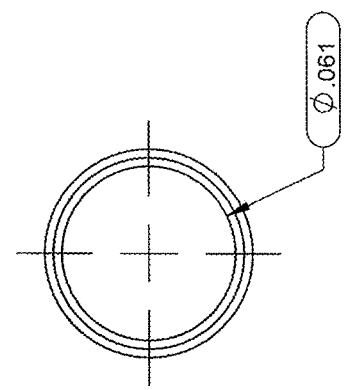
Figure 24B:
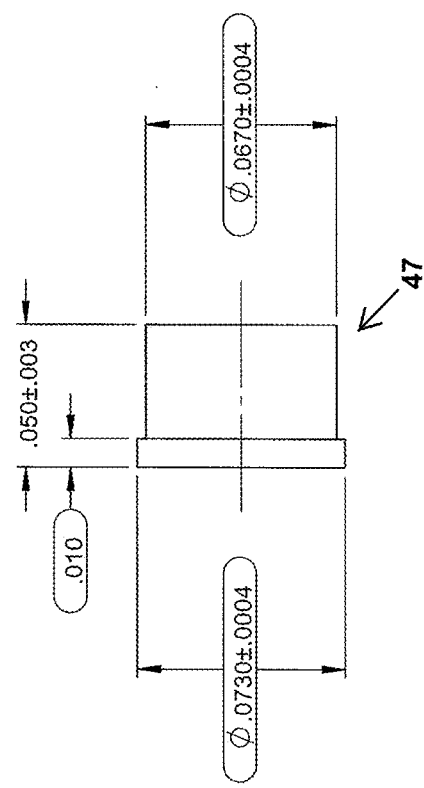
Figure 25A:
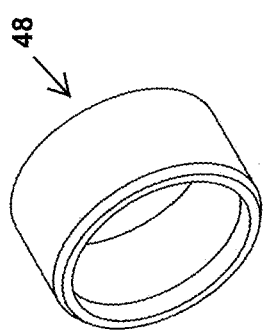
FIGS. 25A-25C show side perspective, side and end views, respectively, of a slip collar for a rotatable distal tip portion of a guidewire positioning and support catheter device as described in one variation herein.
Figure 25B:
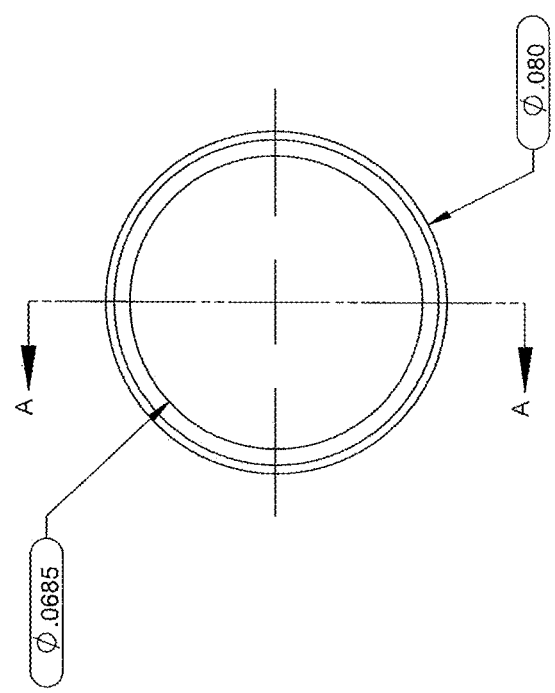
Figure 25C:
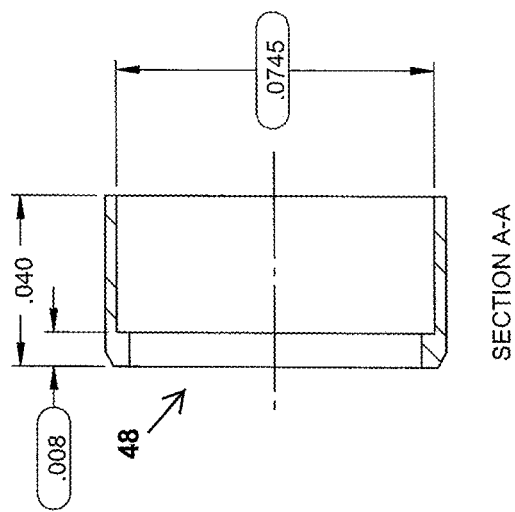
Figure 26A:
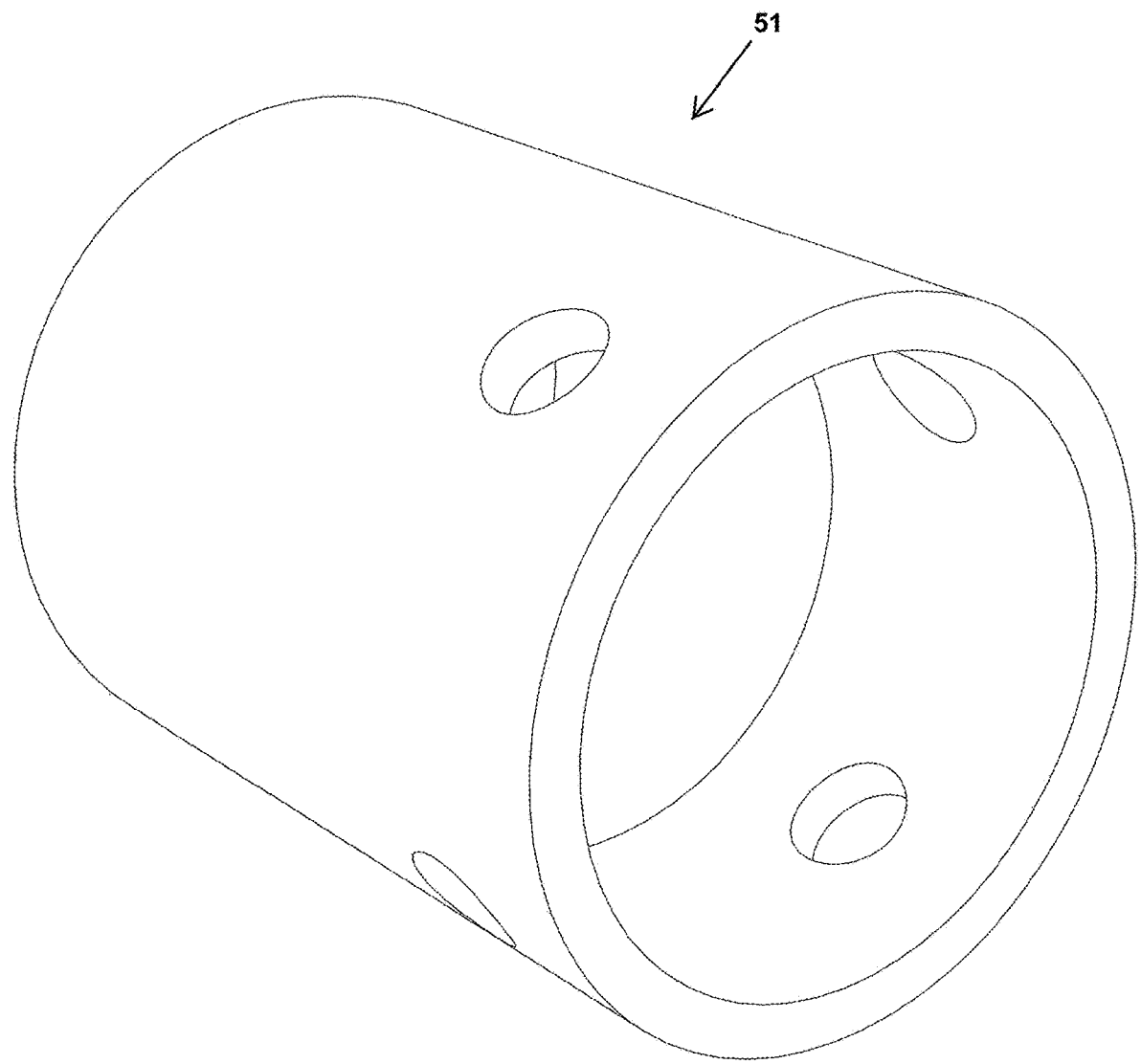
FIGS. 26A-26C show side perspective, side and end views, respectively, of a drive coupler element for a rotatable distal tip portion of a guidewire positioning and support catheter device as described in one variation herein.
Figure 26C:
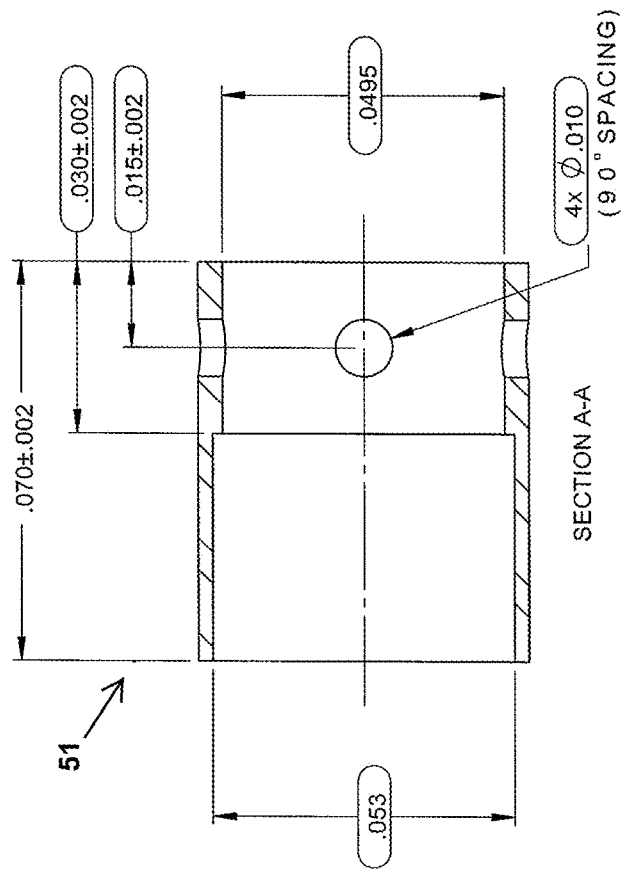
Figure 26B:
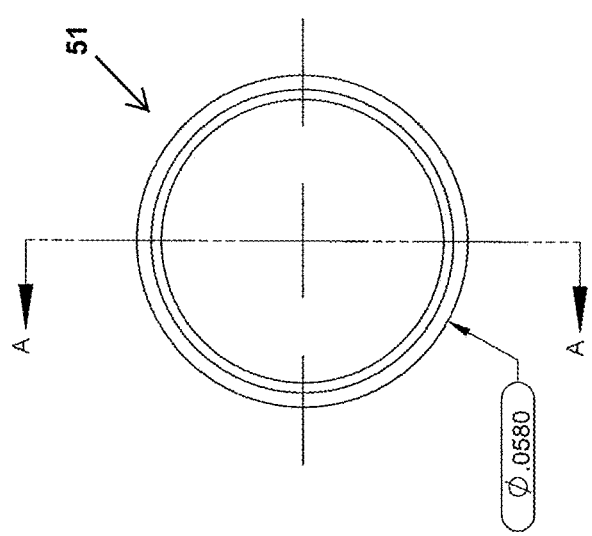
Figure 26D:
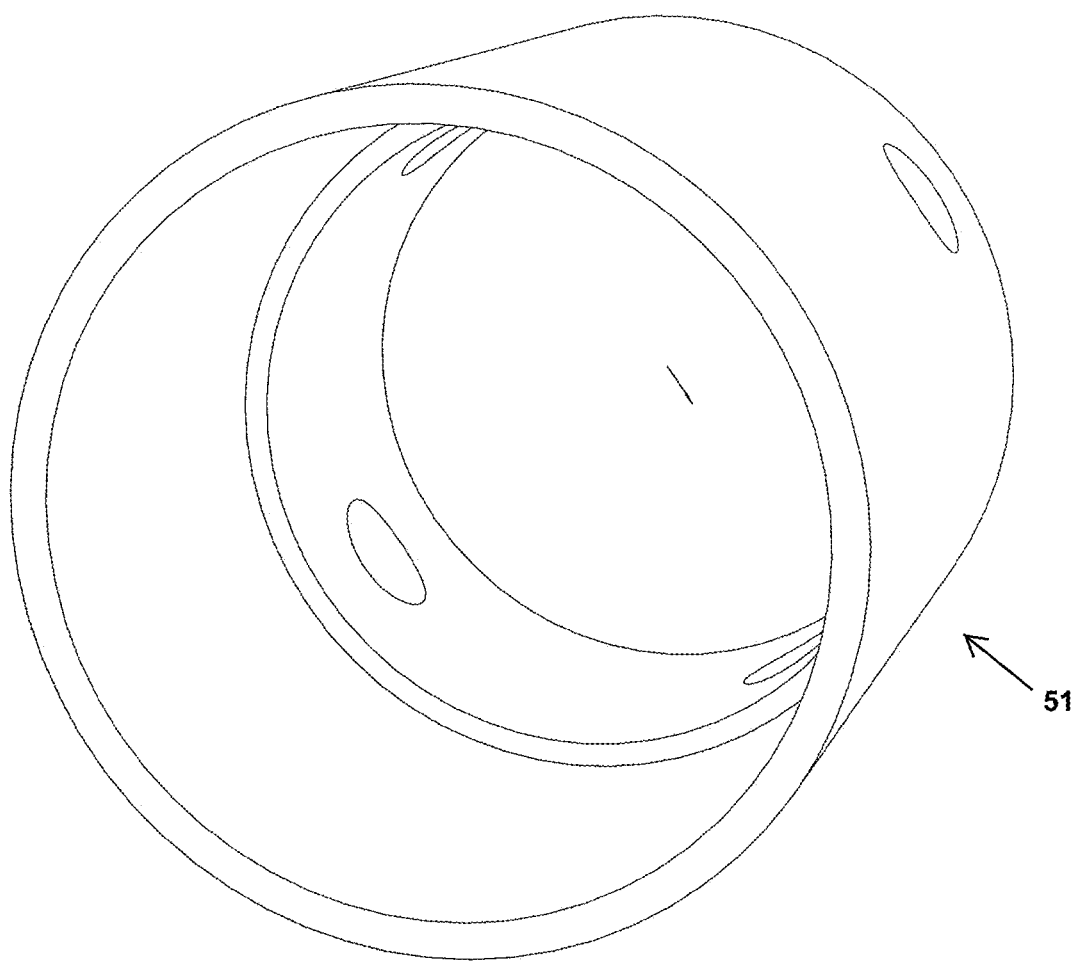
FIG. 26D shows an end perspective view of the drive coupler shown in FIGS. 26A-26C.
Figure 27D:
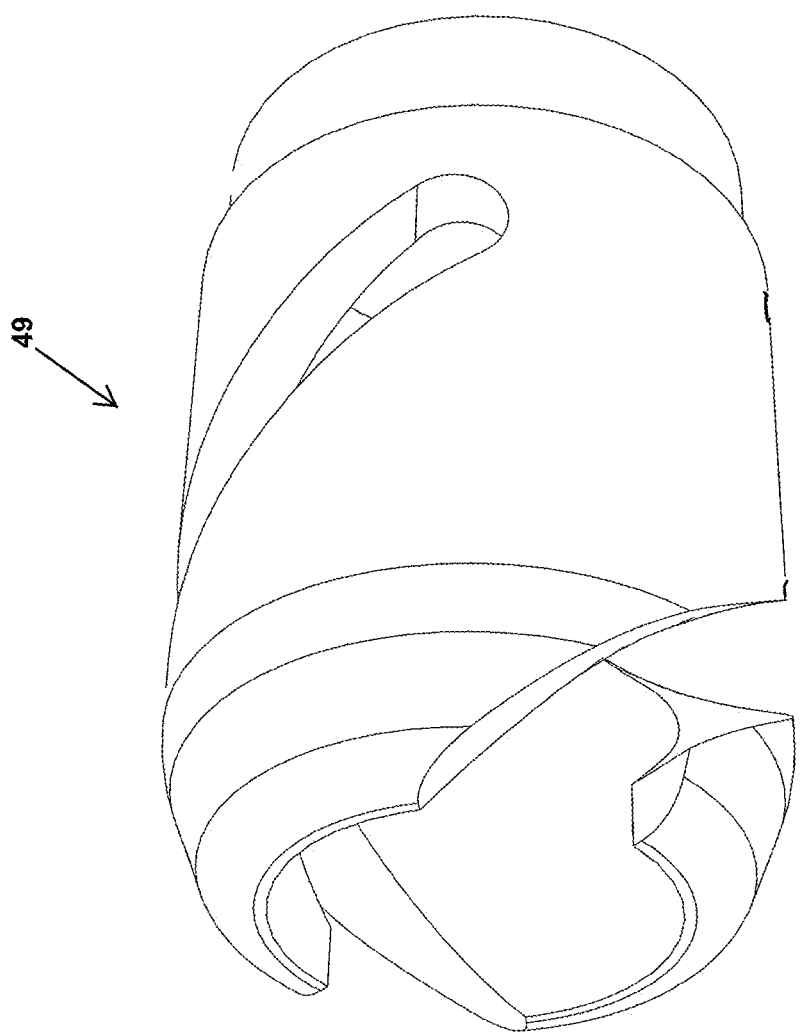
FIG. 27D is another side perspective view of the distal housing shown in FIG. 27A.
Figure 28A:
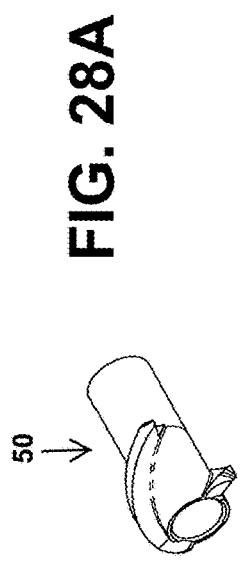
FIGS. 28A-28C show side perspective, side and end views, respectively, of a wedge (blade) element for a rotatable distal tip portion of a guidewire positioning and support catheter device as described in one variation herein.
Figure 28B:
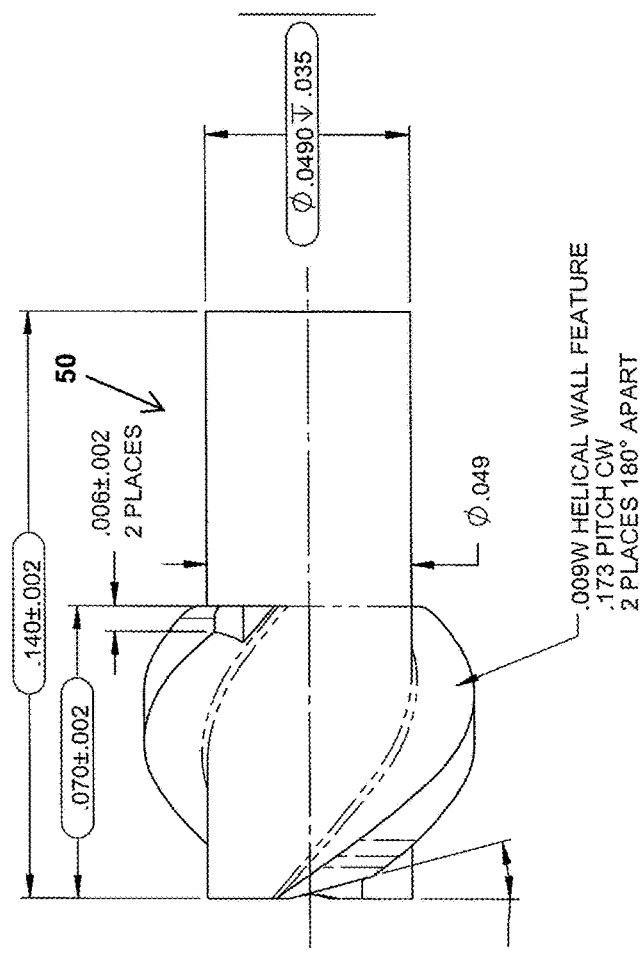
Figure 28C:
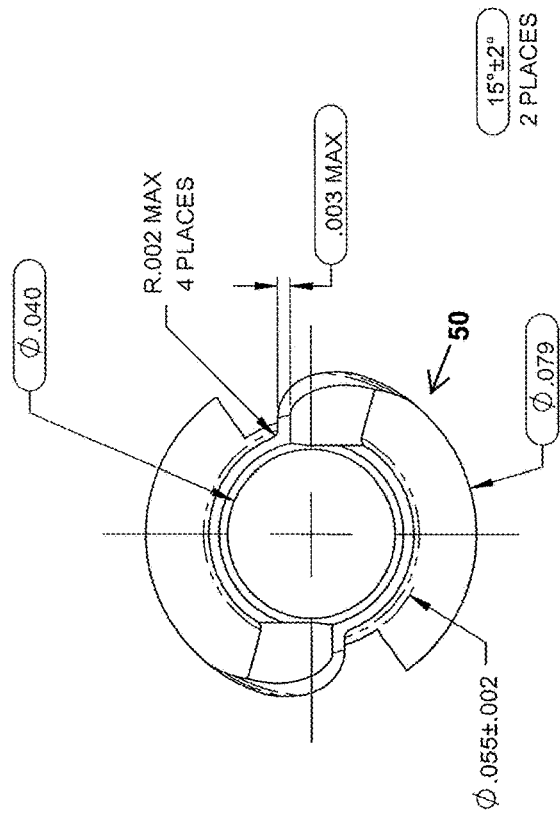
Figure 28D:
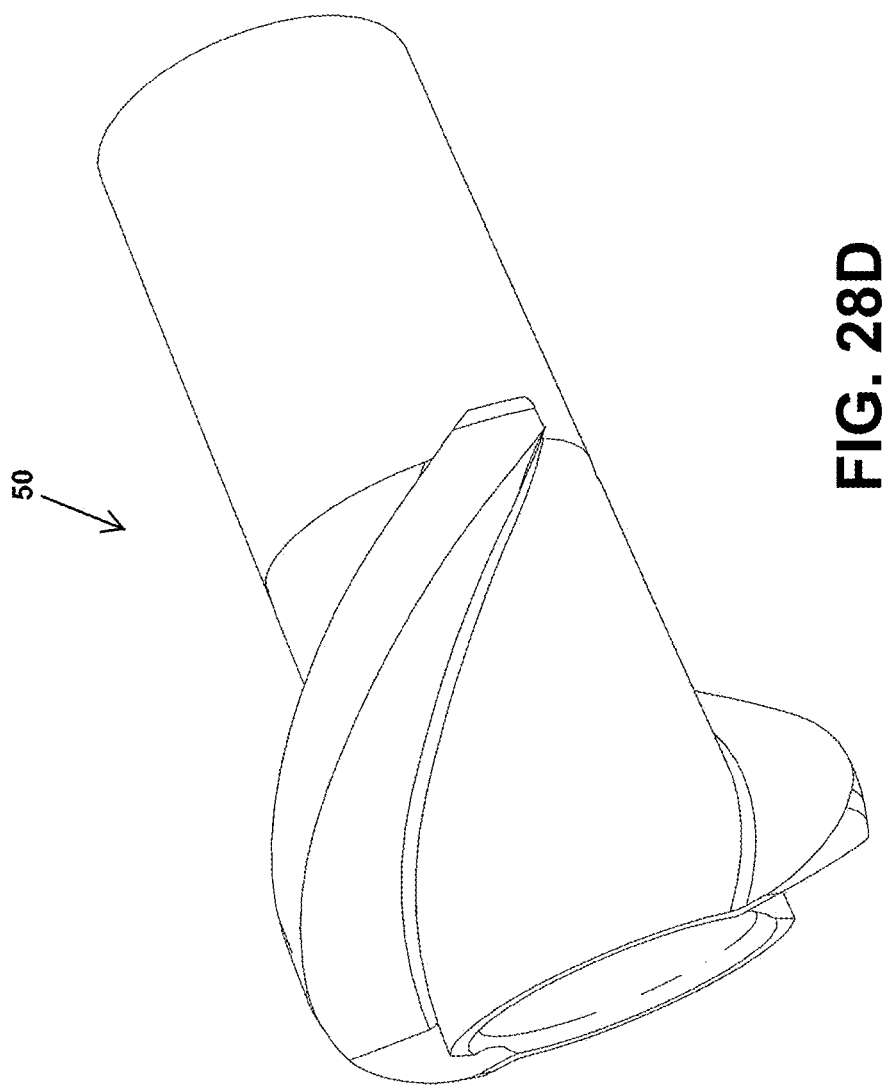
FIGS. 28D and 28E show alternative perspective views of the wedge element shown in FIG. 28A.
Figure 28E:
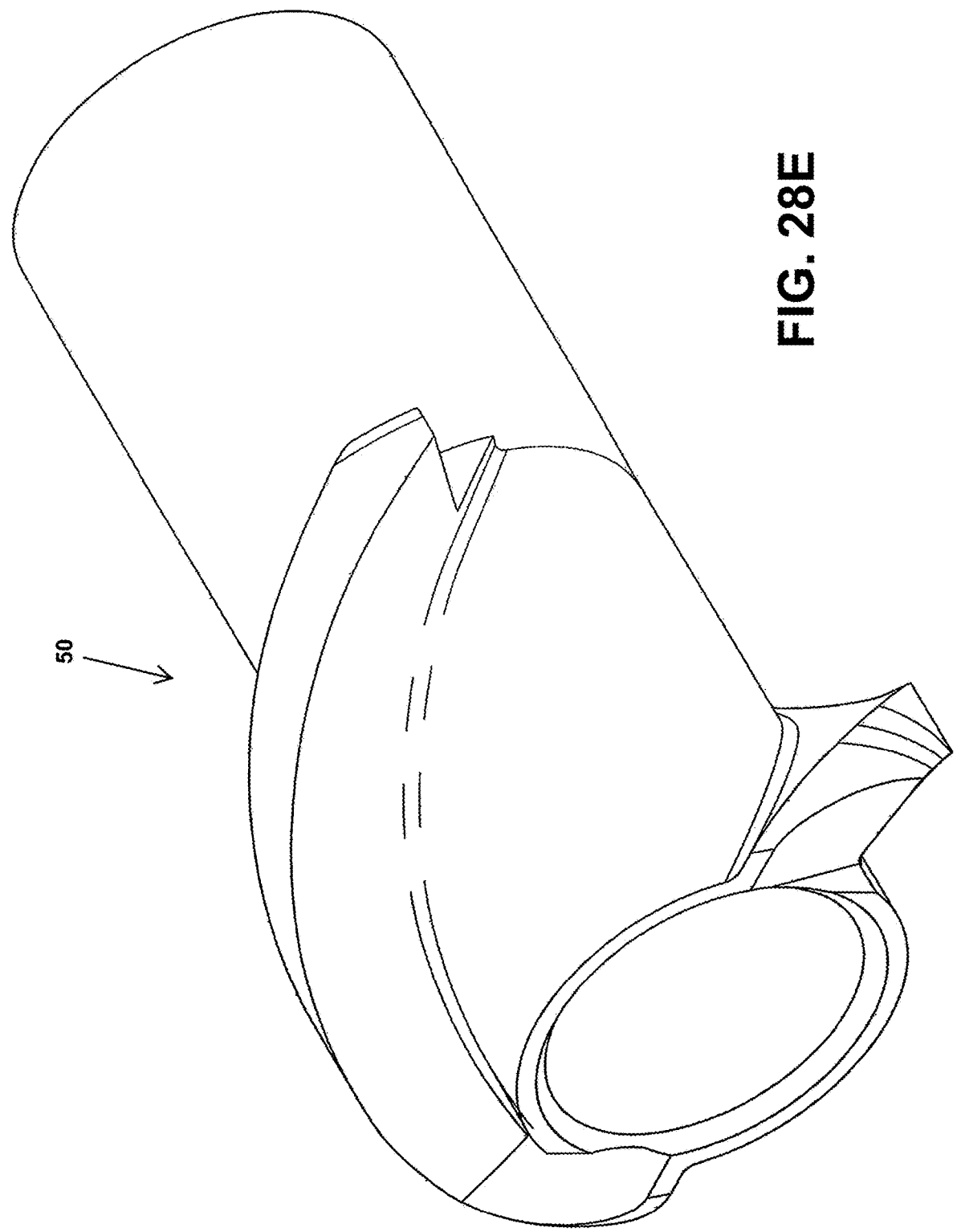

FIGS. 9A and 9B show exploded views of the distal end region of the catheter shown in FIGS. 5 and 8. In the exploded views shown, the inner drive shaft catheter 52 is shown within the outer catheter 45. Both the inner 52 and outer 45 catheters are flexible, so that the entire elongate length of the device is flexible. The inner drive (or torque) shaft catheter 52 connects to a rotatable mount, drive coupler 51, that connects to the wedge element 50. The rotatable mount is also engaged with the protective housing 49, and both of these elements are rotatably connected to the slip collar 48. Thus, rotation of the drive shaft catheter 52 rotates the wedge element and the protective housing at the distal tip, causing the entire distal tip region to rotate. In addition, the drive shaft 52 may be extended and/or retracted to extend or retract the wedge element, as previously described, and apply longitudinal force to bend the flexible region 46. The flexible region 46 is rigidly connected (e.g., welded) to an attachment ring 47 that connects to the slip ring 48 to allow a rotatable coupling between the distal tip region (e.g., protective housing 49) and the rest of the catheter. The proximal end of the flexible region 46 is connected (e.g., by welding) to the outer catheter 45.

Each of the various components shown in the exploded views of FIGS. 7 and 9A-9B are illustrated in greater detail in FIGS. 10A-28E in various views. Many of these figures include exemplary dimensions and tolerances. These dimensions are intended only as examples, and other dimensions may be used, or ranges of dimensions (e.g., +/−5% of the value shown, +/−10% of the value shown, etc.). For simplicity, the numbering of each component is maintained throughout the figures.

Methods of Use

In operation, any of the devices described herein may be used to treat an occlusion. In particular, these devices may be used to position a guidewire across an occlusion such as a chronic total occlusion of the peripheral vascular system. In general, treatment may include insertion of the catheter device into a vessel (e.g., blood vessel or artery) that is occluded. Fluoroscopy or other imaging technique may be used to visualize both the device and the vessel. Thus, appropriate contrast material may be used, and may be applied through the device or prior to insertion of the device. The device may be inserted using known minimally invasive (e.g., percutaneous) techniques. The device may be inserted with the wedge element retracted, so that the distal tip region is essentially atraumatic, to prevent damage to tissue or miss-guidance of the device.

The device may be positioned against the occlusion, and the distal tip region may be rotated with or without the wedge element deployed. The deploying the wedge element, in combination with the (manual) rotation may allow the device to penetrate the occlusion. The device may thus be advanced by rotation of the distal tip, either with or without the wedge element extended. The catheter may be gently driven (e.g., by the medical professional) distally to advance the device. The device may be used prior to insertion of a guidewire through the device, or it may be used in conjunction with a guidewire. For example, a guidewire may be extended from the distal end as it is advanced to also help penetrate the occlusion or steer the device.

The distal region of the device may also be steered by controlling the bending of the flexible distal region, as illustrated and described above. If the device should penetrate or exit the lumen of the vessel, it may be guided back into the vessel (re-entry) using the steerable distal end.

For example, in operation, a catheter may be removed from a sterile package and transfer to a sterile field where it can be first flushed with heparanized saline through the proximal port located on the handle assembly. The catheter may then be lightly wiped with heparanized saline in preparation for insertion. Before use, the catheter may be tested to confirm that the wedges extend and retract and the distal end region of the device bends for steering. In general, to control the device, the rotator may be turned clockwise and counterclockwise to rotate the distal tip region. The slider may be longitudinally slide distally to extend the wedges from the tip region (from out of the housing) and further distally to bend the steerable distal end region. The slider may then be slid proximally to 'unbend' (restore to straight) the distal end, and to retract the wedge region. The slider lock may be rotated clockwise to engage (lock) the slider in position (and therefore the extension of the wedge(s) and the bend of the distal end region, and the slider lock may be rotated counterclockwise to disengage and allow longitudinal slider movement.

The device may be inserted into the vessel by first retracting the wedges into the housing at the distal tip. Prior to inserting the catheters describe herein, a guidewire may be inserted up to (or adjacent to) the occlusion using standard techniques. The catheter may then be advanced over the guidewire under fluoroscopic guidance through a sheath to the target lesion (occlusion). In operation, the guidewire support catheter is used with a guidewire within the central lumen, which may provide additional stiffness and support to the catheter.

When the device is positioned, manually torque and advance the catheter through a region of the peripheral vasculature while maintaining catheter position at the lesion site. If additional support is necessary to advance beyond the region, deploy the wedges by pushing on the slider the slider lock may be engaged if desired. The rotator may be manipulated as needed to advance the catheter. To ensure the distal tip of the device remains in the vessel's true lumen, the Slider may be pushed until the tip is positioned properly and engage the slider lock.

After advancing beyond the lesion, the wedges may be fully retracted under fluoroscopic guidance, and the catheter may be retracted, leaving the guidewire in place.

Figure 29:
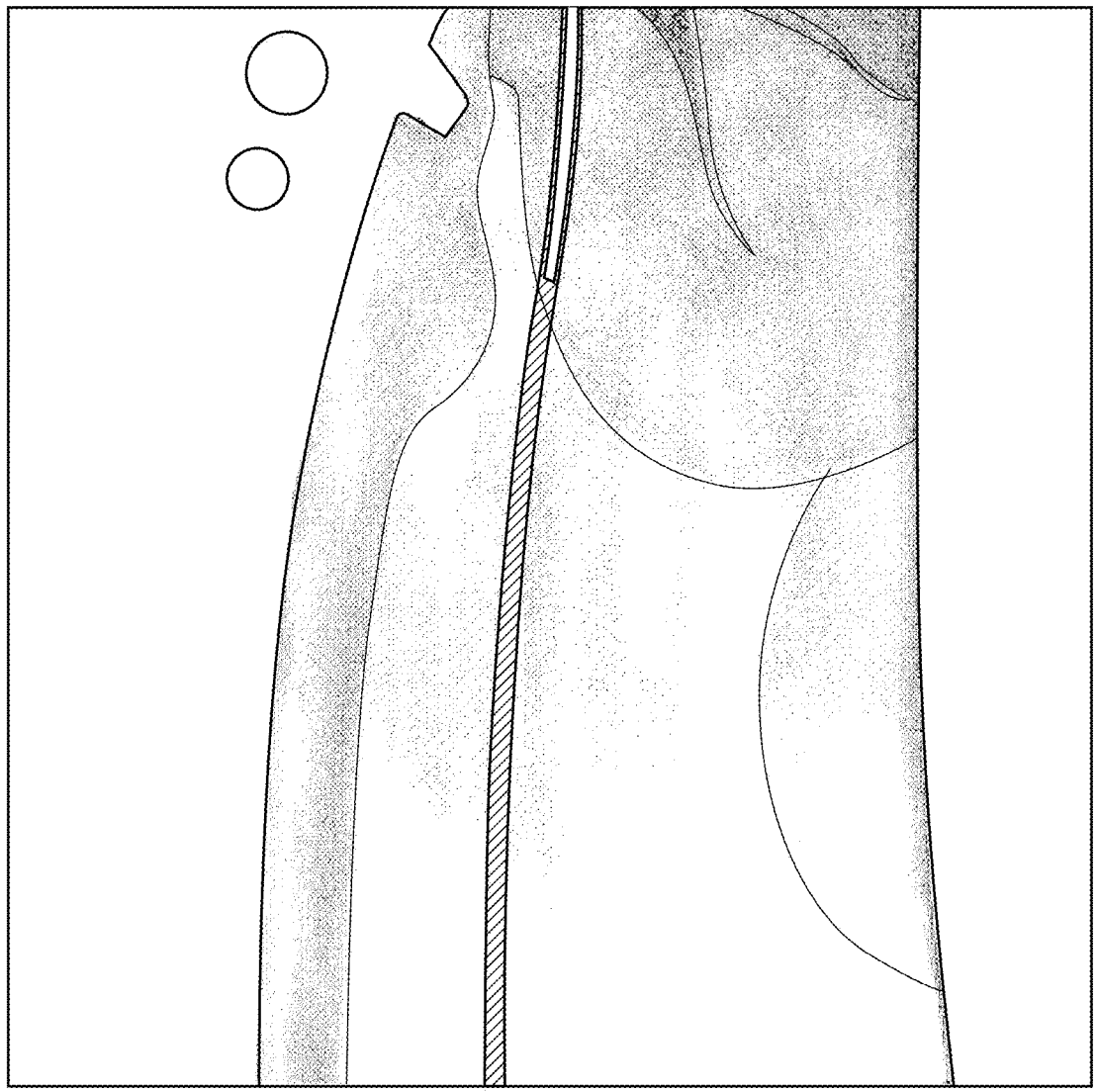
FIG. 29 is a fluoroscopic image thorough a region of a subject's body having an occluded vessel.
Figure 30A:
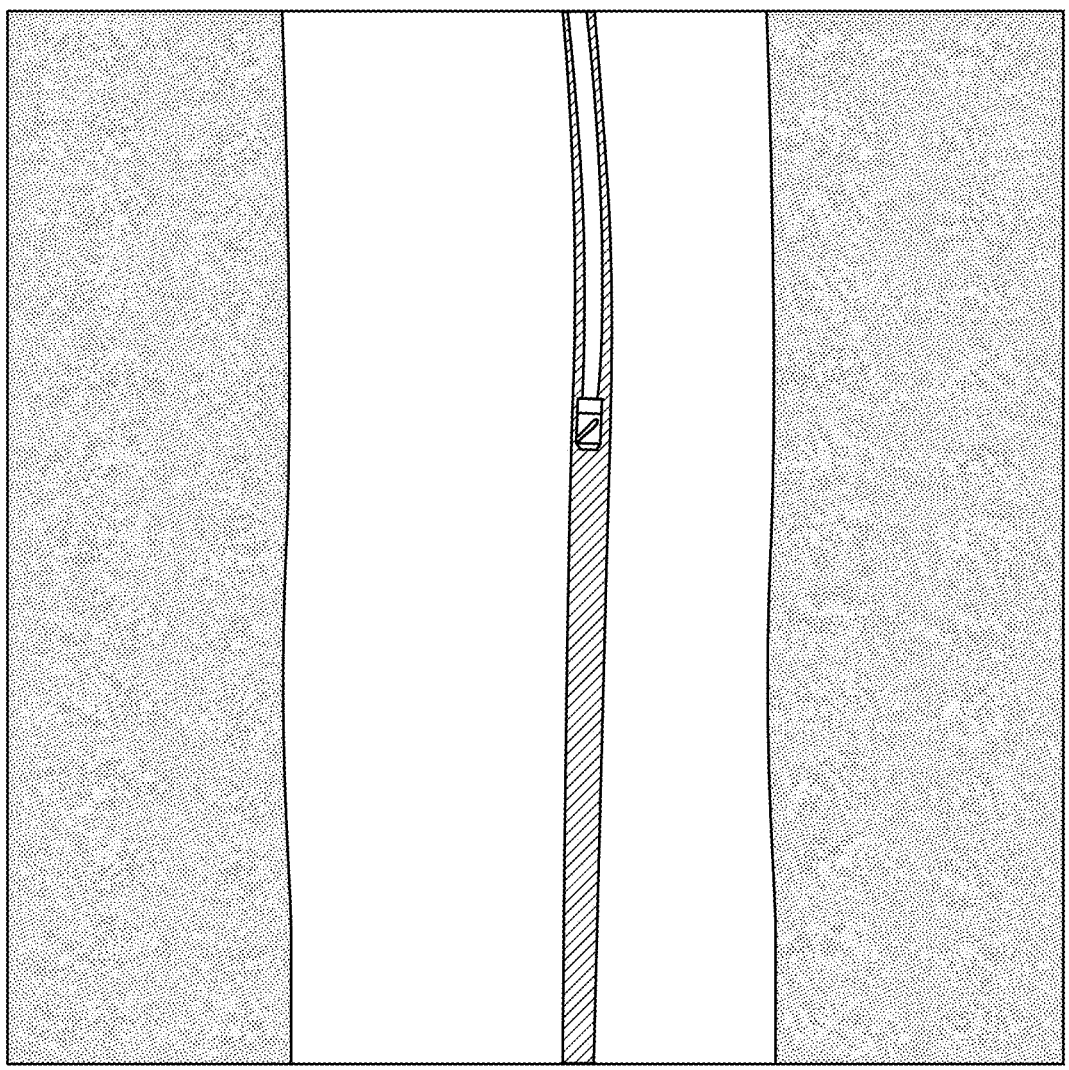
FIGS. 30A-30C illustrate operation of a guidewire positioning and support catheter such as the one illustrated above to traverse the occluded vessel shown in FIG. 29.
Figure 30B:
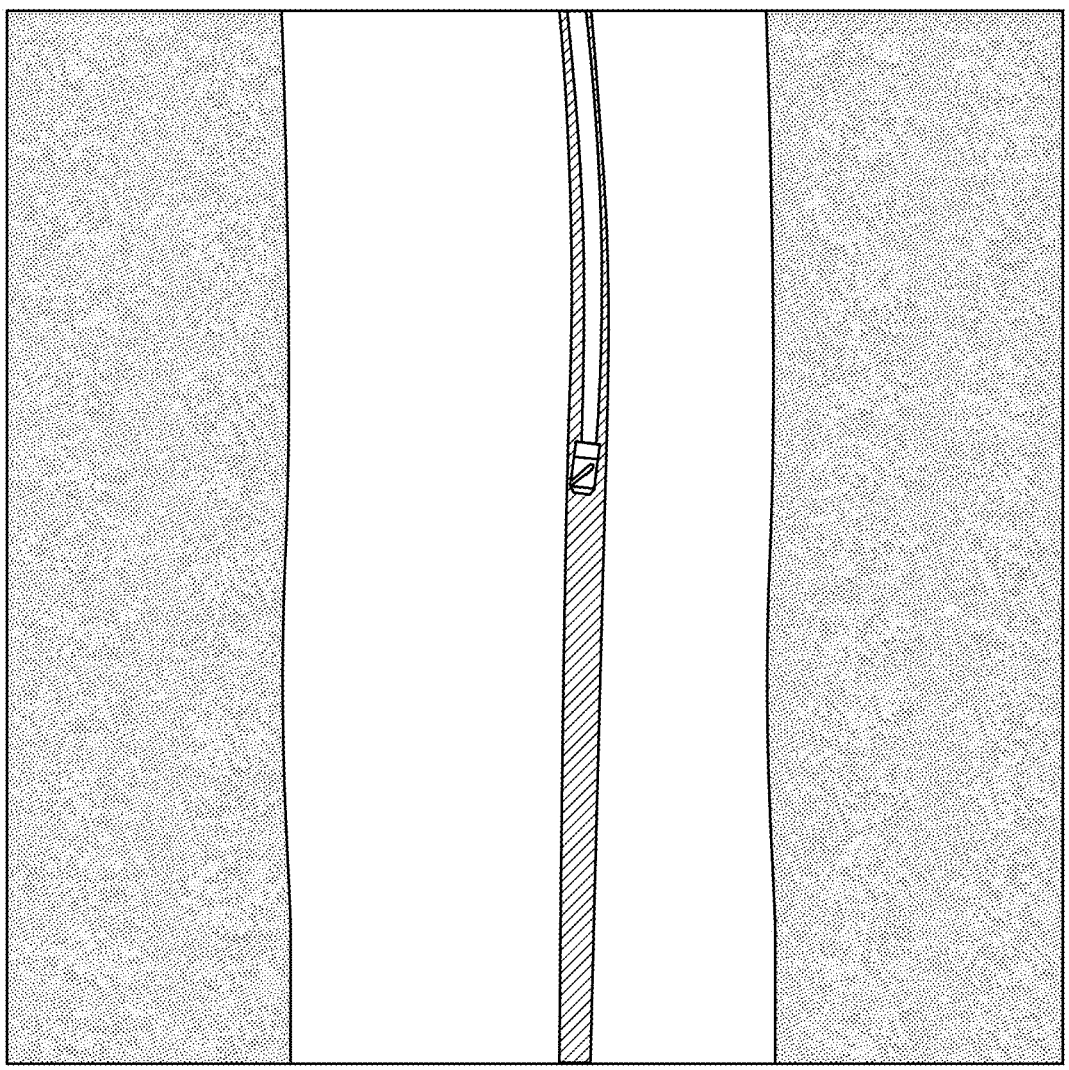
Figure 30C:
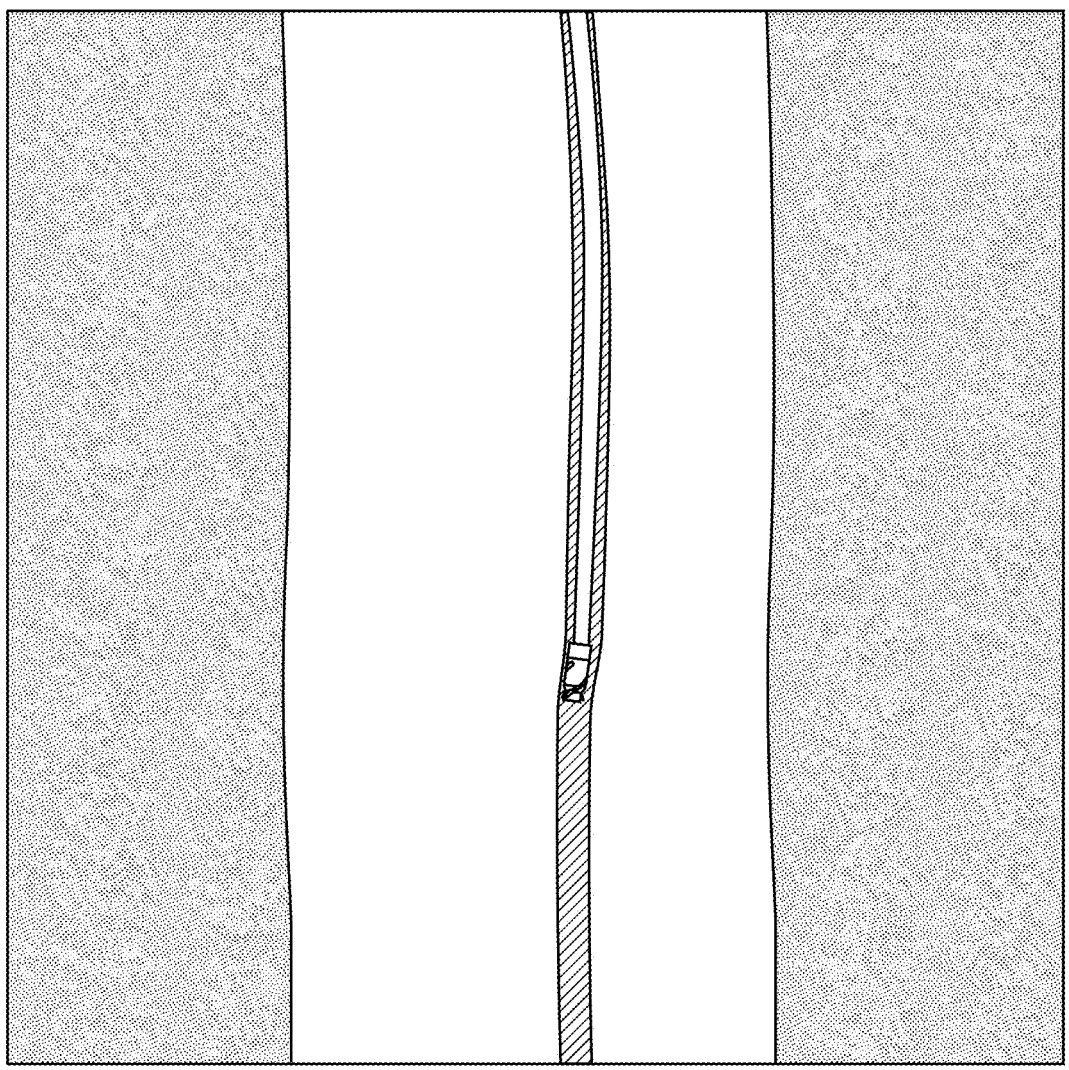

FIG. 29 shows a fluoroscopic image thorough a region of a subject's body having an occluded vessel. The occluded vessel extends from the top to the bottom of the figure. A dark column extending from the top of the figure shows the un-occluded portion of the vessel filled with contrast. FIGS. 30A-30C illustrate the use of the devices as described herein to traverse this occluded region carrying a guidewire that may be left in position (spanning the occlusion) after the catheter is removed. As illustrated, the catheter does not remove any substantial amount of material from the occlusion, but the rotation of the wedges at the distal tip allows it to advance around and through the occlusion within the vessel, forming a passage for the guidewire. Thereafter, the catheter may be removed, leaving the guidewire in position. The guidewire may then be used in conjunction with other devices, including stents or expanding balloon catheters that may be used to expand or remove the plaque or otherwise enlarge the vessel. For example, a catheter holding a balloon and/or stent may be delivered over the guidewire after it has been positioned.

FIGS. 31A and 31B illustrate the insertion of a device into a blood vessel. The vessel includes the media (e.g., tunica media) surrounded by adventitia (e.g., tunica adventitia). During operation, the devices described herein may be self-centering within the "true" lumen of the vessel, rather than a "false" lumen region between the adventitia and media, as illustrated in FIGS. 32A and 32B.

For example, any of the catheters described herein (referred to for convenience as a "Wildcat" device) may be used to treat peripheral vascular disease. When used to treat chronic total occlusions, the manually rotatable distal end (including the wedges) of the catheter may have been found to guide the catheter in the true lumen, especially when the reaching the distal cap of a lesion. Centering (self-centering) of the catheter appears to result from the rotation of the blades, coupled with the dimension of the device, including the diameter of the wedges and distal tip (which are typically the same as the diameter of the rest of the catheter). This rotating distal tip helps the device to stay in true lumen of the blood vessel. The blades (wedges) are configured to engage and dissect their way through tissue like the atheroma. For example, the rotating blades may create a sweeping path that is not only self-centering, but also is much bigger than the vessel wall (media). If a blade does engage with the media, it returns in the true lumen because the configuration of the device may help keep it within that space. As mentioned, the wedges may include a forward-cutting face (e.g., a blade or sharp edge that faces distally, away from the lateral sides, and therefore away from the walls of the lumen). The lateral portions of the wedge may be atraumatic, so that they don't cut or tear the lumen tissue. An atraumatic wedge portion may be rounded or otherwise dulled and configured so as not to cut the lumen. In some variations more than one wedge (e.g., two or more wedges) may be used. Thus, when one blade (wedge) is engaged with the vessel wall, the other blade continues making its way through the atheroma.

If the catheter device does end up in the sub-intimal plane (e.g., false lumen), as illustrated in FIGS. 32A and 32B, the device may reside between the media on one side and the adventitia on the other. The elastic nature of Adventitia typically prevents the wedge (and particularly atraumatic surfaces of the wedge) from engaging the tissue. At the same time it is easy for the rotating wedge(s) to engage with the media if it is presented in the front of the device, which may include the tissue-cutting surface(s). Thus, the rotating wedges may selectively dissect their way through the media and not through adventitia. Once the device dissects its way through the medial, it ends up back in the true lumen.

Figure 33:
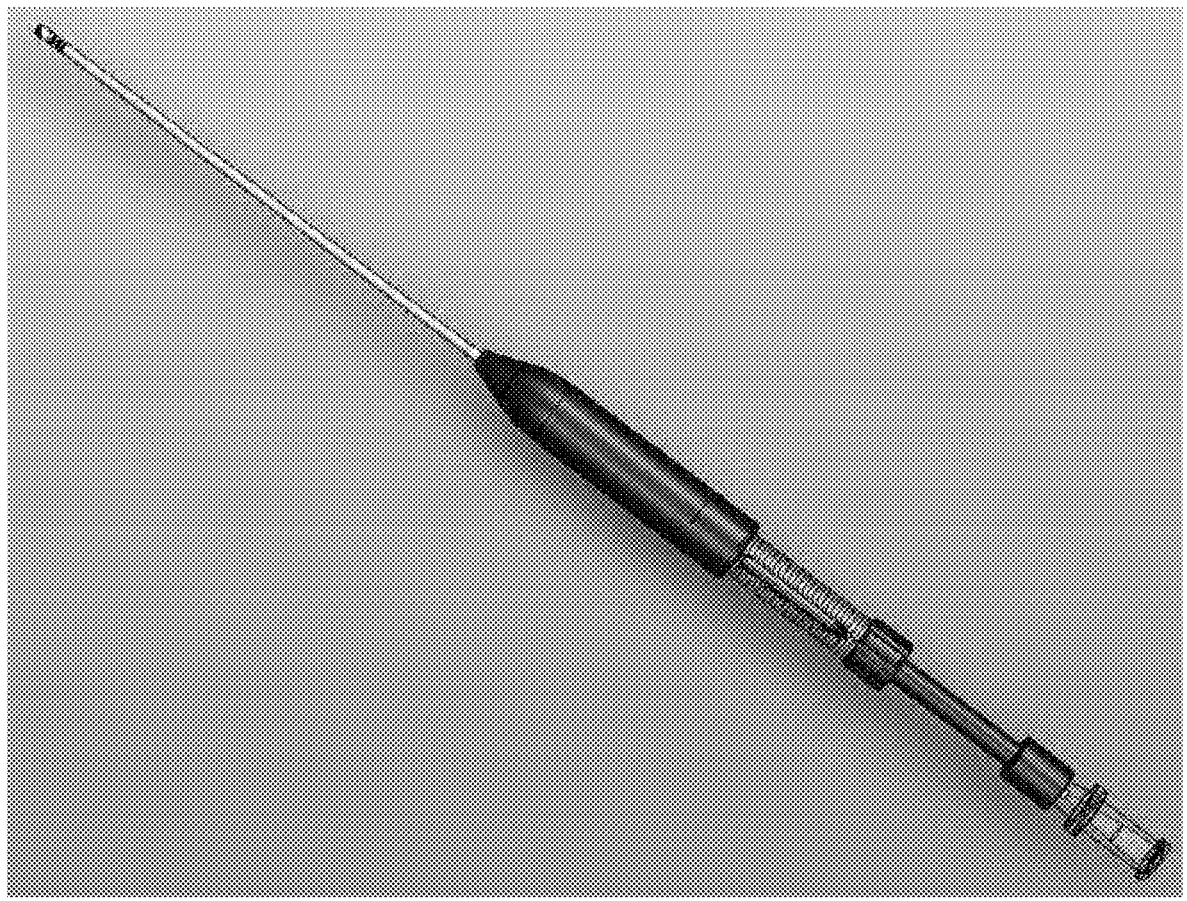
FIG. 33 is another variation of a guidewire positioning and support device.

FIG. 33 is another variation of a guidewire positioning and support catheter having a rotatable distal end with one or more extendable/retractable wedges. This device may also be used to position (e.g., providing a channel for) a guidewire or for traversing an occlusion in a vessel, particularly for traversing complete occlusions. This device may be used to support steerable guidewires (and may be used to guide them) in accessing discrete regions of the peripheral vasculature. It may be used to facilitate placement and exchange of guidewires and other interventional devices. It may also be used to deliver saline or contrast.

The variation shown in FIGS. 33-38 does not include a steerable distal end, as illustrated above. In this variation, the catheter includes an elongate catheter body having an outer diameter, and a rotatable distal tip. The rotatable distal tip includes a rotatable, extendable, wedge, and a rotatable protective housing. The extendable wedge is configured to be extended from the protective housing. In this variation, both the extendable wedge and protective housing have an outer diameter at least as wide as the diameter of the catheter (e.g., the distal half of the catheter). In some variations the wedge is a forward-cutting wedge having atraumatic lateral edges. The wedge region of the distal tip shown in FIGS. 33-38 are substantially similar to the wedge regions shown above (e.g., FIGS. 28A-28E).

Figure 34:
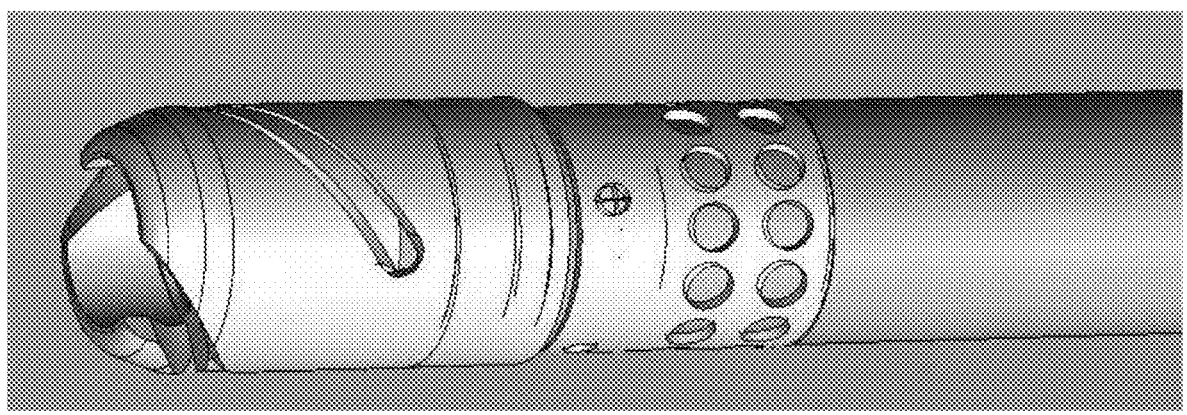
FIG. 34 shows an enlarged view of the distal end of the device of FIG. 33.
Figure 35:
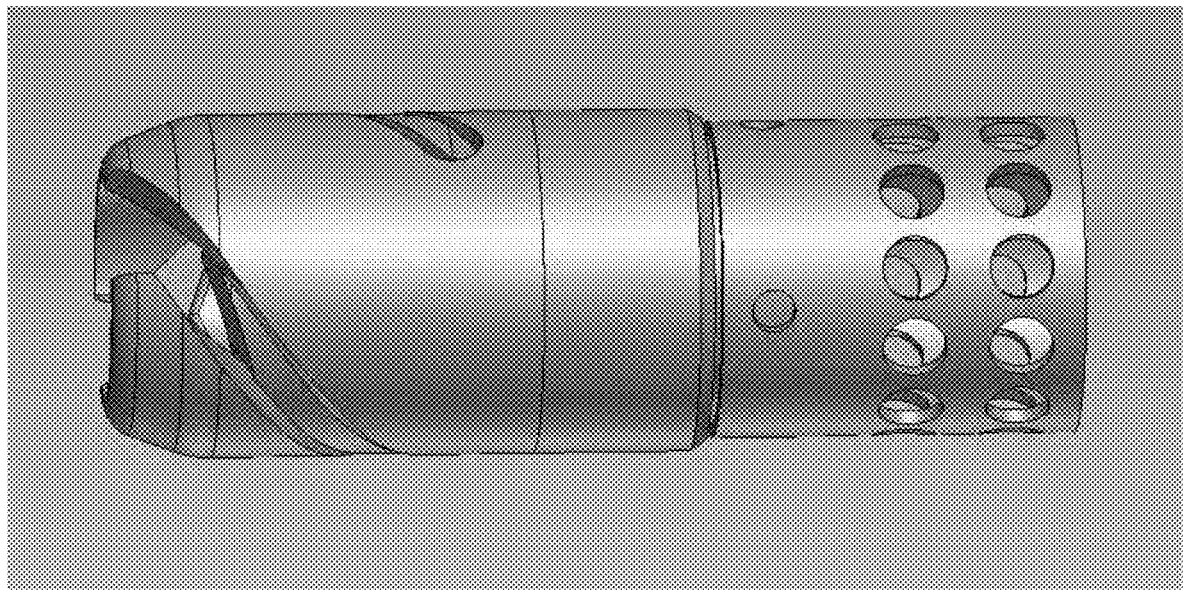
FIG. 35 shows another view of the distal tip region of the device of FIG. 33.
Figure 36:
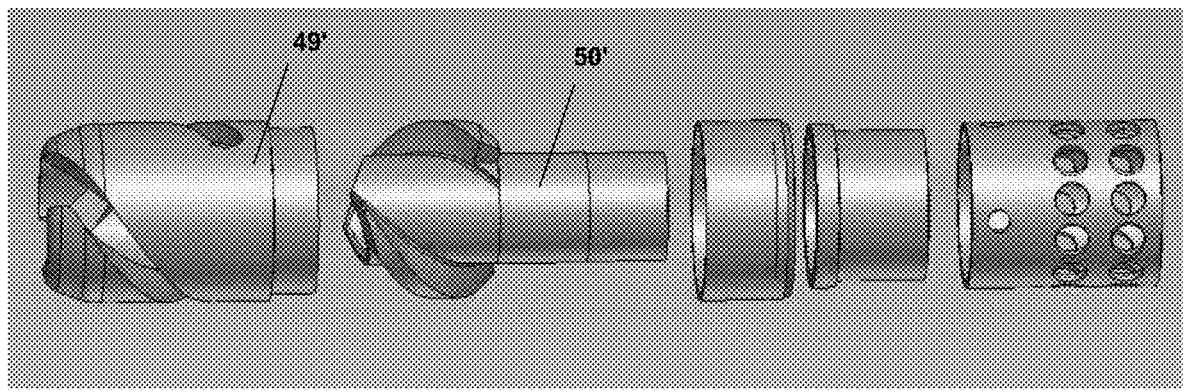
FIG. 36 is an exploded view of the distal tip region of the device of FIG. 33.

FIG. 34 shows an enlarged view of the distal end of the catheter of FIG. 33. FIG. 35 shows an alternative view in which the more proximal portion of the catheter has been removed. FIG. 36 shows an exploded view of the distal end of the device of FIGS. 33-35. In FIG. 36, the rotatable wedge portion 50' fits within the housing 49', and both the housing and the wedge portion are rotatable, as already described.

Figure 37A:
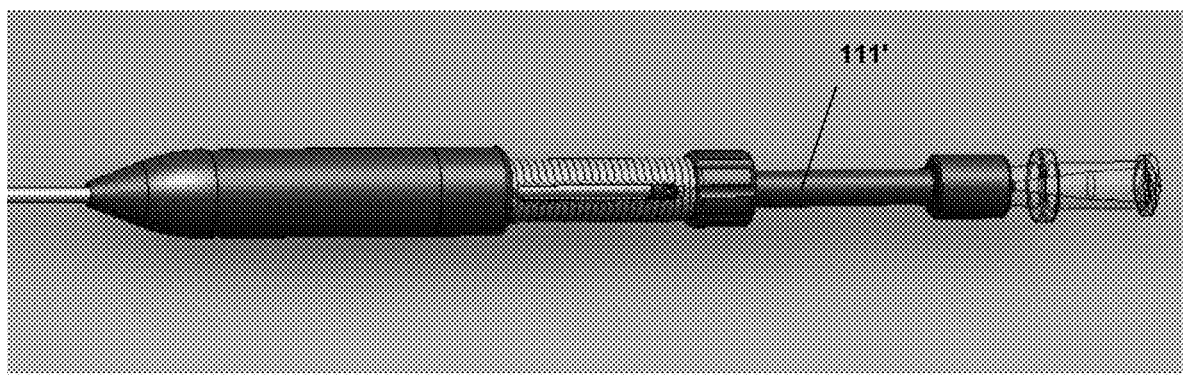
FIGS. 37A and 37B show increasingly enlarged views of the handle region of the device of FIG. 33.
Figure 37B:
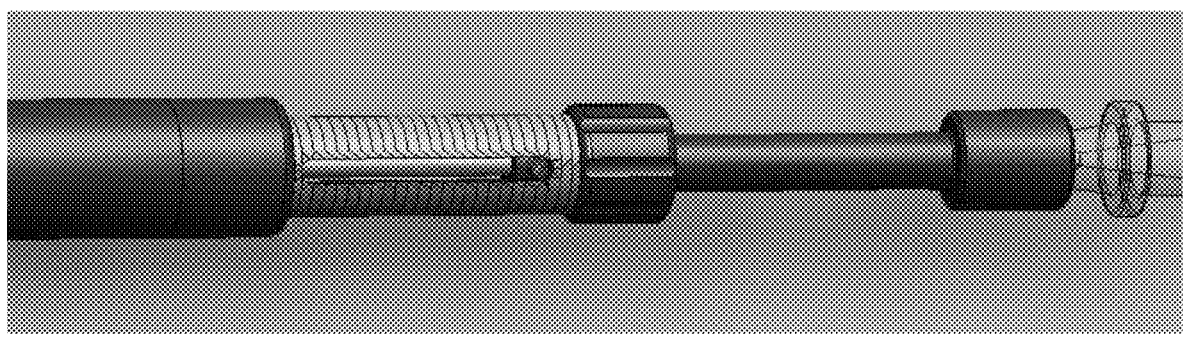
Figure 38:
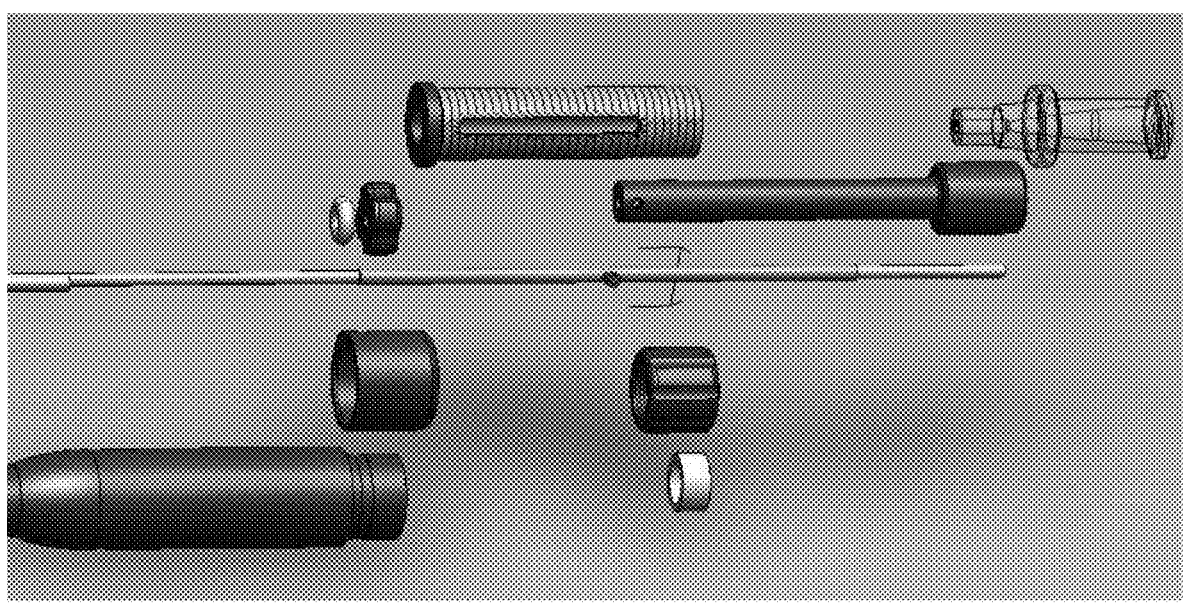
FIG. 38 is an exploded view of the handle shown for the device of FIG. 33.

FIGS. 37A and 37B illustrate progressively enlarged views of the proximal (handle) region of the device. In this variation, advancing the slider 111' in the distal direction will extend the wedge(s) from the protective housing. As mentioned above, the device may be configured so that the wedge portion cannot be fully extended from the housing. The device may also include an indicator. Finally, FIG. 38 shows an exploded view of the catheter handle.

Figure 39A:
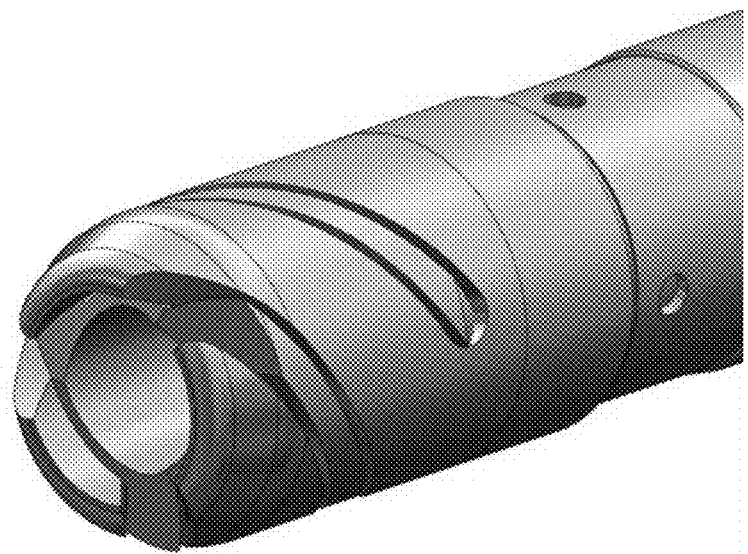
FIG. 39A shows one variation of a guidewire positioning and support device having three wedges in the retracted position.
Figure 39B:
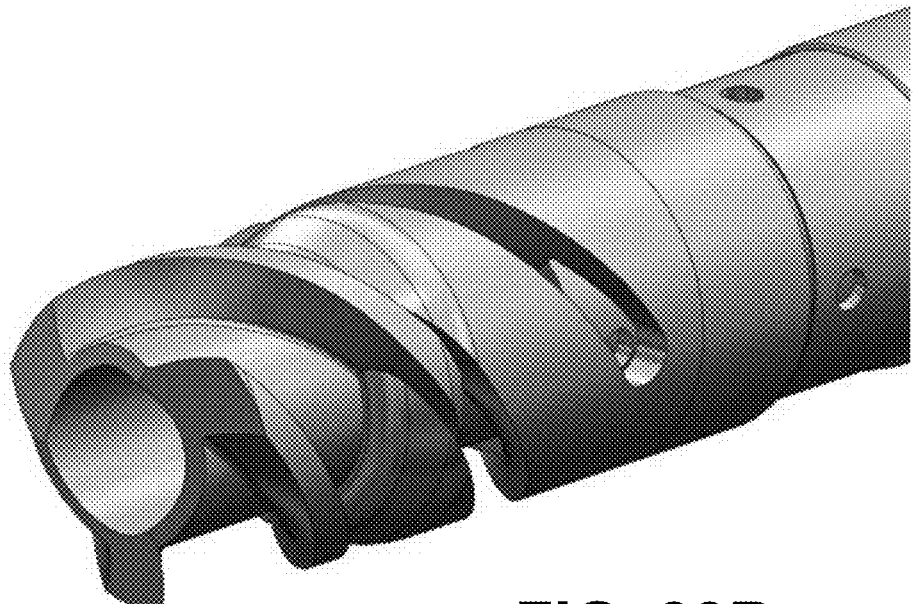
FIG. 39B shows the same device in which the wedges are extended.
Figure 40A:
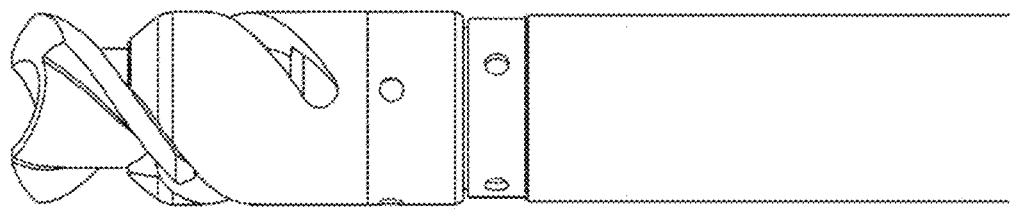
FIG. 40A illustrates one variation of a guidewire positioning device having a rotatable distal tip with a plurality (two in this example) of extendable wedges retractable into a rotating housing.
Figure 40B:
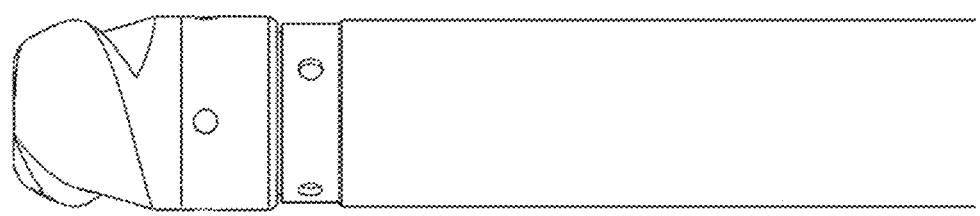
FIG. 40B shows another variation having an integrated rotatable distal tip with a pair of channeled flutes extending around from the distal end of the rotating tip that are configured to present a sharp cutting edge when the tip is rotated counter-clockwise, and to present a non-cutting (e.g., atraumatic) surface when the tip is rotated clockwise.
Figure 41A:
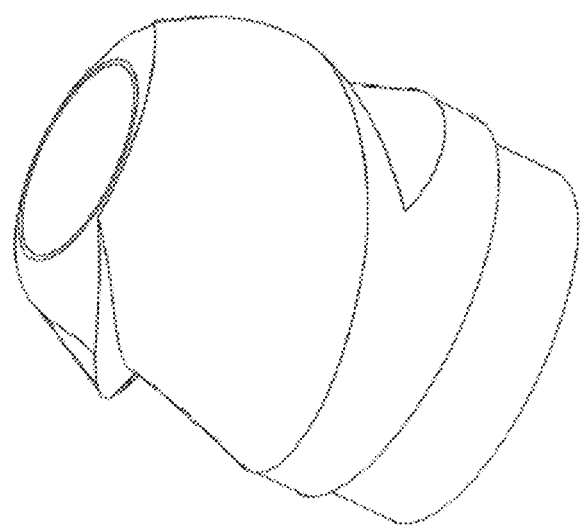
FIGS. 41A-41D show the rotatable distal tip of FIG. 40B in various views.
Figure 41B:
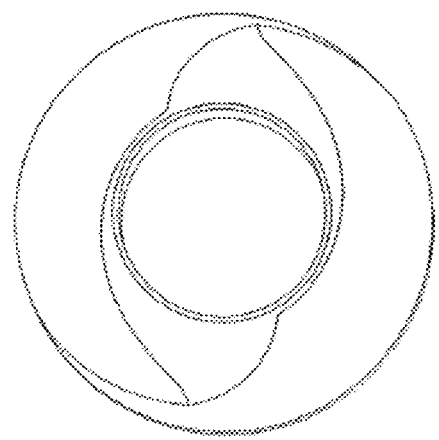
Figure 41C:
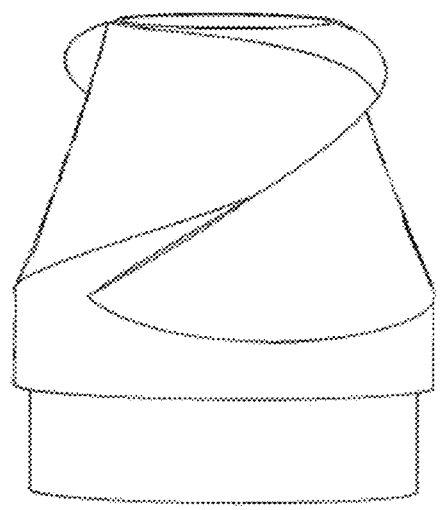
Figure 41D:
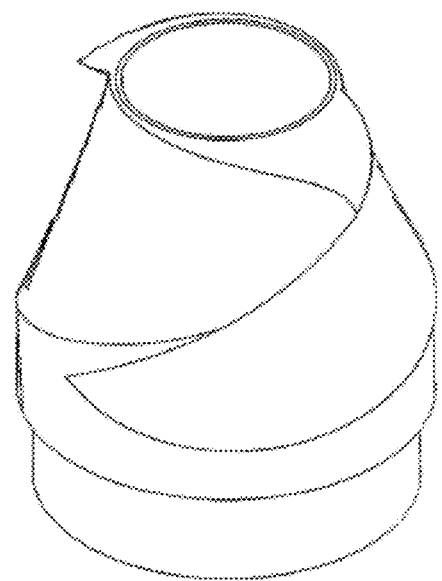

Any of the variations described herein may include one, two, three, or more wedges in the distal tip. It may be advantageous for the device to include three or more wedges that extend from the distal end. Having three or more wedges positioned around the distal end of the device may permit more equal distribution of the forces around the center of the tip. In addition, having three or more wedge may enhance the centering capability of the device. Devices having two wedges may engage the target tissue with only a single wedge at a time (e.g., in a lumen that is larger in diameter then the diameter of the device), which may cause the device to tend to spin around the engaged wedge or blade rather than the center of the device (e.g., the true center point of the catheter). For example, FIGS. 39A and 39B illustrate one variation of a device having three symmetrically positioned wedges shown in the retracted (FIG. 39A) and extended (FIG. 39B) positions.

FIGS. 40B to 41D illustrate another variation of a guidewire placement device. This variation may include many of the features described above, but includes an integrated (or "unified") rotatable distal tip. FIG. 40A is another illustration of the two-part rotatable distal tip including both an extendable/retractable rotatable wedge portion and a rotatable distal housing. The variations shown in FIG. 40B includes a rotatable distal tip in which the wedge and housing are integrated into a rotation-direction sensitive embodiment. In this variation, the distal tip is similar tin configuration to the distal housing, however the one or more spiral slots from which the wedges may extend are replaced with spiral flutes that act as spiral wedge members. Around the surface of the tip, the outer surface is smooth and flat when traveling in the counter-clockwise direction (e.g., see FIGS. 41A-41D), while traversing the tip in the clockwise direction encounters multiple sharp edges. Thus, as the tip is rotated clockwise, the tissue is passively engaged by the rotating atraumatic (non-cutting) surface. Rotation of the tip in the opposite (counterclockwise) direction presents multiple cutting edges.

In operation, the variation shown in FIGS. 40B-41D may be operated similar to those described above, however the wedges do not need to be extended/retracted as described. Instead, the cutting/non-cutting surfaces (corresponding to the extended/retracted configuration of other variations) may by operated depending on the direction of rotation of the distal tip. As mentioned above, the distal tip may be manually rotated, allowing both control of the speed and/or direction of rotation (e.g., by twisting a control to rotate the distal tip, etc.).

The examples and illustrations included herein show, by way of illustration and not of limitation, specific embodiments in which the subject matter may be practiced. Other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A catheter device for positioning a guidewire across an occluded portion of a vessel, the catheter device comprising:
   a catheter body having a central lumen and a steerable distal region, the steerable distal region configured to bend laterally toward a predetermined side of the catheter body, wherein a distal end of the catheter body includes spiral shaped wedge members; and
   a driveshaft extending within the central lumen and configured to rotate with respect to of the catheter body, the driveshaft coupled to and configured to rotate a distal tip having one or more cutting edges, wherein the driveshaft is configured to move longitudinally relative to the catheter body to extend the distal tip distally out of a central opening of the distal end of the catheter body and retract the distal tip proximally within the catheter body, wherein the one or more cutting edges are arranged in a spiral that is radially aligned with the spiral shaped wedge members of the distal end of the catheter body when the one or more cutting edges are extended out of the distal end of the catheter body, wherein the catheter device is configured to lock at least a portion of the distal tip in an extended position out of the central opening of the distal end of the catheter body, wherein the steerable distal region of the catheter body is configured to bend laterally toward the predetermined side of the catheter body upon application of a longitudinal pushing force on the driveshaft.

2. The catheter device of claim 1, further comprising a handle configured to control lateral bending of the catheter body, and extension and retraction of the distal tip.

3. The catheter device of claim 2, wherein the handle further comprises an indicator configured to indicate an extent to which the distal tip is extended.

4. The catheter device of claim 2, wherein the handle is further configured to control rotation of the driveshaft and the distal tip.

5. The catheter device of claim 4, wherein the handle comprises:
   a first control configured to control rotation of the driveshaft and the distal tip; and
   a second control configured to control lateral bending of the catheter body, and extension and retraction of the distal tip with respect to the catheter body, by controlling longitudinal movement of the driveshaft.

6. The catheter device of claim 5, wherein the first control includes a slider component, and wherein the second control includes a rotator component.

7. The catheter device of claim 6, wherein the slider component is configured to slide distally to extend the distal tip distally out of the catheter body, and slide further distally to bend the steerable distal region.

8. The catheter device of claim 2, wherein the handle further comprises a lock configured to lock the catheter body in a bent configuration or a straight configuration.

9. The catheter device of claim 8, wherein the handle further comprises a slider component configured to slide longitudinally, wherein the lock is configured to restrict movement of the slider component.

10. The catheter device of claim 2, wherein the handle further comprises a luer connecter that provides entry to a lumen of the catheter device.

11. The catheter device of claim 1, wherein rotation of the driveshaft is driven by a motor.

12. The catheter device of claim 1, wherein the driveshaft and the distal tip are configured to rotate in either a clockwise direction or a counterclockwise direction.

13. The catheter device of claim 1, wherein the steerable distal region of the catheter body includes a scaffold having a narrow solid band that extends longitudinally along the scaffold, wherein the steerable distal region is configured to bend toward the narrow solid band.

14. The catheter device of claim 1, wherein the device includes a lock that is configured to lock at least a portion of the one or more cutting edges in the extended position.

15. The catheter device of claim 1, wherein the one or more cutting edges are configured to extend from the distal end of the catheter body by a predetermined maximum extension when locked in the extended position.

16. A method of positioning a guidewire across an occlusion within a vessel, the method comprising:
 advancing a catheter device through the vessel and toward the occlusion, the catheter device comprising:
  a catheter body having a lumen and steerable distal region, wherein a distal end of the catheter body includes spiral shaped wedge members; and
  a driveshaft extending within the lumen, the driveshaft coupled to a distal tip having one or more cutting edges;
 crossing the occlusion by:
  extending the distal tip distally from within the catheter body to expose the one or more cutting edges, wherein at least a portion of the distal tip is locked in an extended position out of a central opening of the distal end of the catheter body, and wherein the one or more cutting edges are arranged in a spiral that is radially aligned with the spiral shaped wedge members of the distal end of the catheter body when the one or more cutting edges are extended out of the distal end of the catheter body;
  rotating the driveshaft to cause the distal tip to rotate and cut the occlusion with the one or more cutting edges of the distal tip; and
  applying a longitudinal pushing force on the driveshaft to cause the steerable distal region of the catheter body to bend laterally toward a predetermined side of the steerable distal region and to steer the rotating distal tip within the vessel; and
 positioning the guidewire through the catheter body and across the occlusion.

17. The method of claim 16, wherein rotating the distal tip comprises rotating the distal tip in a clockwise direction and a counterclockwise direction.

18. The method of claim 16, wherein the catheter device includes a handle having a first control and a second control, wherein rotating the distal tip comprises manipulating the first control, wherein extending the distal tip distally comprises manipulating the second control.

19. The method of claim 18, wherein the second control controls longitudinal movement of the driveshaft.

20. The method of claim 16, further comprising delivering fluid to a desired area within the vessel through the lumen of the catheter device.

21. The method of claim 16, further comprising locking the steerable distal region in a bent configuration.

22. The method of claim 21, wherein locking the steerable distal region in the bent configuration comprises restricting longitudinal movement of the driveshaft within the catheter body.

* * * * *